US008247537B2

(12) United States Patent
Korman et al.

(10) Patent No.: US 8,247,537 B2
(45) Date of Patent: Aug. 21, 2012

(54) HUMAN MONOCLONAL ANTIBODIES TO BTLA AND METHODS OF USE

(75) Inventors: Alan Korman, Piedmont, CA (US);
Mark Selby, San Francisco, CA (US);
Kent B. Thuduim, Oakland, CA (US);
Edward Halk, Sunnyvale, CA (US);
Mohan Srinivasan, San Jose, CA (US);
David B. Passmore, San Carlos, CA (US)

(73) Assignee: Medarex, Inc., Princeton, NJ (US)

( * ) Notice: Subject to any disclaimer, the term of this patent is extended or adjusted under 35 U.S.C. 154(b) by 9 days.

(21) Appl. No.: 12/515,004

(22) PCT Filed: Nov. 15, 2007

(86) PCT No.: PCT/US2007/084792
§ 371 (c)(1),
(2), (4) Date: Mar. 8, 2010

(87) PCT Pub. No.: WO2008/076560
PCT Pub. Date: Jun. 26, 2008

(65) Prior Publication Data
US 2010/0172900 A1 Jul. 8, 2010

Related U.S. Application Data

(60) Provisional application No. 60/866,058, filed on Nov. 15, 2006.

(51) Int. Cl.
*C07K 16/00* (2006.01)
*A61K 39/395* (2006.01)
(52) U.S. Cl. .................. 530/388.1; 424/141.1
(58) Field of Classification Search .......... None
See application file for complete search history.

(56) References Cited

U.S. PATENT DOCUMENTS

| | | | | |
|---|---|---|---|---|
| 6,632,927 B2 * | 10/2003 | Adair et al. | ......... | 530/387.3 |
| 7,304,149 B2 | 12/2007 | Murphy et al. | | |
| 7,601,818 B2 * | 10/2009 | Wild et al. | ......... | 530/388.24 |
| 2004/0175380 A1 * | 9/2004 | Allison et al. | ......... | 424/144.1 |
| 2005/0074821 A1 | 4/2005 | Wild et al. | | |

FOREIGN PATENT DOCUMENTS

| | | |
|---|---|---|
| WO | WO2004/000221 | 12/2003 |
| WO | WO2006/054961 | 5/2006 |

OTHER PUBLICATIONS

Rudikoff et al. 1982, Proc. Natl. Acad. Sci. USA, 79: 1979-1983.*
Panka et al., 1988, Proc. Natl. Acad. Sci. USA, 85: 3080-3084.*
Croft M, "The evolving crosstalk between co-stimulatory and co-inhibitory receptors: HVEM-BTLA", *Trends in Immunology*, vol. 26, No. 6, pp. 292-294, Jun. 1, 2005, XP004938746.
Han, Peggy et al. "An inhibitory ig superfamily protein expressed by lymphocytes and APCs is also an early marker of thymocyte positive selection", *Journal of Immunology*, vol. 172, No. 10, pp. 5931-5939, May 15, 2004, XP002609096.
Krieg, Cartsen et al., "Functional analysis of B and T lymphocyte attenuator engagement on CD4+ and CD8+ T cells", *Journal of Immunology*, vol. 175, No. 10, pp. 6420-6427, Nov. 15, 2005, XP002609095.
Kroczek et al. "T-cell costimulatory molecules: Optimal targets for the treatment of allergic airway disease with monoclonal antibodies", *Journal of Allergy and Clinical Immunology*, vol. 116, No. 4, pp. 906-909, Oct. 1, 2005, XP005094486.
Mei, L. et al. "300 Genetic variation in BTLA is strongly associated with chron's disease", *Gastroenterology*, vol. 134, No. 4, pp. A-42, Apr. 1, 2008, XP023432000.
Zheng, Chun et al.. "BTLA, a new inhibitory B7 family receptor with a TNFR family ligand", *Cellular & Molecular Immunology*, vol. 2, No. 6, pp. 427-432, Dec. 1, 2005, XP009107717.
Pini A, et al., "Design and use of a phage display library. Human antibodies with subnanomolar affinity against a marker of angiogenesis eluted from a two-dimensional gel," J Bial Chem. Aug. 21, 1998;273(34):21769-76.
Holt Li, et al., "Domain antibodies: proteins for therapy," Trends Biotechnol. Nov. 2003;21(11):484-90.
Davies J and Riechmann L, "Affinity improvement of single antibody VH domains: residues in all three hypervariable regions affect antigen binding," Immunotechnology. Sep. 1996;2(3):169-79.
Maynard J and Georgiou G, "Antibody engineering," Annu Rev Biomed Eng. 2000;2:339-76.

* cited by examiner

*Primary Examiner* — Ilia Ouspenski
(74) *Attorney, Agent, or Firm* — Baker Botts LLP

(57) ABSTRACT

The present disclosure provides isolated monoclonal antibodies, particularly human monoclonal antibodies that specifically bind to BTLA with high affinity. Nucleic acid molecules encoding the antibodies of the disclosure, expression vectors, host cells and methods for expressing the antibodies of the disclosure are also provided. Immunoconjugates, bispecific molecules and pharmaceutical compositions comprising the antibodies of the disclosure are also provided. The disclosure also provides methods for detecting BTLA, as well as methods for treating various diseases, including cancer and infectious diseases, using anti-BTLA antibodies.

18 Claims, 41 Drawing Sheets

Anti-BTLA 1B4 VH

V segment:    2-05
D segment:    3-10
J segment:    JH6b

```
      Q   I   T   L   K   E   S   G   P   T   L   V   K   P   T   Q   T   L
  1   CAG ATC ACC TTG AAG GAG TCT GGT CCT ACG CTG GTG AAA CCC ACA CAG ACC CTC
                                                                      CDR1
                                                                      ~~~~~~~~~~~~~~~~~~~~
      T   L   T   C   T   F   S   G   F   S   L   N   T   I   G   V   G   V
 55   ACG CTG ACC TGC ACC TTC TCT GGG TTC TCA CTC AAC ACT ATT GGA GTG GGT GTA

CDR1                                                            CDR2
      ~~~                                                             ~~~~~~~~~~~~~
      N   W   I   R   Q   P   P   G   K   A   L   E   W   L   A   L   I   Y
109   AAC TGG ATC CGT CAG CCC CCA GGA AAG GCC CTG GAG TGG CTT GCA CTC ATT TAT

CDR2
      ~~~~~~~~~~~~~~~~~~~~~~~~~~~~~~~~~~~~~~~~~~~~~~~~~~~~
      W   D   D   D   K   R   Y   S   P   S   L   K   R   R   L   T   I   S
163   TGG GAT GAT GAT AAG CGC TAC AGC CCA TCT CTG AAG AGG AGG CTC ACC ATC TCC

K   D   T   S   K   N   Q   V   V   L   T   M   T   N   M   D   P   V
217   AAG GAC ACC TCC AAA AAC CAG GTG GTC CTC ACA ATG ACC AAC ATG GAC CCT GTG
                                                          CDR3
                                                          ~~~~~~~~~~~~~~~~~~~~
      D   T   A   T   Y   Y   C   A   H   S   G   I   T   E   V   R   G   V
271   GAC ACA GCC ACA TAT TAC TGT GCA CAC AGC GGG ATT ACT GAG GTT CGG GGA GTT

CDR3
      ~~~~~~~~~~~~~~~~~~~~~~~~~~~~~~~~
      I   I   H   Y   Y   G   M   D   V   W   G   Q   G   T   T   V   T   V
325   ATT ATA CAT TAC TAC GGT ATG GAC GTC TGG GGC CAA GGG ACC ACG GTC ACC GTC

S   S
379   TCC TCA
```

FIG.1A

Anti-BTLA 1B4 VK

V segment: A27
J segment: JK5

```
      E   I   V   L   T   Q   S   P   G   T   L   S   L   S   P   G   E   R
  1  GAA ATT GTG TTG ACG CAG TCT CCA GGC ACC CTG TCT TTG TCT CCA GGG GAA AGA

CDR1
                              ~~~~~~~~~~~~~~~~~~~~~~~~~~~~~~~~~~~~~~~~~~~~~~~
      A   T   L   S   C   R   A   S   Q   S   V   S   S   S   Y   L   A   W
 55  GCC ACC CTC TCC TGC AGG GCC AGT CAG AGT GTT AGC AGC AGC TAC TTA GCC TGG

CDR2
                                                          ~~~~~~~~~~~~~~~~~~~
      Y   Q   Q   K   P   G   Q   A   P   R   L   L   I   Y   G   A   S   S
109  TAC CAG CAG AAA CCT GGC CAG GCT CCC AGG CTC CTC ATC TAT GGT GCA TCC AGC

CDR2
  ~~~~~~~~~~~~~~
      R   A   T   G   I   P   D   R   E   S   G   S   G   S   F   T   D   F
163  AGG GCC ACT GGC ATC CCA GAC AGG TTC AGT GGC AGT GGG TCT GGG ACA GAC TTC

---
      T   L   T   I   S   R   L   E   P   E   D   F   A   V   Y   Y   C   Q
217  ACT CTC ACC ATC AGC AGA CTG GAG CCT GAA GAT TTT GCA GTG TAT TAC TGT CAG

CDR3
     ~~~~~~~~~~~~~~~~~~~~~~~
      Q   Y   G   S   S   I   T   F   G   Q   G   T   R   L   E   I   K
271  CAG TAT GGT AGC TCA ATC ACC TTC GGC CAA GGG ACA CGA CTG GAG ATT AAA
```

FIG. 1B

Anti-BTLA E4H9 VH

V segment: 2-70
D segment: 3-10
J segment: JH6b

```
      Q   V   T   L   R   E   S   G   P   A   L   V   K   P   T   Q   T   L
  1   CAG GTC ACC TTG AGG GAG TCT GGT CCT GCG CTG GTG AAA CCC ACA CAG ACC CTC
```

CDR1
                                   ——————————————

```
      T   L   T   C   T   F   S   G   F   S   L   S   T   S   G   M   C   V
 55   ACA CTG ACC TGC ACC TTC TCT GGG TTC TCA CTC AGC ACT AGT GGA ATG TGT GTG
```

CDR1                               CDR2
~~~                           ——————————

```
      S   W   I   R   Q   P   P   G   K   A   L   E   W   L   A   L   I   D
109   AGC TGG ATC CGT CAG CCC CCA GGG AAG GCC CTG GAG TGG CTT GCA CTC ATT GAT
```

CDR2
——————————————————————————————————

```
      W   D   D   V   K   Y   Y   S   S   S   L   K   T   K   L   T   I   S
163   TGG GAT GAT GTT AAA TAC TAC AGC TCA TCT CTG AAG ACC AFG CTC ACC ATC TCC

K   D   T   S   K   N   Q   V   V   L   T   M   T   D   M   D   P   V
217   AAG GAC ACC TCC AAA AAC CAG GTG GTC CTT ACA ATG ACC GAC ATG GAC CCT GTG
```

CDR3
                           ——————————

```
      D   T   A   T   Y   Y   C   A   R   I   R   F   T   M   F   R   G   V
271   GAC ACT GCC ACG TAT TAC TGT GCA CGG ATA CGG TTT ACT ATG TTT CGG GGA GTC
```

CDR3
————————————————————————

```
      Y   Y   Y   Y   Y   G   L   D   V   W   G   Q   G   T   T   V   T   V
325   TAC TAC TAT TAC TAC GGT TTG GAC GTC TGG GGC CAA GGG ACC ACG GTC ACC GTC

S   S
379   TCC TCA
```

FIG.2A

Anti-BTLA E4H9 VK

V segment: A27
J segment: JK3

```
      E   I   V   L   T   Q   S   P   G   T   L   S   L   S   P   G   E   R
  1  GAA ATT GTG TTG ACG CAG TCT CCA GGC ACC CTG TCT TTG TCT CCA GGG AAA AGA
```

CDR1
                ~~~~~~~~~~~~~~~~~~~~~~~~~~~~~~~~~~~~~~~~~~~~~~~~
```
      A   T   L   S   C   R   A   S   Q   S   V   S   S   S   Y   L   A   W
 55  GCC ACC CTC TCC TGC AGG GCC AGT CAG AGT GTT AGC AGC AGC TAC TTA GCC TGG
```

CDR2
                                                        ~~~~~~~~~~~~~~
```
      Y   Q   Q   K   P   G   Q   A   P   R   L   L   I   Y   G   A   S   S
 109 TAC CAG CAG AAA CCT GGC CAG GCT CCC AGG CTC CTC ATC TAT GGT GCA TCC AGC
```

CDR2
     ~~~~~~~~~~
```
      R   A   T   G   I   P   D   R   F   S   G   S   G   S   G   T   D   F
 163 AGG GCC ACT GGC ATC CCA GAC AGG TTC AGT GGC AGT GGG TCT GGG ACA GAC TTC
```

CDR3
                                                                     ~~~~
```
      T   L   T   I   S   R   L   E   P   E   D   F   A   V   Y   Y   C   Q
 217 ACT CTC ACC ATC AGC AGA CTG GAG CCT GAA GAT TTT GCA GTG TAT TAC TGT CAG
```

CDR3
     ~~~~~~~~~~~~~~~~~~~~~~~~~~~~~
```
      Q   Y   G   S   S   P   P   I   T   F   G   P   G   T   K   V   D   I
 271 CAG TAT GGT AGC TCA CCT CCG ATC ACT TTC GGC CCT GGG ACC AAA GTG GAT ATC
```

```
      K
 325 AAA
```

FIG.2B

Anti-BTLA 3C2 VH

V segment:     4-59
D segment:         6-19
J segment:     JH4b

```
      Q   V   Q   L   Q   E   S   G   P   G   L   V   K   P   S   E   T   L
  1   CAG GTG CAG CTG CAG GAG TCG GGC CCA GGA CTG GTG AAG CCT TCG GAG ACC CTG

CDR1
                                                        ~~~~~~~~~~~~~~~~~~~
      S   L   T   C   T   I   S   G   G   S   I   S   N   Y   Y   W   N   W
 55   TCC CTC ACC TGC ACT ATC TCT GGT GGC TCC ATC AGT AAT TAC TAC TGG AAC TGG

CDR2
                                                        ~~~~~~~~~~~~~~~~~~~
      I   R   Q   P   P   G   K   G   L   E   W   I   G   Y   I   Y   Y   S
109   ATC CGG CAG CCC CCA GGG AAG GGA CTG GAG TGG ATT GGG TAT ATC TAT TAC AGT

CDR2
      ~~~~~~~~~~~~~~~~~~~~~~~~~~~~~~~~~~
      T   S   T   K   Y   N   P   S   L   K   S   R   V   T   M   S   V   E
163   ACG AGC ACC AAG TAC AAC CCC TCC CTC AAG AGT CGA GTC ACC ATG TCA GTA GAG

T   S   K   N   Q   F   S   L   K   L   S   S   V   T   A   A   D   T
217   ACG TCC AAG AAC CAG TTC TCC CTG AAG CTG AGC TCT GTG ACC GCT GCG GAC ACG

CDR3
                                              ~~~~~~~~~~~~~~~~~~~~~~~~~~~~~~
      A   V   Y   Y   C   A   R   V   K   V   Y   S   T   G   W   F   F   D
271   GCC GTG TAT TAC TGT GCG AGA GTG AAA GTG TAT AGC ACT GGC TGG TTC TTT GAC

CDR3
     ~~~
      Y   W   G   Q   G   T   L   V   T   V   S   S
325   TAC TGG GGC CAG GGA ACC CTG GTC ACC GTC TCC TCA
```

FIG.3A

Anti-BTLA 3C2 VK1

V segment:   L18
J segment:   JK4

```
      A   I   Q   L   T   Q   S   P   S   S   L   S   A   S   V   G   D   R
  1  GCC ATC CAG TTG ACC CAG TCT CCA TCC TCC CTG TCT GCA TCT GTA GGA GAC AGA
```

CDR1
                               ~~~~~~~~~~~~~~~~~~~~~~~~~~~~~~~~~~~~~~~~~~~~

```
      V   T   I   T   C   R   A   S   Q   G   I   S   S   A   L   A   W   Y
 55  GTC ACC ATC ACT TGC CGG GCA AGT CAG GGC ATT AGC AGT GCT TTA GCC TGG TAT
```

CDR2
                                                            ~~~~~~~~~~~~~~~~

```
      Q   Q   K   P   G   K   A   P   K   L   L   I   Y   D   A   S   S   L
109  CAG CAG AAA CCA GGG AAA GCT CCT AAG CTC CTG ATC TAT GAT GCC TCC AGT TTG
```

CDR2
     ~~~~~~

```
      E   S   G   V   P   S   R   F   S   G   S   G   S   G   T   D   F   T
163  GAA AGT GGG GTC CCA TCA AGG TTC AGC GGC AGT GGA TCT GGG ACA GAT TTC ACT
```

CDR3
                                                                    ~~~~~~~~

```
      L   T   I   S   S   L   Q   P   E   D   F   A   T   Y   Y   C   Q   Q
217  CTC ACC ATC AGC AGC CTG CAG CCT GAA GAT TTT GCA ACT TAT TAC TGT CAA CAG
```

CDR3
     ~~~~~~~~~~~~~~~~~~~~

```
      F   N   S   Y   P   L   T   F   G   G   G   T   K   V   E   I   K
271  TTT AAT AGT TAC CCT CTC ACT TTC GGC GGA GGG ACC AAG GTG GAG ATC AAA
```

FIG.3B

Anti-BTLA 3C2 VK2

V segment:   A27
J segment:   JK2

```
      E   I   V   L   T   Q   S   P   G   T   L   S   L   S   P   G   E   R
  1 GAA ATT GTG TTG ACG CAG TCT CCA GGC ACC CTG TCT TTG TCT CCA GGG AAA AGA
```

CDR1

```
      A   T   L   S   C   R   A   S   Q   S   V   S   S   S   Y   L   A   W
 55 GCC ACC CTC TCC TGC AGG GCC AGT CAG AGT GTT AGC AGC AGC TAC TTA GCC TGG
```

CDR2

```
      Y   Q   Q   K   P   G   Q   A   P   R   L   L   I   Y   G   A   S   S
109 TAC CAG CAG AAA CCT GGC CAG GCT CCC AGG CTC CTC ATC TAT GGT GCA TCC AGC
```

CDR2

```
      R   A   T   G   I   P   D   R   F   S   G   S   G   S   G   T   D   F
163 AGG GCC ACT GGC ATC CCA GAC AGG TTC AGT GGC AGT GGG TCT GGG ACA GAC TTC
```

CDR3

```
      T   L   T   I   S   R   L   E   P   E   D   F   A   V   Y   Y   C   Q
217 ACT CTC ACC ATC AGC AGA CTG GAG CCT GAA GAT TTT GCA GTG TAT TAC TGT CAG
```

CDR3

```
      Q   Y   G   S   S   P   Y   T   F   G   Q   G   T   K   L   E   I   K
271 CAG TAT GGT AGC TCA CCG TAC ACT TTT GGC CAG GGG ACC AAG CTG GAG ATC AAA
```

FIG.3C

Anti-BTLA 6A5 VH

V segment: 2-05
D segment: 3-10
J segment: JH6b

```
      Q   I   T   L   K   E   S   G   P   T   L   V   K   P   T   Q   T   L
  1  CAG ATC ACC TTG AAG GAG TCT GGT CCT ACG CTG GTG AAA CCC ACA CAG ACC CTC

CDR1
                                                       ~~~~~~~~~~~~~~~~~~~~
      T   L   T   C   T   F   S   G   F   S   L   S   T   S   G   V   G   V
 55  ACG CTG ACC TGC ACC TTT TCT GGG TTC TCA CTC AGC ACT AGT GGA GTG GGT GTG

CDR1
 ~~~
      G   W   I   R   Q   P   P   G   K   A   L   E   W   L   A   L   I   Y
109  GGC TGG ATC CGT CAG CCC CCA GGA AAG GCC CTG GAG TGG CTT GCA CTC ATT TAT

CDR2
          ~~~~~~~~~~~~~~~~~~~~~~~~~~~~~
      W   D   D   D   K   R   Y   S   P   S   L   K   S   R   L   T   I   T
163  TGG GAT GAT GAT AAG CGC TAC AGT CCA TCT CTG AAG AGC AGG CTC ACC ATC ACC

K   D   T   S   K   N   Q   V   V   L   T   M   A   N   M   D   P   V
217  AAG GAC ACC TCC AAA AAC CAG GTG GTC CTT ACA ATG GCC AAC ATG GAC CCT GTG

CDR3
                                                       ~~~~~~~~~~~~~~~~~~~~
      D   T   A   T   Y   Y   C   A   H   I   R   I   T   E   V   R   G   V
271  GAC ACA GCC ACA TAT TAC TGT GCA CAC ATC CGT ATT ACT GAG GTT CGG GGA GTT

CDR3
     ~~~~~~~~~~~~~~~~~~~~~~~~~~~~
      I   I   S   Y   Y   G   M   D   V   W   G   Q   G   T   T   V   T   V
325  ATT ATC TCC TAC TAC GGT ATG GAC GTC TGG GGC CAA GGG ACC ACG GTC ACC GTC

S   S
379  TCC TCA
```

FIG.4A

Anti-BTLA 6A5 VK

V segment: A27
J segment: JK5

```
      E   I   V   L   T   Q   S   P   G   T   L   S   L   S   P   G   E   R
  1  GAA ATT GTG TTG ACG CAG TCT CCA GGC ACC CTG TCT TTG TCT CCA GGG GAA AGA
```

CDR1
                        ~~~~~~~~~~~~~~~~~~~~~~~~~~~~~~~~~~~~~~~~~~~~~~~~~~
```
      A   T   L   S   C   R   A   S   Q   S   V   S   S   T   Y   L   A   W
 55  GCC ACC CTC TCC TGC AGG GCC AGT CAG AGT GTT AGC AGC ACC TAC TTA GCC TGG
```

CDR2
                                                              ~~~~~~~~~~~~~
```
      Y   Q   Q   K   P   G   Q   A   P   R   L   L   I   Y   G   A   S   S
109  TAC CAG CAG AAA CCT GGC CAG GCT CCC AGG CTC CTC ATC TAT GGT GCA TCC AGC
```

CDR2
     ~~~~~~~~
```
      R   A   T   G   I   P   D   R   F   S   G   S   G   S   G   T   D   F
163  AGG GCC ACT GGC ATC CCA GAC AGG TTC AGT GGC AGT GGG TCT GGG ACA GAC TTC
```

CDR3
                                                                     ~~~~~
```
      T   L   T   I   S   R   L   E   P   E   D   F   A   V   Y   Y   C   Q
217  ACT CTC ACC ATC AGC AGA CTG GAG CCT GAA GAT TTT GCA GTG TAT TAC TGT CAG
```

CDR3
     ~~~~~~~~~~~~~~~~~~~~~~~~~~~~~~~~
```
      Q   Y   G   S   S   P   P   I   T   F   G   Q   G   T   R   L   E   I
271  CAG TAT GGT AGC TCA CCT CCG ATC ACC TTC GGC CAA GGG ACA CGA CTG GAG ATT

K
325  AAA
```

FIG.4B

Anti-BTLA 11E2 VH

V segment: 3-20
D segment: 3-10
J segment: JH6b

```
      E   V   Q   L   V   E   S   G   G   V   I   R   P   G   G   S   L
  1  GAG GTG CAA CTG GTG GAG TCT GGG GGA GGT GTG ATA CGG CCT GGG GGG TCC CTG
```

CDR 1
                                                              ~~~~~~~~~~~~~~~~

```
      R   L   S   C   A   A   S   G   F   T   F   D   D   Y   G   M   S   W
 55  AGA CTC TCC TGT GCA GCC TCT GGA TTC ACC TTT GAT GAT TAT GGC ATG AGC TGG
```

CDR2
                                                              ~~~~~~~~~~~~~~~~

```
      V   R   Q   A   P   G   K   G   L   E   W   V   S   G   I   N   W   N
109  GTC CGC CAA GCT CCA GGG AAG GGG CTG GAG TGG GTC TCT GGT ATT AAT TGG AAT
```

CDR 2
        ~~~~~~~~~~~~~~~~~~~~~~~~~~~~~~~~~~~~~~~~~~~~~~~~~~~~~~

```
      G   G   S   T   G   Y   A   A   S   V   K   G   R   F   T   I   S   R
163  GGT GGT AGC ACA GGT TAT GCA GCC TCT GTG AAG GGC CGA TTC ACC ATC TCC AGA

D   N   A   K   N   S   L   Y   L   Q   M   N   S   L   R   A   E   D
217  GAC AAC GCC AAG AAC TCC CTG TAT CTA CAA ATG AAC AGT CTG AGA GCC GAG GAC
```

CDR3
                                                      ~~~~~~~~~~~~~~~~~~~~~~~~

```
      S   A   L   Y   Y   C   A   R   D   Y   Y   Y   G   P   G   S   P   N
271  TCG GCC TTG TAT TAC TGT GCG AGA GAT TAT TAC TAT GGT CCG GGG AGT CCT AAC
```

CDR3
  ~~~~~~~~~~~~~~~~~~~~~~~~~~~~~~

```
      Y   F   Y   Y   A   M   D   V   W   G   Q   G   T   T   V   T   V   S
325  TAC TTC TAC TAC GCT ATG GAC GTC TGG GGC CAA GGG ACC ACG GTC ACC GTC TCC

S
379  TCA
```

FIG.5A

Anti-BTLA 11E2 VK

V segment:  L15
J segment:  JK1

```
      D   I   Q   M   T   Q   S   P   S   S   L   S   A   S   V   G   D   R
  1  GAC ATC CAG ATG ACC CAG TCT CCA TCC TCA CTG TCT GCA TCT GTA GGA GAC AGA
```

CDR 1
                     ⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯

```
      V   T   I   T   C   R   A   S   Q   G   I   S   S   W   L   A   W   Y
 55  GTC ACC ATC ACT TGT CGG GCG AGT CAG GGT ATT AGC AGC TGG TTA GCC TGG TAT
```

CDR 2
                                                         ⎯⎯⎯⎯⎯⎯⎯⎯⎯⎯⎯⎯

```
      Q   Q   K   P   E   K   A   P   K   S   L   I   Y   A   A   S   S   L
109  CAG CAG AAA CCA GAG AAA GCC CCT AAG TCC CTG ATC TAT GCT GCA TCC AGT TTG
```

CDR 2
⎯⎯⎯⎯⎯

```
      Q   S   G   V   P   S   R   F   S   G   S   G   S   G   T   D   F   T
163  CAA AGT GGG GTC CCA TCA AGG TTC AGC GGC AGT GGA TCT GGG ACA GAT TTC ACT
```

CDR 3
                                                                  ⎯⎯⎯⎯⎯⎯

```
      L   T   I   S   S   L   Q   P   E   D   F   A   T   Y   Y   C   Q   Q
217  CTC ACC ATC AGC AGC CTG CAG CCT GAA GAT TTT GCA ACT TAT TAC TGC CAA CAG
```

CDR 3
      ⎯⎯⎯⎯⎯⎯⎯⎯⎯⎯⎯⎯⎯⎯

```
      Y   N   S   Y   P   R   T   F   G   Q   G   T   K   V   E   I   K
271  TAT AAT AGT TAC CCT CGG ACG TTC GGC CAA GGG ACC AAG GTG GAA ATC AAA
```

FIG. 5B

Anti-BTLA E8D9 VH

V segment:   2-05
D segment:   3-10
J segment:   JH6b

```
      Q   I   T   L   K   E   S   G   P   T   L   V   K   P   T   Q   T   L
  1 CAG ATC ACC TTG AAG GAG TCT GGT CCT ACG CTG GTG AAA CCC ACA CAG ACC CTC
```

CDR1
                                                                        ~~~~~~~~~~~~~~~~~~

```
      T   L   T   C   T   F   S   G   F   S   L   S   T   S   G   V   G   V
 55 ACG CTG ACC TGC ACC TTC TCT GGG TTC TCA CTC AGC ACT AGT GGA GTG GGT GTG
```

CDR1                                                         CDR2
   ~~~                                                          ~~~~~~~~~~~~~~

```
      G   W   I   R   Q   P   P   G   K   A   L   E   W   L   A   L   I   Y
109 GGC TGG ATC CGT CAG CCC CCA GGA AAG GCC CTG GAG TGG CTT GCA CTC ATT TAT
```

CDR2
                   ~~~~~~~~~~~~~~~~~~~~~~~~~~~~~~~~~~~~~~~~~~~

```
      W   D   D   D   K   R   Y   S   P   S   L   K   S   R   L   T   I   T
163 TGG GAT GAT GAT AAG CGC TAC AGC CCA TCT CTG AAG AGC AGG CTC ACC ATC ACC
```

```
      K   D   T   S   K   N   Q   V   V   L   T   M   T   N   M   D   P   V
217 AAG GAC ACC TCC AAA AAC CAG GTG GTC CTT ACA ATG ACC AAC ATG GAC CCT GTG
```

CDR3
                                                        ~~~~~~~~~~~~~~~~~~~~~~~

```
      D   T   A   T   Y   Y   C   A   H   T   S   I   T   E   V   R   G   A
271 GAC ACA GCC ACA TAT TAC TGT GCA CAC ACC AGT ATT ACT GAG GTT CGG GGA GCT
```

CDR3
```
      I   I   Y   Y   Y   G   M   D   V   W   G   Q   G   T   T   V   T   V
325 ATT ATC TAC TAC TAC GGT ATG GAC GTC TGG GGC CAA GGG ACC ACG GTC ACC GTC
```

```
      S   S
379 TCC TCA
```

FIG. 6A

Anti-BTLA E8D9 VK

V segment:   A27
J segment:   JK4

```
      E    I    V    L    T    Q    S    P    G    T    L    S    L    S    P    G    E    R
  1  GAA  ATT  GTG  TTG  ACG  CAG  TCT  CCA  GGC  ACC  CTG  TCT  TTG  TCT  CCA  GGG  GAA  AGA

CDR1
                              ~~~~~~~~~~~~~~~~~~~~~~~~~~~~~~~~~~~~~~~~~~~~~~~
      A    T    L    S    C    R    A    S    Q    S    V    S    S    S    Y    L    A    W
 55  GCC  ACC  CTC  TCC  TGC  AGG  GCC  AGT  CAG  AGT  GTT  AGC  AGC  AGC  TAC  TTA  GCC  TGG

CDR2
                                                                              ~~~~~~~~~~~~~~~
      Y    Q    Q    K    P    G    Q    A    P    R    L    L    I    Y    G    A    S    S
109  TAC  CAG  CAG  AAA  CCT  GGC  CAG  GCT  CCC  AGG  CTC  CTC  ATC  TAT  GGT  GCA  TCC  AGC

CDR2
      ~~~~~~~~~~
      R    A    T    G    I    P    D    R    F    S    G    S    G    S    G    T    D    F
163  AGG  GCC  ACT  GGC  ATC  CCA  GAC  AGG  TTC  AGT  GGC  AGT  GGG  TCT  GGG  ACA  GAG  TTC

CDR3
                                                                                        ~~~
      T    L    T    I    S    R    L    E    P    E    D    F    A    V    Y    Y    C    Q
217  ACT  CTC  ACC  ATC  AGC  AGA  CTG  GAG  CCT  GAA  GAT  TTT  GCA  GTG  TAT  TAC  TGT  CAG

CDR3
      ~~~~~~~~~~~~~~~~~
      Q    Y    G    H    S    L    T    F    G    G    G    T    K    V    E    I    K
271  CAG  TAT  GGT  CAC  TCG  CTC  ACT  TTC  GGC  GGA  GGG  ACC  AAG  GTG  GAG  ATC  AAA
```

FIG.6B

Anti-BTLA 1B4 VH

```
                                                        CDR1
2-05 germline    Q I T L K E S G P T L V K P T Q T L
1B4 VH           - - - - - - - - - - - - - - - - -

2-05 germline    T L T C T F S G F S L S T S G V G V
1B4 VH           - - - - - - - - - - N - I - - - -

2-05 germline    G W I R Q P P G K A L E W L A L I Y
1B4 VH           N - - - - - - - - - - - - - - - -

CDR2
2-05 germline    W N D D K R Y S P S L K S R L T I T
1B4 VH           - D - - - - - - - - - R - - - - S 2-05 germline    K D T S K N Q V V L T M T N M D P V
1B4 VH           - - - - - - - - - - - - - - - - -

CDR3
2-05 germline    D T A T Y Y C A H R
1B4 VH           - - - - - - - - - S G I T E V R G V JH6b germline        Y Y G M D V W G Q G T T V T V
1B4 VH           I I H - - - - - - - - - - - - -

JH6b germline    S S
1B4 VH           - - (JH6b)
```

FIG. 7

Anti-BTLA 1B4 VK

```
                                                              CDR1
A27 germline  E I V L T Q S P G T L S L S P G E R A T L S C R A S Q S V S S
1B4 VK        - - - - - - - - - - - - - - - - - - - - - - - - - - - - - -

CDR2
A27 germline  S Y L A W Y Q Q K P G Q A P R L L I Y G A S S R A T G I P D R
1B4 VK        - - - - - - - - - - - - - - - - - - - - - - - - - - - - - -

CDR3
A27 germline  F S G S G S G T D F T L T I S R L E P E D F A V Y Y C Q Q Y G
1B4 VK        - - - - - - - - - - - - - - - - - - - - - - - - - - - - - -

A27 germline  S S
JK5 germline      I T F G Q G T R L E I K       (JK5)
1B4 VK        - - - - - - - - - - - - - - -
```

FIG.8

Anti-BTLA E4H9 VH region

```
                                                                CDR1
                                                            _____
2-70 germline    Q V T L R E S G P A L V K P T Q T L T L T C T F S G F S L S T S G M C V S W I R Q
E4H9 VH          . . . . . . . . . . . . . . . . . . . . . . . . . . . . . . . . . . . . . . . .

CDR2
                        _____
2-70 germline    P P G K A L E W L A L I D W D D D K Y Y S T S L K T R L T I S K D T S K N Q V V L
E4H9 VH          . . . . . . . . . . . . . . . . . . . V . . . . S . . . . . . . . . . . . . . . .

CDR3
                                         _____
2-70 germline    T M T N M D P V D T A T Y Y C A R I                                   Y Y Y Y Y G M D V W G Q G T T
JH6b germline
E4H9 VH          . . . D . . . . . . . . . . . . . . . R F T M F R G V   Y Y . . . . . . . . . L . . . .

JH6b germline    V T V S S       (JH6b)
E4H9 VH          . . . . .
```

FIG. 9

Anti-BTLA E4H9 VK region

```
                          CDR1
A27 germline    E I V L T Q S P G T L S L S P G E R A T L S C R A S Q S V S S S Y L A W Y Q
E4H9 VK         - - - - - - - - - - - - - - - - - - - - - - - - - - - - - - - - - - - - -

CDR2
A27 germline    Q K P G Q A P R L L I Y G A S S R A T G I P D R F S G S G S G T D F T L T I
E4H9 VK         - - - - - - - - - - - - - - - - - - - - - - - - - - - - - - - - - - - - -

CDR3
A27 germline    S R L E P E D F A V Y Y C Q Q Y G S S P
E4H9 VK         - - - - - - - - - - - - - - - - - - - -         - - - - - - I - - - - - -

JK3 germline                                            T F G P G T K V D I K      (JK3)
E4H9 VK
```

FIG.10

Anti-BTLA 3C2 VH region

```
                                                     CDR1
                                                ─────────────
4-59 germline    Q V Q L Q E S G P G L V K P S E T L S L T C T V S G G S I S S Y Y W S W I R
3C2 VH           - - - - - - - - - - - - - - - - - - - - - - I - - - - - N - - - - N - - -

CDR2
                         ─────────────────────────────
4-59 germline    Q P P G K G L E W I G Y I Y Y S G S T N Y N P S L K S R V T I S V D T S K N
3C2 VH           - - - - - - - - - - - - - - - - T - - - K - - - - - - - - M - - E - - - -

CDR3
                                                        ─────────────────────────
4-59 germline    Q F S L K L S S V T A A D T A V Y Y C A R
JH4b germline                                              F D Y W G Q T
3C2 VH           - - - - - - - - - - - - - - - - - - - - - V K V Y S T G W F   F D Y - - - - -

JH4b germline    L V T V S S                (JH4b)
3C2 VH           - - - - - -
```

FIG. 11

Anti-BTLA 3C2 VK1 region

```
                                                          CDR1
L18 germline    A I Q L T Q S P S S L S A S V G D R V T I T C R A S Q G I S S
3C2 VK1         . . . . . . . . . . . . . . . . . . . . . . . . . . . . . .

CDR2
L18 germline    A L A W Y Q Q K P G K A P K L L I Y D A S S L E S G V P S R F
3C2 VK1         . . . . . . . . . . . . . . . . . . . . . . . . . . . . . .

CDR3
L18 germline    S G S G S G T D F T L T I S S L Q P E D F A T Y Y C Q Q F N S
3C2 VK1         . . . . . . . . . . . . . . . . . . . . . . . . . . . . . .

Y P
L18 germline        L T F G G G T K V E I K    (JK4)
JK4 germline
3C2 VK1         . . . . . . . . . . . . . .
```

FIG. 12

Anti-BTLA 3C2 VK2 region

```
                                              CDR1
A27 germline    E I V L T Q S P G T L S L S P G E R A T L S C R A S Q S V S S S Y L A W
3C2 VK2         - - - - - - - - - - - - - - - - - - - - - - - - - - - - - - - - - - -

CDR2
A27 germline    Y Q Q K P G Q A P R L L I Y G A S S R A T G I P D R F S G S G S G T D F
3C2 VK2         - - - - - - - - - - - - - - - - - - - - - - - - - - - - - - - - - - -

CDR3
A27 germline    T L T I S R L E P E D F A V Y Y C Q Q Y G S S P
3C2 VK2         - - - - - - - - - - - - - - - - - - - - - - - -

A27 germline                                                    Y T F G Q G T K L E I K    (JK2)
JK2 germline
3C2 VK2                                                         - - - - - - - - - - - -
```

FIG. 13

Anti-BTLA 6A5 VH

| | |
|---|---|
| 2-05 germline | Q I T L K E S G P T L V K P T Q T L |
| 6A5 VH        | - - - - - - - - - - - - - - - - - |

_CDR_1_

| | |
|---|---|
| 2-05 germline | T L T C T F S G F S L S T S G V G V |
| 6A5 VH        | - - - - - - - - - - - - - - - - - - |

_CDR_2_

| | |
|---|---|
| 2-05 germline | G W I R Q P P G K A L E W L A L I Y |
| 6A5 VH        | - - - - - - - - - - - - - - - - - - |

___CDR_2_____

| | |
|---|---|
| 2-05 germline | W N D D K R Y S P S L K S R L T I T |
| 6A5 VH        | - D - - - - - - - - - - - - - - - - |

| | |
|---|---|
| 2-05 germline | K D T S K N Q V V L T M T N M D P V |
| 6A5 VH        | - - - - - - - - - - - - - A - - - - |

_CDR_3_

| | |
|---|---|
| 2-05 germline | D T A T Y Y C A H |
| 6A5 VH        | - - - - - - - - - I R I T E V R G V |

| | |
|---|---|
| JH6b germline | Y Y Y G M D V W G Q G T T V T V |
| 6A5 VH        | I I S - - - - - - - - - - - - - |

| | |
|---|---|
| JH6b germline | S S |
| 6A5 VH        | - - (JH6b) |

FIG.14

Anti-BTLA 6A5 VK

```
A27 germline    E I V L T Q S P G T L S L S P G E R A
6A5 VK          - - - - - - - - - - - - - - - - - - -

CDR_1
A27 germline    T L S C R A S Q S V S S S Y L A W Y Q
6A5 VK          - - - - - - - - - - - - - - - - - - -

CDR_2
A27 germline    Q K P G Q A P R L L I Y G A S S R A T
6A5 VK          - - - - - - - - - - - - - - - - - - -

A27 germline    G I P D R F S G S G S G T D F T L T I
6A5 VK          - - - - - - - - - - - - - - - - - - -

CDR_3
A27 germline    S R L E P E D F A V Y Y C Q Q Y G S S
6A5 VK          - - - - - - - - - - - - - - - - - - -

A27 germline    P P
JK5 germline        I T F G Q G T R L E I K
6A5 VK          - - - - - - - - - - - - - -(JK5)
```

FIG.15

Anti-BTLA 11E2 VH

```
                                                              CDR1
3-20 germline    E V Q L V E S G G G V V R P G G S L R L S C A A S G F T F D D Y G M S W
11E2 germline    · · · · · · · · · · · · · · · · · · · · · · · · · · · · · · · · · · ·

CDR2
3-20 germline    V R Q A P G K G L E W V S G I N W N G G S T G Y A D S V K G R F T I S R
11E2 VH          · · · · · · · · · · · · · · · · · · · · · · · A · · · · · · · · · · ·

CDR3
3-20 germline    D N A K N S L Y L Q M N S L R A E D T A L Y H C A R
11E2 VH          · · · · · · · · · · · · · · · · · · · · · · · · · · S · · · Y · · · D Y Y Y G P G S P N JH6b germline    Y Y Y Y G M D V W G Q G T T V T V S S
11E2 VH          · F · · · A · · · · · · · · · · · · · · (JH6b)
```

FIG.16

Anti-BTLA 11E2 VK

```
                                                                CDR1
L15 germline    D I Q M T Q S P S S L S A S V G D R V T I T C R A S Q G I S S
11E2 Vk         · · · · · · · · · · · · · · · · · · · · · · · · · · · · · ·

CDR2
L15 germline    W L A W Y Q Q K P E K A P K S L I Y A A S S L Q S G V P S R F
11E2 Vk         · · · · · · · · · · · · · · · · · · · · · · · · · · · · · ·

CDR3
L15 germline    S G S G S G T D F T L T I S S L Q P E D F A T Y Y C Q Q Y N S
11E2 Vk         · · · · · · · · · · · · · · · · · · · · · · · · · · · · · ·

L15 germline    Y P     T F G Q G T K V E I K
JK1 germline          · ·  - - R - - - - - - - - - - - - - - (JK1)
                    11E2vk
```

FIG. 17

Anti-BTLA E8D9 VH

| | |
|---|---|
| 2-05 germline | Q I T L K E S G P T L V K P T Q T L |
| E8D9 | - - - - - - - - - - - - - - - - - |

_CDR1_____

| | |
|---|---|
| 2-05 germline | T L T C T F S G F S L S T S G V G V |
| E8D9 VH | - - - - - - - - - - - - - - - - - - - |

_CDR2

| | |
|---|---|
| 2-05 germline | G W I R Q P P G K A L E W L A L I Y |
| E8D9VH | - - - - - - - - - - - - - - - - - - |

CDR2_____

| | |
|---|---|
| 2-05 germline | W N D D K R Y S P S L K S R L T I T |
| E8D9 VH | - D - - - - - - - - - - - - - - - - |

| | |
|---|---|
| 2-05 germline | K D T S K N Q V V L T M T N M D P V |
| E8D9 VH | - - - - - - - - - - - - - - - - - - |

_CDR3_____

| | |
|---|---|
| 2-05 germline | D T A T Y Y C A H |
| E8D9 VH | - - - - - - - - - T S I T E V R G A |

| | |
|---|---|
| JH6 germline | Y Y Y G M D V W G Q G T T V T V |
| E8D9 VH | I I - - - - - - - - - - - - - - |

| | |
|---|---|
| JH6 germline | S S |
| E8D9 VH | - - |

FIG.18

Anti-BTLA E8D9 VK

```
                                   CDR1
A27 germline   E I V L T Q S P G T L S L S P G E R A T L S C R A S Q S V S S S Y L A W Y Q Q
E8D9 VK        - - - - - - - - - - - - - - - - - - - - - - - - - - - - - - - - - - - - - -

CDR2
A27 germline   K P G Q A P R L L I Y G A S S R A T G I P D R F S G S G S G T D F T L T I S R
E8D9 VK        - - - - - - - - - - - - - - - - - - - - - - - - - - - - - - - - - - - - - -

CDR3
A27 germline   L E P E D F A V Y Y C Q Q Y G                     L T F G G G T K V E I K
JK4                                         - - - - - - - - - H S                         L T F G G G T K V E I K  (JK4)
E8D9 VK        - - - - - - - - - - - - - - - - - - - - - H S - - - - - - - - - - - - - -
```

FIG. 19

MKTLPAMLGTGKLFWVFFLIPYLDIWNIHGKESCDVQLYIKRQS

EHSILAGDPFELECPVKYCANRPHVTWCKLNGTTCVKLEDRQTSWKEEKNISFFI
LHF

EPVLPNDNGSYRCSANFQSNLIESHSTTLYVTDVKSASERPSKDEMASRPWLLYS
LLP

LGGLPLLITTCFCLFCCLRRHQGKQNELSDTAGREINLVDAHLKSEQTEASTRQN
SQV

LLSETGIYDNDPDLCFRMQEGSEVYSNPCLEENKPGIVYASLNHSVIGLNSRLAR
NVK

EAPTEYASICVRS

FIG. 20

Anti-BTLA 10H6 VH

V segment: 3-33
D segment: 3-10
J segment: JH6b

```
      Q   V   Q   L   V   E   S   G   G   V   V   Q   P   G   R   S   L
  1  CAG GTG CAG CTG GTG GAG TCT GGG GGA GGC GTG GTC CAG CCT GGG AGG TCC CTG
```

CDR1
                                                  ─────────────────────────

```
      R   L   S   C   A   A   S   G   F   T   F   S   S   Y   D   M   H   W
 55  AGA CTC TCC TGT GCA GCG TCT GGA TTC ACC TTC AGT AGC TAT GAC ATG CAC TGG
```

CDR2
                                                              ─────────────

```
      V   R   Q   A   P   G   K   G   L   E   W   V   A   A   I   W   N   D
109  GTC CGC CAG GCT CCA GGC AAG GGG CTG GAG TGG GTG GCA GCT ATA TGG AAT GAT
```

CDR2
       ──────────────────────────────────────

```
      G   S   N   K   Y   Y   A   D   S   V   K   G   R   F   T   I   S   R
163  GGA AGT AAT AAA TAC TAT GCA GAC TCC GTG AAG GGC CGA TTC ACC ATC TCC AGA

D   N   S   K   N   T   L   Y   L   Q   M   N   S   L   R   A   E   D
217  GAC AAT TCC AAG AAC ACG CTG TAT CTG CAA ATG AAC AGC CTG AGA GCC GAG GAC
```

CDR3
                                                  ─────────────────────────

```
      T   A   V   Y   Y   C   A   R   D   R   I   T   M   V   R   G   V   I
271  ACG GCT GTG TAT TAC TGT GCG AGA GAC CGT ATT ACT ATG GTT CGG GGA GTT ATT
```

CDR3
       ───────────────────────

```
      T   Q   Y   Y   G   M   D   V   W   G   Q   G   T   T   V   T   V   S
325  ACC CAA TAC TAC GGT ATG GAC GTC TGG GGC CAA GGG ACC ACG GTC ACC GTC TCC

S
379  TCA
```

FIG.21A

Anti-BTLA 10H6 VH

V segment: 04
J segment: JK2

```
      D   I   Q   L   T   Q   S   P   S   S   L   S   A   S   V   G   D   R
  1  GAC ATC CAG TTG ACC CAG TCT CCA TCC TCC CTG TCT GCA TCT GTA GGA GAC AGA
```

CDR1
                    ─────────────────────────────────────────────
```
      V   T   I   T   C   R   V   S   Q   G   I   S   S   Y   L   N   W   Y
 55  GTC ACC ATC ACT TGC CGG GTG AGT CAG GGC ATT AGC AGT TAT TTA AAT TGG TAT
```

CDR2
                                                  ──────────────────
```
      R   Q   K   P   G   K   V   P   K   L   L   I   Y   S   A   S   N   L
109  CGG CAG AAA CCA GGG AAA GTT CCT AAG CTC CTG ATC TAT AGT GCA TCC AAT TTG
```

CDR2
─────
```
      Q   S   G   V   P   S   R   F   S   G   S   G   S   G   T   D   F   T
163  CAA TCT GGA GTC CCA TCT CGG TTC AGT GGC AGT GGA TCT GGG ACA GAT TTC ACT
```

CDR3
                                                                  ──────
```
      L   T   I   S   S   L   Q   P   E   D   V   A   T   Y   Y   G   Q   R
217  CTC ACT ATC AGC AGC CTG CAG CCT GAA GAT GTT GCA ACT TAT TAC GGT CAA CGG
```

CDR3
        ────────────────────────────
```
      T   Y   N   A   P   Y   T   F   G   Q   G   T   K   L   E   I   K
271  ACT TAC AAT GCC CCG TAC ACT TTT GGC CAG GGG ACC AAG CTG GAG ATC AAA
```

FIG.21B

Anti-BTLA 10H6a VK

V segment: A27
J segment: JK5

```
      E   I   V   L   T   Q   S   P   G   T   L   S   L   S   P   G   E   R
  1  GAA ATT GTG TTG ACG CAG TCT CCA GGC ACC CTG TCT TTG TCT CCA GGG GAA AGA
```

CDR1
                              ------------------------------------------------

```
      A   T   L   S   C   R   A   S   Q   S   V   S   S   I   Y   L   A   W
 55  GCC ACC CTC TCC TGC AGG GCC AGT CAG AGT GTT AGC AGC ATC TAC TTA GCC TGG
```

CDR2
                                                              ------------------

```
      Y   Q   Q   K   P   G   Q   A   P   R   L   L   I   Y   G   A   S   S
109  TAC CAG CAG AAA CCT GGC CAG GCT CCC AGG CTC CTC ATC TAT GGT GCA TCC AGC
```

CDR2
      ----------

```
      R   A   T   G   I   P   D   R   F   S   G   S   G   S   G   T   U   F
163  AGG GCC ACT GGC ATC CCA GAC AGG TTC AGT GGC AGT GGG TCT GGG ACA GAC TTC
```

CDR3
                                                                         ~~~

```
      T   L   T   I   S   R   L   E   P   E   D   F   A   V   Y   Y   C   Q
217  ACT CTC ACC ATC AGC AGA CTG GAG CCT GAA GAT TTT GCA GTG TAT TAC TGT CAG
```

CDR3
      ------------------

```
      Q   Y   G   S   S   P   P   I   T   F   G   Q   G   T   R   L   E   I
271  CAG TAT GGT AGC TCA CCT CCG ATC ACC TTC GGC CAA GGG ACA CGA CTG GAG ATT
```

```
      K
325  AAA
```

FIG.21C

```
                                                              CDR1
Anti-BTLA 10H6 VH 3-33 germline    Q V Q L V E S G G G V V Q P G R S L R L S C A A A S G F T F S S Y G M H W
10H6 VH          - - - - - - - - - - - - - - - - - - - - - - - - - - - - - - - D - - -

CDR2
3-33 germline    V R Q A P G K G L E W V A V I W Y D G S N K Y Y A D S V K G R F T I S R
10H6 VH          - - - - - - - - - - - - - - - A - - - - N - - - - - - - - - - - - - -

CDR3
3-33 germline    D N S K N T L Y L Q M N S L R A E D T A V Y Y C A R - - - - D R I T M V R G V I
10H6 VH          - - - - - - - - - - - - - - - - - - - - - - - - - - - - - D R I T M V R G V I CDR3
JH6b germline    Y Y Y Y G M D V W G Q G T T V T V S S          (JH6b)
10H6 VH          T Q - - - - - - - - - - - - - - - - -
```

FIG. 22

Anti-BTLA 10H6 VK

```
                                              CDR1
04 germline    D I Q L T Q S P S S L S A S V G D R V T I T C R V S Q G I S S
10H6 VK1       - - - - - - - - - - - - - - - - - - - - - - - - - - - - - - -

CDR1                              CDR2
04 germline    Y L N W Y R Q K P G K V P K L L I Y S A S N L Q S G V P S R F
10H6 VK1       - - - - - - - - - - - - - - - - - - - - - - - - - - - - - - -

CDR3
04 germline    S G S G S G T D F T L T I S S L Q P E D V A T Y Y G Q R T Y N
10H6 VK1       - - - - - - - - - - - - - - - - - - - - - - - - - - - - - - -

CDR3
04 germline    A P
JK2 germline        Y T F G Q G T K L E I K   (JK2)
10H6 VK1       - - - - - - - - - - - - - - -
```

FIG.23

Anti-BTLA 10H6a VK

```
A27 germline    E I V L T Q S P G T L S L S P G E R A
10H6 VK2        - - - - - - - - - - - - - - - - - - -

CDR1
A27 germline    T L S C R A S Q S V S S S Y L A W Y Q
10H6 VK2        - - - - - - - - - - - - I - - - - - -

CDR2
A27 germline    Q K P G Q A P R L L I Y G A S S R A T
10H6 VK2        - - - - - - - - - - - - - - - - - - -

A27 germline    G I P D R F S G S G S G T D F T L T I
10H6 VK2        - - - - - - - - - - - - - - - - - - -

CDR3
A27 germline    S R L E P E D F A V Y Y C Q Q Y G S S
10H6 VK2        - - - - - - - - - - - - - - - - - - -

CDR3
A27 germline    P P
JK5 germline        I T F G Q G T R L E I K
10H6 VK2        - - - - - - - - - - - - - (JK5)
```

FIG.24

Anti-BTLA 4C9 VH

V segment:   2-05
D segment:   3-10
J segment:   JH6b

```
     Q   I   T   L   K   E   S   G   P   T   L   V   K   P   T   Q   T   L
  1  CAG ATC ACC TTG AAG GAG TCT GGT CCT ACG CTG GTG AAG CCC ACA CAG ACC CTC

CDR1
                                                                   ─────────────────────
     T   L   T   C   T   F   S   G   F   S   L   S   T   S   G   V   G   V
 55  ACG CTG ACC TGC ACC TTC TCT GGG TTC TCA CTC AGC ACT AGT GGA GTG GGT GTG

CDR1                                                         CDR2
     ~~~                                                          ~~~~~~~~~~~
     A   W   I   R   Q   P   P   G   K   A   L   E   W   L   A   L   I   Y
109  GCC TGG ATC CGT CAG CCC CCA GGA AAG GCC CTG GAG TGG CTT GCA CTC ATT TAT

CDR2
     ~~~~~~~~~~~~~~~~~~~~~~~~~~~~~~~~~~~~~~~~~~~~~~~~~~~
     W   D   D   D   K   R   Y   S   P   S   L   K   S   R   L   T   I   T
163  TGG GAT GAT GAT AAG CGC TAC AGC CCA TCT CTG AAG AGC AGG CTC ACC ATC ACC

K   D   T   S   K   N   Q   V   V   L   T   M   S   N   M   D   P   V
217  AAG GAC ACC TCC AAA AAC CAG GTG GTC CTT ACA ATG AGC AAC ATG GAC CCT GTG

CDR3
                                                      ~~~~~~~~~~~~~~~~~~~~~~
     D   T   A   T   Y   Y   C   A   H   T   R   I   A   E   V   R   G   V
271  GAC ACA GCC ACA TAT TAC TGT GCG CAC ACC CGC ATT GCT GAG GTT CGG GGA GTT

CDR3
     ~~~~~~~~~~~~~~~~~~~~~~~~~~~~~~
     I   Y   Y   Y   Y   G   I   D   V   W   G   Q   G   T   T   V   T   V
325  ATA TAC TAC TAC TAC GGT ATA GAC GTC TGG GGC CAA GGG ACC ACG GTC ACC GTC

S   S
379  TCC TCA
```

FIG.25A

Anti-BTLA 4C9 VK

V segment: A27
D segment: JK1

```
      E   I   V   L   T   Q   S   P   G   T   L   S   L   S   P   G   E   R
  1  GAA ATT GTG TTG ACG CAG TCT CCA GGC ACC CTG TCT TTG TCT CCA GGG GAA AGA

CDR1
                          ~~~~~~~~~~~~~~~~~~~~~~~~~~~~~~~~~~~~~~~~~~~~~~~~~~
      A   T   L   S   C   R   A   S   Q   S   V   S   S   T   Y   L   V   W
 55  GCC ACC CTC TCC TGC AGG GCC AGT CAG AGT GTT AGC AGC ACC TAC TTA GTC TGG

CDR2
                                                                  ~~~~~~~~~~
      Y   Q   Q   K   P   G   Q   A   P   R   L   L   I   Y   G   A   S   S
109  TAC CAG CAG AAA CCT GGC CAG GCT CCC AGG CTC CTC ATC TAT GGT GCA TCC AGC

CDR2
      ~~~~~~~~
      R   A   T   G   I   P   D   R   F   S   G   S   G   S   G   T   D   F
163  AGG GCC ACT GGC ATC CCA GAC AGG TTC AGT GGC AGT GGG TCT GGG ACA GAC TTC

CDR3
                                                                       ~~~
      T   L   T   I   S   R   L   E   P   E   D   F   A   V   Y   Y   C   Q
217  ACT CTC ACC ATC AGC AGA CTG GAG CCT GAA GAT TTT GCA GTG TAT TAC TGT CAG

CDR3
      ~~~~~~~~~~~~~~~~~~~~~~~~~
      Q   Y   G   S   S   W   T   F   G   Q   G   T   K   V   E   I   K
271  CAG TAT GGT AGC TCG TGG ACG TTC GGC CAA GGG ACC AAG GTG GAA ATC AAA
```

FIG. 25B

Anti-BTLA 4C9 VH

```
2-05 germline    Q I T L K E S G P T L V K P T Q T L
4C9 VH           - - - - - - - - - - - - - - - - -

_CDR1_____
2-05 germline    T L T C T F S G F S L S T S G V G V
4C9 VH           - - - - - - - - - - - - - - - - - -

_CDR2
2-05 germline    G W I R Q P P G K A L E W L A L I Y
4C9 VH           A - - - - - - - - - - - - - - - - -

CDR2_____
2-05 germline    W N D D K R Y S P S L K S R L T I T
4C9 VH           - D - - - - - - - - - - - - - - - -

2-05 germline    K D T S K N Q V V L T M T N M D P V
4C9 VH           - - - - - - - - - - - - S - - - - -

_CDR3_____
2-05 germline    D T A T Y Y C A H
4C9 VH           - - - - - - - - - T R I A E V R G V CDR3_____
JH6b germline     Y Y Y Y G M D V W G Q G T T V T V
4C9 VH            I - - - - - I - - - - - - - - - -  (JH6b)
```

FIG.26

Anti-BTLA 4C9 VK

```
                                                           CDR1
A27 germline    E I V L T Q S P G T L S L S L S P G E R A T L S C R A S Q S V S S
4C9 VK          . . . . . . . . . . . . . . . . . . . . . . . . . . . . . . . .

CDR2
A27 germline    S Y L A W Y Q Q K P G Q A P R L L I Y G A S S R A T G I P D R
4C9 VK          T . . V . . . . . . . . . . . . . . . . . . . . . . . . . .

CDR3
A27 germline    F S G S G S G T D F T L T I S R L E P E D F A V Y Y C Q Q Y G
4C9 VK          . . . . . . . . . . . . . . . . . . . . . . . . . . . . . .

CDR3
A27 germline    S S
JK1 germline         W T F G Q G T K V E I K         (JK1)
4C9 VK          . .  . . . . . . . . . . . .
```

FIG. 27

HUMAN MONOCLONAL ANTIBODIES TO BTLA AND METHODS OF USE

CROSS-REFERENCE TO RELATED APPLICATIONS

This application is a National Phase of International Application PCT/US07/084792, filed Nov. 15, 2007, which claim the benefit of U.S. Provisional Application Serial No. 60/866,058, filed Nov. 15, 2006, each of which are herein incorporated by reference in their entirety.

SEQUENCE LISTING

The specification further incorporates by reference the Sequence Listing submitted herewith via EFS on Mar. 8, 2010. Pursuant to 37 C.F.R. §1.52(e)(5), the Sequence Listing text file, identified as 0773750847seqlist.txt, is 49,058 bytes and was created on Mar. 8, 2010. The Sequence Listing, electronically filed herewith, does not extend beyond the scope of the specification and thus does not contain new matter.

BACKGROUND

Positive and negative costimulatory signals play critical roles in the modulation of B and T cell activity, and the molecules that mediate these signals have proven to be effective targets for immunomodulatory agents. Positive costimulation, in addition to T cell receptor (TCR) engagement, is required for optimal activation of naive T cells, whereas negative costimulation is believed to be required for the acquisition of immunologic tolerance to self, as well as the termination of effector T cell functions. Upon interaction with B7.1 or B7.2 on the surface of antigen-presenting cells (APC), CD28, the prototypic T cell costimulatory molecule, emits signals that promote T cell proliferation and differentiation in response to TCR engagement, while the CD28 homologue cytotoxic T lymphocyte antigen-4 (CTLA-4) mediates inhibition of T cell proliferation and effector functions (Chambers et al., Ann. Rev. Immunol., 19:565-594, 2001; Egen et al., Nature Immunol., 3:611-618, 2002).

Several new molecules with homology to the B7 family have been discovered (Abbas et al., Nat. Med., 5:1345-6, 1999; Coyle et al., Nat. Immunol., 2: 203-9, 2001; Carreno et al., Annu. Rev. Immunol., 20: 29-53, 2002; Liang et al., Curr. Opin. Immunol., 14: 384-90, 2002), and their role in T cell activation is just beginning to be elucidated. These new costimulatory ligands include B7h, PD-L1, PD-L2, and B7-H3.

B7h (Swallow et al., Immunity, 11: 423-32, 1999), also known as B7RP-1 (Yoshinaga et al., Nature, 402: 827-32, 1999), GL50 (Ling, et al., J. Immunol., 164:1653-7, 2000), B7H2 (Wang et al., Blood, 96: 2808-13, 2000), and LICOS (Brodie et al., Curr. Biol., 10: 333-6, 2000), binds to an inducible costimulator (ICOS) on activated T cells, and costimulates T cell proliferation and production of cytokines such as interleukin 4 (IL-4) and IL-10.

PD-L1 (Freeman et al., J. Exp. Med., 192: 1027-34, 2000), also known as B7-H1 (Dong et al., Nat. Med., 5, 1365-9, 1999), and PD-L2 (Latchman et al., Nat. Immunol., 2:261-8, 2001), also known as B7-DC (Tseng et al., J. Exp. Med., 193, 839-46, 2001) bind to programmed death 1 (PD-1) receptor on T and B cells.

Finally, B7-H3 binds an as yet currently unknown counter-receptor on activated T cells, and is reported to enhance proliferation of CD4+ T helper (Th) cells and CD8+ cytotoxic T lymphocytes (CTLs or Tcs) and selectively enhance IFN-γ expression (Chapoval et al., Nat. Immunol., 2, 269-74, 2001; Sun et al., J. Immunol., 168, 6294-7, 2002). B7-H3 has also been reported to be a negative regulator (Suh et al., Nat. Immunol., 4, 899-906, 2003; Prasad et al., J. Immunol., 173, 2500-2506, 2004). B7-H3 has also been reported to be a negative regulator (Suh et al., Nat. Immunol., 4, 899-906, 2003; Prasad et al., J. Immunol., 173, 2500-2506, 2004).

The identification of additional molecules that have T cell costimulatory activity is of keen interest due to their fundamental biological importance and the therapeutic potential of agents capable of affecting their activity. Agents capable of modulating costimulatory signals, and thereby capable of modulating the activation and/or effector functions of CD8+ CTLs and CD4+ Th cells find use in the modulation of immune responses, and are highly desirable.

In particular, many autoimmune disorders are known to involve autoreactive T cells and autoantibodies. Agents that are capable of inhibiting or eliminating autoreactive lymphocytes without compromising the immune system's ability to defend against pathogens are highly desirable.

Conversely, many cancer immunotherapies, such as adoptive immunotherapy, expand tumor-specific T cell populations and direct them to attack and kill tumor cells (Dudley et al., Science 298:850-854, 2002; Pardoll, Nature Biotech., 20:1207-1208, 2002; Egen et al., Nature Immunol., 3:611-618, 2002). Agents capable of augmenting tumor attack are highly desirable.

In addition, immune responses to many different antigens (e.g., microbial antigens or tumor antigens), while detectable, are frequently of insufficient magnitude to afford protection against a disease process mediated by agents (e.g., infectious microorganisms or tumor cells) expressing those antigens. It is often desirable to administer to the subject, in conjunction with the antigen, an adjuvant that serves to enhance the immune response to the antigen in the subject.

It is also desirable to inhibit normal immune responses to antigen under certain circumstances. For example, the suppression of normal immune responses in a patient receiving a transplant is desirable, and agents that exhibit such immunosuppressive activity are highly desirable.

Costimulatory signals, particularly positive costimulatory signals, also play a role in the modulation of B cell activity. For example, B cell activation and the survival of germinal center B cells require T cell-derived signals in addition to stimulation by antigen. CD40 ligand present on the surface of helper T cells interacts with CD40 on the surface of B cells, and mediates many such T-cell dependent effects in B cells.

The protein BTLA (B and T lymphocyte attenuator) is a member of the CD28 family of receptors that also includes CD28, CTLA-4, ICOS, and PD-1. The initial members of the family, CD28 and ICOS, were discovered by functional effects on augmenting T cell proliferation following the addition of monoclonal antibodies (Hutloff et al. (1999) *Nature* 397:263-266; Hansen et al. (1980) *Immunogenics* 10:247-260). BTLA was discovered through screening for differential expression in TH1 cells. In addition, BTLA has been described as providing negative stimulatory signals, analogous to CTLA-4. In the presence of agonist anti-BTLA mAb, anti-CD3 and anti-CD28 activated T-cells show reduced IL-2 production and proliferation (Kreig et al., *J. Immunol.*, 175, 6420-6472, 2005). Mice lacking an intact BTLA gene show higher titers to DNP-KLH post-immunization and an increased sensitivity to EAE (Watanabe et al., *Nat. Immunol.*, 4, 670-679, 2003). HVEM (herpes virus entry mediator) is thought to be a ligand for BTLA (Scully et al. (2005) *Nat. Immunol.* 6:90-98; Gonzalez et al. (2005) *Proc. Nat'l. Acad. Sci. U.S.A.* 102: 1116-1121).

Accordingly, agents that recognize BTLA, and methods of using such agents, are desired.

SUMMARY

The present disclosure provides isolated monoclonal antibodies, in particular human monoclonal antibodies, that bind to BTLA and that exhibit numerous desirable properties. These properties include, for example, high affinity binding to human BTLA, but lacking substantial cross-reactivity with human CD28, CTLA-4, PD-1, or ICOS. Still further, antibodies of the disclosure have been shown to modulate immune responses. Accordingly, another aspect of the disclosure pertains to methods of modulating immune responses using anti-BTLA antibodies. In particular, the disclosure provides a method of stimulating a T-cell response. Also, the disclosure provides a method of inhibiting growth of tumor cells in vivo using anti-BTLA antibodies.

In one aspect, the disclosure pertains to an isolated monoclonal antibody, or an antigen-binding portion thereof, wherein the antibody exhibits at least one of the following properties:
 (a) binds to human BTLA with a $K_D$ of $1 \times 10^{-7}$ M or less;
 (b) does not substantially bind to human TrkB, CD28, CTLA-4, PD-1 or ICOS;
 (c) inhibits the binding of HVEM to BTLA.
In some embodiments the antibody further:
 (a) stimulates T-cell response;
 (b) stimulates antibody responses;
 (c) inhibits tumor cell growth in vivo.
Preferably the antibody is a human antibody, although in alternative embodiments the antibody can be, for example, a murine antibody, a chimeric antibody or humanized antibody.

In more preferred embodiments, the antibody binds to human BTLA with a $K_D$ of $5 \times 10^{-8}$ M or less, binds to human BTLA with a $K_D$ of $1 \times 10^{-8}$ M or less, binds to human BTLA with a $K_D$ of $5 \times 10^{-9}$ M or less, or binds to human BTLA with a $K_D$ of between $1 \times 10^{-8}$ M and $1 \times 10^{-10}$ M.

In another embodiment, the disclosure provides an isolated monoclonal antibody, or antigen binding portion thereof, wherein the antibody cross-competes for binding to BTLA with a reference antibody comprising:
 (a) a human heavy chain variable region comprises an amino acid sequence selected from the group consisting of SEQ ID NOs: 1, 2, 3, 4, 5, 6, 74, and 85; and
 (b) a human light chain variable region comprises an amino acid sequence selected from the group consisting of SEQ ID NOs: 7, 8, 9, 10, 11, 12, 13, 75, 76, and 86.
In various embodiments, the reference antibody comprises:
 (a) a heavy chain variable region comprising the amino acid sequence of SEQ ID NO:1; and
 (b) a light chain variable region comprising the amino acid sequence of SEQ ID NO:7;
or the reference antibody comprises:
 (a) a heavy chain variable region comprising the amino acid sequence of SEQ ID NO: 2; and
 (b) a light chain variable region comprising the amino acid sequence of SEQ ID NO: 8;
or the reference antibody comprises:
 (a) a heavy chain variable region comprising the amino acid sequence of SEQ ID NO: 3; and
 (b) a light chain variable region comprising the amino acid sequence of SEQ ID NO: 9;
or the reference antibody comprises:
 (a) a heavy chain variable region comprising the amino acid sequence of SEQ ID NO: 3; and
 (b) a light chain variable region comprising the amino acid sequence of SEQ ID NO: 10;
or the reference antibody comprises:
 (a) a heavy chain variable region comprising the amino acid sequence of SEQ ID NO: 4; and
 (b) a light chain variable region comprising the amino acid sequence of SEQ ID NO: 11;
or the reference antibody comprises:
 (a) a heavy chain variable region comprising the amino acid sequence of SEQ ID NO: 5; and
 (b) a light chain variable region comprising the amino acid sequence of SEQ ID NO: 12;
or the reference antibody comprises:
 (a) a heavy chain variable region comprising the amino acid sequence of SEQ ID NO: 6; and
 (b) a light chain variable region comprising the amino acid sequence of SEQ ID NO: 13;
or the reference antibody comprises:
 (a) a heavy chain variable region comprising the amino acid sequence of SEQ ID NO: 74; and
 (b) a light chain variable region comprising the amino acid sequence of SEQ ID NO: 75;
or the reference antibody comprises:
 (a) a heavy chain variable region comprising the amino acid sequence of SEQ ID NO: 74; and
 (b) a light chain variable region comprising the amino acid sequence of SEQ ID NO: 76;
or the reference antibody comprises:
 (a) a heavy chain variable region comprising the amino acid sequence of SEQ ID NO: 85; and
 (b) a light chain variable region comprising the amino acid sequence of SEQ ID NO: 86.

In another aspect, the disclosure pertains to an isolated monoclonal antibody, or an antigen-binding portion thereof, comprising a heavy chain variable region that is the product of or derived from a human $V_H$ 2-05 gene, wherein the antibody specifically binds BTLA. The disclosure further provides an isolated monoclonal antibody, or an antigen-binding portion thereof, comprising a heavy chain variable region that is the product of or derived from a human $V_H$ 2-70 gene, wherein the antibody specifically binds BTLA. The disclosure further provides an isolated monoclonal antibody, or an antigen-binding portion thereof, comprising a heavy chain variable region that is the product of or derived from a human $V_H$ 4-59 gene, wherein the antibody specifically binds BTLA. The disclosure further provides an isolated monoclonal antibody, or an antigen-binding portion thereof, comprising a heavy chain variable region that is the product of or derived from a human $V_H$ 3-20 gene, wherein the antibody specifically binds BTLA. The disclosure further provides an isolated monoclonal antibody, or an antigen-binding portion thereof, comprising a heavy chain variable region that is the product of or derived from a human $V_H$ 3-33 gene, wherein the antibody specifically binds BTLA. The disclosure further provides an isolated monoclonal antibody, or an antigen-binding portion thereof, comprising a light chain variable region that is the product of or derived from a human $V_K$ A27 gene, wherein the antibody specifically binds BTLA. The disclosure further provides an isolated monoclonal antibody, or an antigen-binding portion thereof, comprising a light chain variable region that is the product of or derived from a human $V_K$ L18 gene, wherein the antibody specifically binds BTLA. The disclosure further provides an isolated monoclonal antibody, or an antigen-binding portion thereof, comprising a light chain variable region that is the product of or derived from a human V$_K$ L15 gene, wherein the antibody specifically binds BTLA. The disclosure further provides an isolated monoclonal antibody, or an antigen-binding portion thereof, comprising a light chain variable region that is the product of or derived from a human V$_K$ 04 gene, wherein the antibody specifically binds BTLA.

In a preferred embodiment, the disclosure provides an isolated monoclonal antibody, or an antigen-binding portion thereof, comprising:
(a) a heavy chain variable region of a human V$_H$ 2-05 gene; and
(b) a light chain variable region of a human V$_K$ A27 gene; wherein the antibody specifically binds to BTLA.

In another preferred embodiment, the disclosure provides an isolated monoclonal antibody, or an antigen-binding portion thereof, comprising:
(a) a heavy chain variable region of a human V$_H$ 2-70 gene; and
(b) a light chain variable region of a human V$_K$ A27 gene; wherein the antibody specifically binds to BTLA.

In another preferred embodiment, the disclosure provides an isolated monoclonal antibody, or an antigen-binding portion thereof, comprising:
(a) a heavy chain variable region of a human V$_H$ 4-59 gene; and
(b) a light chain variable region of a human V$_K$ L18 gene; wherein the antibody specifically binds to BTLA.

In another preferred embodiment, the disclosure provides an isolated monoclonal antibody, or an antigen-binding portion thereof, comprising:
(a) a heavy chain variable region of a human V$_H$ 4-59 gene; and
(b) a light chain variable region of a human V$_K$ A27 gene; wherein the antibody specifically binds to BTLA.

In another preferred embodiment, the disclosure provides an isolated monoclonal antibody, or an antigen-binding portion thereof, comprising:
(a) a heavy chain variable region of a human V$_H$ 3-20 gene; and
(b) a light chain variable region of a human V$_K$ L15 gene; wherein the antibody specifically binds to BTLA.

In another preferred embodiment, the disclosure provides an isolated monoclonal antibody, or an antigen-binding portion thereof, comprising:
(a) a heavy chain variable region of a human V$_H$ 3-33 gene; and
(b) a light chain variable region of a human V$_K$ 04 gene; wherein the antibody specifically binds to BTLA.

In another preferred embodiment, the disclosure provides an isolated monoclonal antibody, or an antigen-binding portion thereof, comprising:
(a) a heavy chain variable region of a human V$_H$ 3-33 gene; and
(b) a light chain variable region of a human V$_K$ A27 gene; wherein the antibody specifically binds to BTLA.

In another preferred embodiment, the disclosure provides an isolated monoclonal antibody, or an antigen-binding portion thereof, comprising:
(a) a heavy chain variable region of a human V$_H$ 2-05 gene; and
(b) a light chain variable region of a human V$_K$ A27 gene;

In another aspect, the disclosure provides an isolated monoclonal antibody, or antigen binding portion thereof, comprising:
a heavy chain variable region that comprises CDR1, CDR2, and CDR3 sequences; and a light chain variable region that comprises CDR1, CDR2, and CDR3 sequences,
wherein:
(a) the heavy chain variable region CDR3 sequence comprises an amino acid sequence selected from the group consisting of SEQ ID NOs: 26, 27, 28, 29, 30, 31, 79, and 89, and conservative modifications thereof;
(b) the light chain variable region CDR3 sequence comprises an amino acid sequence selected from the group consisting of SEQ ID NOs: 46, 47, 48, 49, 50, 51, 52, 82, 92, and 97, and conservative modifications thereof; and
(c) the antibody specifically binds to human BTLA.

Preferably, the heavy chain variable region CDR2 sequence comprises an amino acid sequence selected from the group consisting of amino acid sequences of SEQ ID NOs: 20, 21, 22, 23, 24, 25, 78, and 88, and conservative modifications thereof; and the light chain variable region CDR2 sequence comprises an amino acid sequence selected from the group consisting of amino acid sequences of SEQ ID NOs: 39, 40, 41, 42, 43, 44, 45, 81, 91, and 96, and conservative modifications thereof. Preferably, the heavy chain variable region CDR1 sequence comprises an amino acid sequence selected from the group consisting of amino acid sequences of SEQ ID NOs: 14, 15, 16, 17, 18, 19, 77, and 87, and conservative modifications thereof; and the light chain variable region CDR1 sequence comprises an amino acid sequence selected from the group consisting of amino acid sequences of SEQ ID NOs: 32, 33, 34, 35, 36, 37, 38, 80, 90, and 95, and conservative modifications thereof.

In yet another aspect, the disclosure provides an isolated monoclonal antibody, or antigen binding portion thereof, comprising a heavy chain variable region and a light chain variable region, wherein:
(a) the heavy chain variable region comprises an amino acid sequence that is at least 80% homologous to an amino acid sequence selected from the group consisting of SEQ ID NOs: 1, 2, 3, 4, 5, 6, 74, and 85;
(b) the light chain variable region comprises an amino acid sequence that is at least 80% homologous to an amino acid sequence selected from the group consisting of SEQ ID NOs: 7, 8, 9, 10, 11, 12, 13, 75, 76, and 86;
(c) the antibody binds to human BTLA with a K$_D$ of $1 \times 10^{-7}$ M or less; and
(d) the antibody does not substantially bind to human TrkB, PD-1, CD28, CTLA-4 or ICOS.

In a preferred embodiment, the antibodies additionally inhibit binding of one or more BTLA ligands (e.g. HVEM) to BTLA.

Additionally or alternatively, the antibody may comprise one or more of the other features listed above.

In preferred embodiments, the disclosure provides an isolated monoclonal antibody, or antigen binding portion thereof, comprising:
(a) a heavy chain variable region CDR1 comprising an amino acid sequence selected from the group consisting of SEQ ID NOs: 14, 15, 16, 17, 18, 19, 77, and 87;
(b) a heavy chain variable region CDR2 comprising an amino acid sequence selected from the group consisting of SEQ ID NOs: 20, 21, 22, 23, 24, 25, 78, and 88;
(c) a heavy chain variable region CDR3 comprising an amino acid sequence selected from the group consisting of SEQ ID NOs: 26, 27, 28, 29, 30, 31, 79, and 89;
(d) a light chain variable region CDR1 comprising an amino acid sequence selected from the group consisting of SEQ ID NOs: 32, 33, 34, 35, 36, 37, 38, 80, 90, and 95;

(e) a light chain variable region CDR2 comprising an amino acid sequence selected from the group consisting of SEQ ID NOs: 39, 40, 41, 42, 43, 44, 45, 81, 91, and 96; and (f) a light chain variable region CDR3 comprising an amino acid sequence selected from the group consisting of SEQ ID NOs: 46, 47, 48, 49, 50, 51, 52, 82, 92, and 97;

wherein the antibody specifically binds BTLA.

A preferred combination comprises:
(a) a heavy chain variable region CDR1 comprising SEQ ID NO: 14;
(b) a heavy chain variable region CDR2 comprising SEQ ID NO: 20;
(c) a heavy chain variable region CDR3 comprising SEQ ID NO: 26;
(d) a light chain variable region CDR1 comprising SEQ ID NO: 32;
(e) a light chain variable region CDR2 comprising SEQ ID NO: 39; and
(f) a light chain variable region CDR3 comprising SEQ ID NO: 46.

Another preferred combination comprises:
(a) a heavy chain variable region CDR1 comprising SEQ ID NO: 15;
(b) a heavy chain variable region CDR2 comprising SEQ ID NO: 21;
(c) a heavy chain variable region CDR3 comprising SEQ ID NO: 27;
(d) a light chain variable region CDR1 comprising SEQ ID NO: 33;
(e) a light chain variable region CDR2 comprising SEQ ID NO: 40; and
(f) a light chain variable region CDR3 comprising SEQ ID NO: 47.

Another preferred combination comprises:
(a) a heavy chain variable region CDR1 comprising SEQ ID NO: 16;
(b) a heavy chain variable region CDR2 comprising SEQ ID NO: 22;
(c) a heavy chain variable region CDR3 comprising SEQ ID NO: 28;
(d) a light chain variable region CDR1 comprising SEQ ID NO: 34;
(e) a light chain variable region CDR2 comprising SEQ ID NO: 41; and
(f) a light chain variable region CDR3 comprising SEQ ID NO: 48.

Another preferred combination comprises:
(a) a heavy chain variable region CDR1 comprising SEQ ID NO: 16;
(b) a heavy chain variable region CDR2 comprising SEQ ID NO: 22;
(c) a heavy chain variable region CDR3 comprising SEQ ID NO: 28;
(d) a light chain variable region CDR1 comprising SEQ ID NO: 35;
(e) a light chain variable region CDR2 comprising SEQ ID NO: 42; and
(f) a light chain variable region CDR3 comprising SEQ ID NO: 49.

Another preferred combination comprises:
(a) a heavy chain variable region CDR1 comprising SEQ ID NO: 17;
(b) a heavy chain variable region CDR2 comprising SEQ ID NO: 23;
(c) a heavy chain variable region CDR3 comprising SEQ ID NO: 29;
(d) a light chain variable region CDR1 comprising SEQ ID NO: 36;
(e) a light chain variable region CDR2 comprising SEQ ID NO: 43; and
(f) a light chain variable region CDR3 comprising SEQ ID NO: 50.

Another preferred combination comprises:
(a) a heavy chain variable region CDR1 comprising SEQ ID NO: 18;
(b) a heavy chain variable region CDR2 comprising SEQ ID NO: 24;
(c) a heavy chain variable region CDR3 comprising SEQ ID NO: 30;
(d) a light chain variable region CDR1 comprising SEQ ID NO: 37;
(e) a light chain variable region CDR2 comprising SEQ ID NO: 44; and
(f) a light chain variable region CDR3 comprising SEQ ID NO: 51.

Another preferred combination comprises:
(a) a heavy chain variable region CDR1 comprising SEQ ID NO: 19;
(b) a heavy chain variable region CDR2 comprising SEQ ID NO: 25;
(c) a heavy chain variable region CDR3 comprising SEQ ID NO: 31;
(d) a light chain variable region CDR1 comprising SEQ ID NO: 38;
(e) a light chain variable region CDR2 comprising SEQ ID NO: 45; and
(f) a light chain variable region CDR3 comprising SEQ ID NO: 52.

Another preferred combination comprises:
(a) a heavy chain variable region CDR1 comprising SEQ ID NO: 77;
(b) a heavy chain variable region CDR2 comprising SEQ ID NO: 78;
(c) a heavy chain variable region CDR3 comprising SEQ ID NO: 79;
(d) a light chain variable region CDR1 comprising SEQ ID NO: 80;
(e) a light chain variable region CDR2 comprising SEQ ID NO: 81; and
(f) a light chain variable region CDR3 comprising SEQ ID NO: 82.

Another preferred combination comprises:
(a) a heavy chain variable region CDR1 comprising SEQ ID NO: 87;
(b) a heavy chain variable region CDR2 comprising SEQ ID NO: 88;
(c) a heavy chain variable region CDR3 comprising SEQ ID NO: 89;
(d) a light chain variable region CDR1 comprising SEQ ID NO: 90;
(e) a light chain variable region CDR2 comprising SEQ ID NO: 91; and
(f) a light chain variable region CDR3 comprising SEQ ID NO: 92.

Another preferred combination comprises:
(a) a heavy chain variable region CDR1 comprising SEQ ID NO: 77;
(b) a heavy chain variable region CDR2 comprising SEQ ID NO: 78;
(c) a heavy chain variable region CDR3 comprising SEQ ID NO: 79;
(d) a light chain variable region CDR1 comprising SEQ ID NO: 95;

(e) a light chain variable region CDR2 comprising SEQ ID NO: 96; and (f) a light chain variable region CDR3 comprising SEQ ID NO: 97.

Other preferred antibodies of the disclosure, or antigen binding portions thereof, comprise:

(a) a heavy chain variable region comprising an amino acid sequence selected from the group consisting of SEQ ID NOs: 1, 2, 3, 4, 5, 6, 74, and 85; and (b) a light chain variable region comprising an amino acid sequence selected from the group consisting of SEQ ID NOs: 7, 8, 9, 10, 11, 12, 13, 75, 76, and 86;

wherein the antibody specifically binds BTLA.

A preferred combination comprises:

(a) a heavy chain variable region comprising the amino acid sequence of SEQ ID NO: 1; and (b) a light chain variable region comprising the amino acid sequence of SEQ ID NO: 7

Another preferred combination comprises:

(a) a heavy chain variable region comprising the amino acid sequence of SEQ ID NO: 2; and (b) a light chain variable region comprising the amino acid sequence of SEQ ID NO: 8.

Another preferred combination comprises:

(a) a heavy chain variable region comprising the amino acid sequence of SEQ ID NO: 3; and (b) a light chain variable region comprising the amino acid sequence of SEQ ID NO: 9.

Another preferred combination comprises:

(a) a heavy chain variable region comprising the amino acid sequence of SEQ ID NO: 3; and (b) a light chain variable region comprising the amino acid sequence of SEQ ID NO: 10.

Another preferred combination comprises:

(a) a heavy chain variable region comprising the amino acid sequence of SEQ ID NO: 4; and (b) a light chain variable region comprising the amino acid sequence of SEQ ID NO: 11.

Another preferred combination comprises:

(a) a heavy chain variable region comprising the amino acid sequence of SEQ ID NO: 5; and (b) a light chain variable region comprising the amino acid sequence of SEQ ID NO: 12.

Another preferred combination comprises:

(a) a heavy chain variable region comprising the amino acid sequence of SEQ ID NO: 6; and (b) a light chain variable region comprising the amino acid sequence of SEQ ID NO: 13.

Another preferred combination comprises:

(a) a heavy chain variable region comprising the amino acid sequence of SEQ ID NO: 74; and (b) a light chain variable region comprising the amino acid sequence of SEQ ID NO: 75.

Another preferred combination comprises:

(a) a heavy chain variable region comprising the amino acid sequence of SEQ ID NO: 74; and (b) a light chain variable region comprising the amino acid sequence of SEQ ID NO: 76.

Another preferred combination comprises:

(a) a heavy chain variable region comprising the amino acid sequence of SEQ ID NO: 85; and (b) a light chain variable region comprising the amino acid sequence of SEQ ID NO: 86.

The antibodies of the disclosure can be, for example, full-length antibodies, for example of an IgG1 or IgG4 isotype. Alternatively, the antibodies can be antibody fragments, such as Fab or Fab'2 fragments, or single chain antibodies.

The disclosure also provides an immunoconjugate comprising an antibody of the disclosure, or antigen-binding portion thereof, linked to a therapeutic agent, such as a cytotoxin or a radioactive isotope. The disclosure also provides a bispecific molecule comprising an antibody, or antigen-binding portion thereof, of the disclosure, linked to a second functional moiety having a different binding specificity than said antibody, or antigen binding portion thereof.

Compositions comprising an antibody, or antigen-binding portion thereof, or immunoconjugate or bispecific molecule of the disclosure, and a pharmaceutically acceptable carrier, are also provided.

Nucleic acid molecules encoding the antibodies, or antigen-binding portions thereof, of the disclosure are also encompassed by the disclosure, as well as expression vectors comprising such nucleic acids and host cells comprising such expression vectors. Moreover, the disclosure provides a transgenic mouse comprising human immunoglobulin heavy and light chain transgenes, wherein the mouse expresses an antibody of the disclosure, as well as hybridomas prepared from such a mouse, wherein the hybridoma produces the antibody of the disclosure.

In yet another aspect, the disclosure provides a method of modulating an immune response in a subject comprising administering to the subject the antibody, or antigen-binding portion thereof, of the disclosure such that the immune response in the subject is modulated. Preferably, the antibody of the disclosure enhances, stimulates or increases the immune response in the subject. In some embodiments, the antibody of the invention inhibits, reduces or suppresses the immune response in the subject.

In a further aspect, the disclosure provides a method of inhibiting growth of tumor cells in a subject, comprising administering to a subject a therapeutically effective amount of an anti-BTLA antibody, or antigen-binding portion thereof. The antibodies of the disclosure are preferred for use in the method although other anti-BTLA antibodies can be used instead (or in combination with an anti-BTLA antibody of the disclosure). For example, a chimeric, humanized or fully human anti-BTLA antibody can be used in the method of inhibiting tumor growth.

In a further aspect, the disclosure provides a method of treating an infectious disease in a subject, comprising administering to a subject a therapeutically effective amount of an anti-BTLA antibody, or antigen-binding portion thereof. The antibodies of the disclosure are preferred for use in the method although other anti-BTLA antibodies can be used instead (or in combination with an anti-BTLA antibody of the disclosure). For example, a chimeric, humanized or fully human anti-BTLA antibody can be used in the method of treating an infectious disease.

Still further, the disclosure provides a method of enhancing an immune response to an antigen in a subject, comprising administering to the subject: (i) the antigen; and (ii) an anti-BTLA antibody, or antigen-binding portion thereof, such that an immune response to the antigen in the subject is enhanced. The antigen can be, for example, a tumor antigen, a viral antigen, a bacterial antigen or an antigen from a pathogen. The antibodies of the disclosure are preferred for use in the method although other anti-BTLA antibodies can be used instead (or in combination with an anti-BTLA antibody of the disclosure). For example, a chimeric, humanized or fully human anti-BTLA antibody can be used in the method of enhancing an immune response to an antigen in a subject.

The disclosure also provides methods for making "second generation" anti-BTLA antibodies based on the sequences of the anti-BTLA antibodies provided herein. For example, the disclosure provides a method for preparing an anti-BTLA antibody comprising:

(a) providing: (i) a heavy chain variable region antibody sequence comprising a CDR1 sequence that is selected from the group consisting of SEQ ID NOs: 14, 15, 16, 17, 18, 19, 77, and 87, and/or a CDR2 sequence that is selected from the group consisting of SEQ ID NOs: 20, 21, 22, 23, 24, 25, 78, and 88; and/or a CDR3 sequence that is selected from the group consisting of SEQ ID NOs: 26, 27, 28, 29, 30, 31, 79, and 89; or (ii) a light chain variable region antibody sequence comprising a CDR1 sequence that is selected from the group consisting of SEQ ID NOs: 32, 33, 34, 35, 36, 37, 38, 80, 90, and 95, and/or a CDR2 sequence that is selected from the group consisting of SEQ ID NOs: 39, 40, 41, 42, 43, 44, 45, 81, 91, and 96, and/or a CDR3 sequence that is selected from the group consisting of SEQ ID NOs: 46, 47, 48, 49, 50, 51, 52, 82, 92, and 97;

(b) altering at least one amino acid residue within at least one variable region antibody sequence, said sequence being selected from the heavy chain variable region antibody sequence and the light chain variable region antibody sequence, to create at least one altered antibody sequence; and (c) expressing the altered antibody sequence as a protein.

Other features and advantages of the instant disclosure will be apparent from the following detailed description and examples which should not be construed as limiting. The contents of all references, Genbank entries, patents and published patent applications cited throughout this application are expressly incorporated herein by reference.

BRIEF DESCRIPTION OF THE DRAWINGS

FIG. 1A shows the nucleotide sequence (SEQ ID NO: 53) and amino acid sequence (SEQ ID NO: 1) of the heavy chain variable region of the 1B4 human monoclonal antibody. The CDR1 (SEQ ID NO: 14), CDR2 (SEQ ID NO: 20) and CDR3 (SEQ ID NO: 26) regions are delineated and the V, D and J germline derivations are indicated.

FIG. 1B shows the nucleotide sequence (SEQ ID NO: 59) and amino acid sequence (SEQ ID NO: 7) of the light chain variable region of the 1B4 human monoclonal antibody. The CDR1 (SEQ ID NO: 32), CDR2 (SEQ ID NO: 39) and CDR3 (SEQ ID NO: 46) regions are delineated and the V and J germline derivations are indicated.

FIG. 2A shows the nucleotide sequence (SEQ ID NO: 54) and amino acid sequence (SEQ ID NO: 2) of the heavy chain variable region of the E4H9 human monoclonal antibody. The CDR1 (SEQ ID NO: 15), CDR2 (SEQ ID NO: 21) and CDR3 (SEQ ID NO: 27) regions are delineated and the V and J germline derivations are indicated.

FIG. 2B shows the nucleotide sequence (SEQ ID NO: 60) and amino acid sequence (SEQ ID NO: 8) of the light chain variable region of the E4H9 human monoclonal antibody. The CDR1 (SEQ ID NO: 33), CDR2 (SEQ ID NO: 40) and CDR3 (SEQ ID NO: 46) regions are delineated and the V and J germline derivations are indicated.

FIG. 3A shows the nucleotide sequence (SEQ ID NO: 55) and amino acid sequence (SEQ ID NO: 3) of the heavy chain variable region of the 3C2 human monoclonal antibody. The CDR1 (SEQ ID NO: 16), CDR2 (SEQ ID NO: 22) and CDR3 (SEQ ID NO: 28) regions are delineated and the V and J germline derivations are indicated.

FIG. 3B shows the nucleotide sequence (SEQ ID NO: 61) and amino acid sequence (SEQ ID NO: 9) of the light chain variable region of the 3C2 human monoclonal antibody. The CDR1 (SEQ ID NO: 34), CDR2 (SEQ ID NO: 41) and CDR3 (SEQ ID NO: 48) regions are delineated and the V and J germline derivations are indicated.

FIG. 3C shows the nucleotide sequence (SEQ ID NO: 62) and amino acid sequence (SEQ ID NO: 19) of the light chain variable region of the 3C2 human monoclonal antibody. The CDR1 (SEQ ID NO: 35), CDR2 (SEQ ID NO: 42) and CDR3 (SEQ ID NO: 49) regions are delineated and the V and J germline derivations are indicated.

FIG. 4A shows the nucleotide sequence (SEQ ID NO: 56) and amino acid sequence (SEQ ID NO: 4) of the heavy chain variable region of the 6A5 human monoclonal antibody. The CDR1 (SEQ ID NO: 17), CDR2 (SEQ ID NO: 23) and CDR3 (SEQ ID NO: 29) regions are delineated and the V and J germline derivations are indicated.

FIG. 4B shows the nucleotide sequence (SEQ ID NO: 63) and amino acid sequence (SEQ ID NO: 11) of the light chain variable region of the 6A5 human monoclonal antibody. The CDR1 (SEQ ID NO: 36), CDR2 (SEQ ID NO: 43) and CDR3 (SEQ ID NO: 50) regions are delineated and the V and J germline derivations are indicated.

FIG. 5A shows the nucleotide sequence (SEQ ID NO: 57) and amino acid sequence (SEQ ID NO: 5) of the heavy chain variable region of the 11E2 human monoclonal antibody. The CDR1 (SEQ ID NO: 18), CDR2 (SEQ ID NO: 24) and CDR3 (SEQ ID NO: 30) regions are delineated and the V and J germline derivations are indicated.

FIG. 5B shows the nucleotide sequence (SEQ ID NO: 64) and amino acid sequence (SEQ ID NO: 12) of the light chain variable region of the 11E2 human monoclonal antibody. The CDR1 (SEQ ID NO: 37), CDR2 (SEQ ID NO: 44) and CDR3 (SEQ ID NO: 51) regions are delineated and the V and J germline derivations are indicated.

FIG. 6A shows the nucleotide sequence (SEQ ID NO: 58) and amino acid sequence (SEQ ID NO: 6) of the heavy chain variable region of the E8D9 human monoclonal antibody. The CDR1 (SEQ ID NO: 19), CDR2 (SEQ ID NO: 25) and CDR3 (SEQ ID NO: 31) regions are delineated and the V and J germline derivations are indicated.

FIG. 6B shows the nucleotide sequence (SEQ ID NO: 65) and amino acid sequence (SEQ ID NO: 13) of the light chain variable region of the E8D9 human monoclonal antibody. The CDR1 (SEQ ID NO: 38), CDR2 (SEQ ID NO: 45) and CDR3 (SEQ ID NO: 52) regions are delineated and the V and J germline derivations are indicated.

FIG. 7 shows the alignment of the amino acid sequence of the heavy chain variable region of 1B4 with the human germline $V_H$ 2-05 amino acid sequence (SEQ ID NO: 66).

FIG. 8 shows the alignment of the amino acid sequence of the light chain variable region of 1B4 with the human germline $V_k$ A27 amino acid sequence (SEQ ID NO:70).

FIG. 9 shows the alignment of the amino acid sequence of the heavy chain variable region of E4H9 with the human germline $V_H$ 2-70 amino acid sequence (SEQ ID NO:67).

FIG. 10 shows the alignment of the amino acid sequence of the light chain variable region of E4H9 with the human germline $V_k$ A27 amino acid sequence (SEQ ID NO:70).

FIG. 11 shows the alignment of the amino acid sequence of the heavy chain variable region of 3C2 with the human germline $V_H$ 4-59 amino acid sequence (SEQ ID NO:68).

FIG. 12 shows the alignment of the amino acid sequence of the light chain variable region of 3C2 with the human germline $V_k$ L18 amino acid sequence (SEQ ID NO: 71).

FIG. 13 shows the alignment of the amino acid sequence of the light chain variable region of 3C2a with the human germline $V_k$ L15 amino acid sequence (SEQ ID NO: 72).

FIG. 14 shows the alignment of the amino acid sequence of the heavy chain variable region of 6A5 with the human germline $V_H$ 2-05 amino acid sequence (SEQ ID NO:66).

FIG. 15 shows the alignment of the amino acid sequence of the light chain variable region of 6A5 with the human germline $V_k$ A27 amino acid sequence (SEQ ID NO: 70).

FIG. 16 shows the alignment of the amino acid sequence of the heavy chain variable region of 11E2 with the human germline $V_H$ 3-20 amino acid sequence (SEQ ID NO:69).

FIG. 17 shows the alignment of the amino acid sequence of the light chain variable region of 11E2 with the human germline $V_k$ L15 amino acid sequence (SEQ ID NO: 72).

FIG. 18 shows the alignment of the amino acid sequence of the heavy chain variable region of E8D9 with the human germline $V_H$ 2-05 amino acid sequence (SEQ ID NO:66).

FIG. 19 shows the alignment of the amino acid sequence of the light chain variable region of E8D9 with the human germline $V_k$ A27 amino acid sequence (SEQ ID NO: 70).

FIG. 20 shows the sequence of human BTLA (SEQ ID NO:73).

FIG. 21A shows the nucleotide sequence (SEQ ID NO: 83) and amino acid sequence (SEQ ID NO: 74) of the heavy chain variable region of the 10H6 human monoclonal antibody. The CDR1 (SEQ ID NO: 77), CDR2 (SEQ ID NO: 78) and CDR3 (SEQ ID NO: 79) regions are delineated and the V, D and J germline derivations are indicated.

FIG. 21B shows the nucleotide sequence (SEQ ID NO: 84) and amino acid sequence (SEQ ID NO: 75) of the light chain variable region of the 10H6 human monoclonal antibody. The CDR1 (SEQ ID NO: 80), CDR2 (SEQ ID NO: 81) and CDR3 (SEQ ID NO: 82) regions are delineated and the V and J germline derivations are indicated.

FIG. 21C shows the nucleotide sequence (SEQ ID NO: 98) and amino acid sequence (SEQ ID NO: 76) of the light chain variable region of the 10H6a human monoclonal antibody. The CDR1 (SEQ ID NO: 95), CDR2 (SEQ ID NO: 96) and CDR3 (SEQ ID NO: 97) regions are delineated and the V and J germline derivations are indicated.

FIG. 22 shows the alignment of the amino acid sequence of the heavy chain variable region of 10H6 with the human germline $V_H$ 3-33 amino acid sequence (SEQ ID NO: 99).

FIG. 23 shows the alignment of the amino acid sequence of the light chain variable region of 10H6 with the human germline $V_k$ 04 amino acid sequence (SEQ ID NO:100).

FIG. 24 shows the alignment of the amino acid sequence of the light chain variable region of 10H6a with the human germline $V_k$ A27 amino acid sequence (SEQ ID NO:70).

FIG. 25A shows the nucleotide sequence (SEQ ID NO: 93) and amino acid sequence (SEQ ID NO: 85) of the heavy chain variable region of the 4C9 human monoclonal antibody. The CDR1 (SEQ ID NO: 87), CDR2 (SEQ ID NO: 88) and CDR3 (SEQ ID NO: 89) regions are delineated and the V, D and J germline derivations are indicated.

FIG. 25B shows the nucleotide sequence (SEQ ID NO: 94) and amino acid sequence (SEQ ID NO: 86) of the light chain variable region of the 4C9 human monoclonal antibody. The CDR1 (SEQ ID NO: 90), CDR2 (SEQ ID NO: 91) and CDR3 (SEQ ID NO: 92) regions are delineated and the V and J germline derivations are indicated.

FIG. 26 shows the alignment of the amino acid sequence of the heavy chain variable region of 4C9 with the human germline $V_H$ 2-05 amino acid sequence (SEQ ID NO: 66).

FIG. 27 shows the alignment of the amino acid sequence of the light chain variable region of 4C9 with the human germline $V_k$ A27 amino acid sequence (SEQ ID NO:70).

DETAILED DESCRIPTION

Figure 28A:
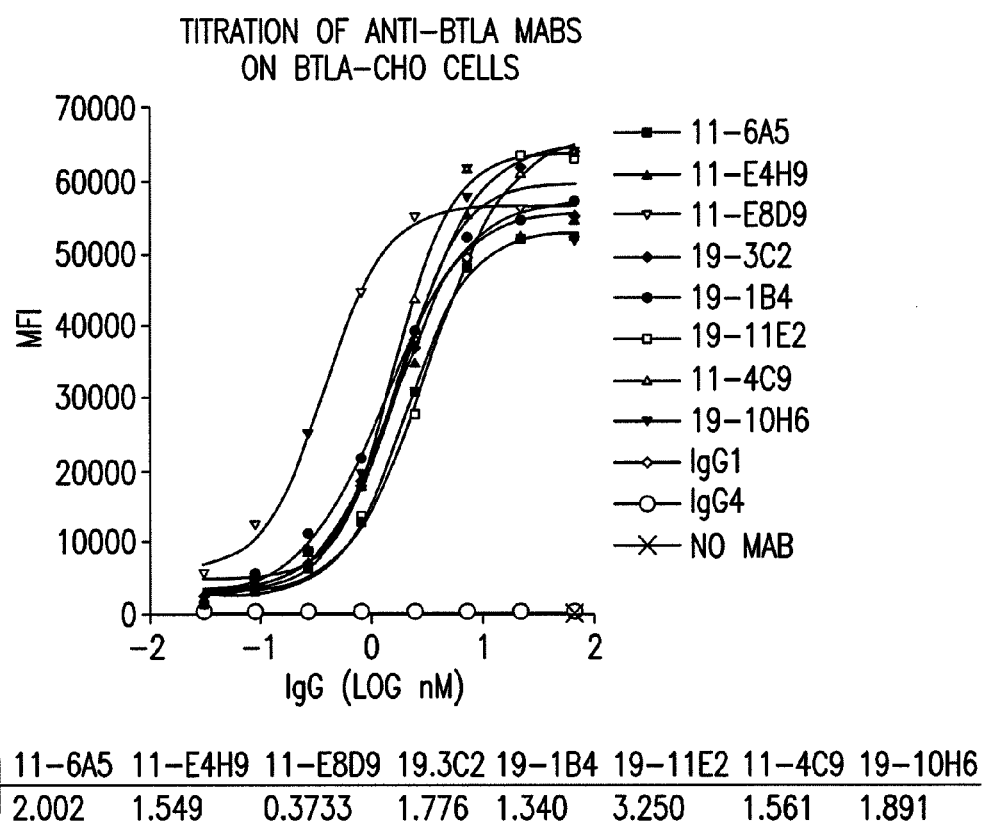
FIG. 28A demonstrates concentration dependent binding of anti-BTLA antibodies to BTLA-CHO cells.

In one aspect, the present disclosure relates to isolated monoclonal antibodies, particularly human monoclonal antibodies that bind specifically to BTLA. In certain embodiments, the antibodies of the disclosure exhibit one or more desirable functional properties, such as high affinity binding to BTLA, lack of cross-reactivity to other CD28 family members, the ability to stimulate T and/or B cell proliferation, the ability to inhibit binding of one or more BTLA ligands (e.g., HVEM) to BTLA, the ability to inhibit growth of tumor cells in vivo, the ability to stimulate antigen-specific memory responses, and/or the ability to stimulate antibody responses. In some embodiments, the antibodies of the disclosure inhibit an immune response. Additionally or alternatively, the antibodies of the disclosure are derived from particular heavy and light chain germline sequences and/or comprise particular structural features such as CDR regions comprising particular amino acid sequences.

The disclosure provides, for example, isolated antibodies, methods of making such antibodies, immunoconjugates and bispecific molecules comprising such antibodies and pharmaceutical compositions containing the antibodies, immunoconjugates or bispecific molecules of the disclosure.

In another aspect, the disclosure pertains to methods of inhibiting growth of tumor cells in a subject using anti-BTLA antibodies. Anti-BTLA antibodies are capable of inhibiting tumor cell growth in vivo. The disclosure also relates to methods of using the antibodies to modify an immune response, as well as to treat diseases such as cancer or infectious disease, or to stimulate a protective autoimmune response or to stimulate antigen-specific immune responses (e.g., by coadministration of anti-BTLA with an antigen of interest).

In order that the present disclosure may be more readily understood, certain terms are first defined. Additional definitions are set forth throughout the detailed description.

The term "B and T lymphocyte attenuator" and "BTLA", genes/proteins are used interchangeably, which includes variants, isoforms, homologs orthologs and paralogs. For example, antibodies specific for human BTLA may, in certain embodiments, cross-react with BTLA from species other than human. In other embodiments the antibodies specific for human BTLA may be completely specific for human BTLA and may not exhibit species or other types of cross reactivity. The term "human BTLA" refers to human sequence BTLA, such as the complete amino acid sequence of human BTLA that has Genbank accession number NP_861445. The human BTLA sequences may differ from human BTLA of SEQ ID NO:73 by having, for example, conserved mutations or mutations in non-conserved regions and the BTLA has substantially the same biological function as the human BTLA of SEQ ID NO:73. For example, a biological function of human BTLA is to suppress an immune response, such as a T-cell response. That is, BTLA is considered to be a negative regulator. It has C-terminal inhibitor motifs that are involved in reducing IL-2 production and T cell expansion (Watanabe et al., Nat. Immunol., 4, 670-679, 2003; Chemnitz et al., J. Immunol., 176, 6603-6614, 2006). In addition, a biological function of human BTLA may be having, for example, an epitope in the extracellular domain of BTLA that is specifically bound by an antibody of the instant disclosure.

A particular BTLA sequence will generally be at least 90% identical in amino acid sequence to human BTLA of SEQ ID NO:73 and contain amino acid residues that identify the amino acid sequence as being human when compared to BTLA amino acid sequences of other species (e.g., murine). In certain cases, a human BTLA may be at least 95%, or even at least 96%, 97%, 98% or 99% identical to human BTLA of SEQ ID NO:73. In certain embodiments, a human BTLA sequence will display no more than 10 amino acid differences from the BTLA of SEQ ID NO:73. In certain embodiments, the human BTLA may display no more than 5, or even no more than 4, 3, 2, or 1 amino acid difference from the BTLA of SEQ ID NO:73. Percent identity can be determined as described herein.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell. An example of a "cell surface receptor" of the present disclosure is the BTLA receptor.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4.

The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. The term "antigen-binding portion" of an antibody (or simply "antibody portion"), as used herein, refers to one or more fragments of an antibody that retain the ability to specifically bind to an antigen (e.g., BTLA). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_H$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds BTLA is substantially free of antibodies that specifically bind antigens other than BTLA). An isolated antibody that specifically binds BTLA may, however, have cross-reactivity to other antigens, such as BTLA molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, an antibody that "specifically binds to human BTLA" is intended to refer to an antibody that binds to human BTLA with a $K_D$ of $1\times10^{-7}$ M or less, more preferably $5\times10^{-8}$ M or less, more preferably $1\times10^{-8}$ M or less, more preferably $5\times10^{-9}$ M or less.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

As used herein, the term "high affinity" for an IgG antibody refers to an antibody having a $K_D$ of $10^{-8}$ M or less, more preferably $10^{-9}$ M or less and even more preferably $10^{-10}$ M or less for a target antigen. However, "high affinity" binding can vary for other antibody isotypes. For example, "high affinity" binding for an IgM isotype refers to an antibody having a $K_D$ of $10^{-7}$ M or less, more preferably $10^{-8}$ M or less, even more preferably $10^{-9}$ M or less.

As used herein, the term "subject" includes any human or nonhuman animal. The term "nonhuman animal" includes all vertebrates, e.g., mammals and non-mammals, such as non-human primates, sheep, dogs, cats, horses, cows, chickens, amphibians, reptiles, etc.

Various aspects of the disclosure are described in further detail in the following subsections.

Anti-BTLA Antibodies

The antibodies of the disclosure are characterized by particular functional features or properties of the antibodies. For example, the antibodies bind specifically to BTLA (e.g., bind to human BTLA and may cross-react with BTLA from other species, such as cynomolgus monkey). Preferably, an antibody of the disclosure binds to BTLA with high affinity, for example with a $K_D$ of $1\times10^{-7}$ M or less. The anti-BTLA antibodies of the disclosure preferably exhibit one or more of the following characteristics:

(a) binds to human BTLA with a $K_D$ of $1\times10^{-7}$ M or less;
(b) does not substantially bind to human TrkB, CD28, CTLA-4, PD-1 or ICOS; or
(c) inhibits the binding of HVEM to BTLA.

In additional embodiments, the anti-BTLA antibodies of the disclosure exhibit the following characteristics:

(a) stimulates immune responses;
(b) stimulates antibody responses; or
(c) inhibits tumor cell growth in vivo.

In additional embodiments, the anti-BTLA antibodies of the disclosure stimulate immune responses. That is in some embodiments, the antibodies of the disclosure are antagonist antibodies and prevent an HVEM mediated inhibitory signal while in other embodiments the antibodies of the disclosure are agonist antibodies that activate BTLA and provide an inhibitory signal to the cell expressing BTLA.

Preferably, the antibody binds to human BTLA with a $K_D$ of $5\times10^{-8}$ M or less, binds to human BTLA with a $K_D$ of $1\times10^{-8}$ M or less, binds to human BTLA with a $K_D$ of $5\times10^{-9}$ M or less, or binds to human BTLA with a $K_D$ of between $1\times10^{-8}$ M and $1\times10^{-10}$ M or less.

An antibody of the disclosure may exhibit any combination of the above-listed features, such as two, three, four, five or more of the above-listed features.

Standard assays to evaluate the binding ability of the antibodies toward BTLA are known in the art, including for example, ELISAs, Western blots and RIAs. The binding kinetics (e.g., binding affinity) of the antibodies also can be assessed by standard assays known in the art, such as by Biacore analysis. Suitable assays for evaluating any of the above-described characteristics are described in detail in the Examples.

Monoclonal Antibodies 1B4, E4H9, 3C2, 3C2a, 6A5, 11E2, E8D9, 10H6, 10H6a, and 4C9

Preferred antibodies of the disclosure are the human monoclonal antibodies 1B4, E4H9, 3C2, 3C2a, 6A5, 11E2, E8D9, 10H6, 10H6a, and 4C9, isolated and structurally characterized as described in Examples 1 and 2. The $V_H$ amino acid sequences of 1B4, E4H9, 3C2, 6A5, 11E2, E8D9, 10H6, 10H6a, and 4C9 are shown in SEQ ID NOs: 1, 2, 3, 4, 5, 6, 74, and 85, respectively. The $V_H$ amino acid sequence of 3C2a is the same as that of 3C2. The $V_H$ amino acid sequence of 10H6a is the same as that of 10H6. The $V_L$ amino acid sequences of 1B4, E4H9, 3C2, 3C2a, 6A5, 11E2, E8D9, 10H6, 10H6a, and 4C9 are shown in SEQ ID NOs: 7, 8, 9, 10, 11, 12, 13, 75, 76, and 86, respectively.

Given that each of these antibodies can bind to BTLA, the $V_H$ and $V_L$ sequences can be "mixed and matched" to create other anti-BTLA binding molecules of the disclosure. BTLA binding of such "mixed and matched" antibodies can be tested using the binding assays described above and in the Examples (e.g., ELISAs). Preferably, when $V_H$ and $V_L$ chains are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one aspect, the disclosure provides an isolated monoclonal antibody, or antigen binding portion thereof comprising:
  (a) a heavy chain variable region comprising an amino acid sequence selected from the group consisting of SEQ ID NOs: 1, 2, 3, 4, 5, 6, 74, and 85; and
  (b) a light chain variable region comprising an amino acid sequence selected from the group consisting of SEQ ID NOs: 7, 8, 9, 10, 11, 12, 13, 75, 76, and 86;
  wherein the antibody specifically binds BTLA, preferably human BTLA.

Preferred heavy and light chain combinations include:
  (a) a heavy chain variable region comprising the amino acid sequence of SEQ ID NO: 1; and (b) a light chain variable region comprising the amino acid sequence of SEQ ID NO: 7; or
  (a) a heavy chain variable region comprising the amino acid sequence of SEQ ID NO: 2; and (b) a light chain variable region comprising the amino acid sequence of SEQ ID NO: 8; or
  (a) a heavy chain variable region comprising the amino acid sequence of SEQ ID NO: 3; and (b) a light chain variable region comprising the amino acid sequence of SEQ ID NO: 9; or
  (a) a heavy chain variable region comprising the amino acid sequence of SEQ ID NO: 3; and (b) a light chain variable region comprising the amino acid sequence of SEQ ID NO: 10; or
  (a) a heavy chain variable region comprising the amino acid sequence of SEQ ID NO: 4; and (b) a light chain variable region comprising the amino acid sequence of SEQ ID NO: 11; or
  (a) a heavy chain variable region comprising the amino acid sequence of SEQ ID NO: 5; and (b) a light chain variable region comprising the amino acid sequence of SEQ ID NO: 12; or
  (a) a heavy chain variable region comprising the amino acid sequence of SEQ ID NO: 6; and (b) a light chain variable region comprising the amino acid sequence of SEQ ID NO: 13;
  (a) a heavy chain variable region comprising the amino acid sequence of SEQ ID NO: 74; and (b) a light chain variable region comprising the amino acid sequence of SEQ ID NO: 75;
  (a) a heavy chain variable region comprising the amino acid sequence of SEQ ID NO: 74; and (b) a light chain variable region comprising the amino acid sequence of SEQ ID NO: 76;
  (a) a heavy chain variable region comprising the amino acid sequence of SEQ ID NO: 85; and (b) a light chain variable region comprising the amino acid sequence of SEQ ID NO: 86.

In another aspect, the disclosure provides antibodies that comprise the heavy chain and light chain CDR1s, CDR2s and CDR3s of 1B4, E4H9, 3C2, 3C2a, 6A5, 11E2, E8D9, 10H6, 10H6a, and 4C9, or combinations thereof. The amino acid sequences of the $V_H$ CDR1s of 1B4, E4H9, 3C2, 6A5, 11E2, E8D9, 10H6, and 4C9 are shown in SEQ ID NOs: 14, 15, 16, 17, 18, 19, 77, and 87, respectively. The amino acid sequences of the $V_H$ CDR2s of 1B4, E4H9, 3C2, 6A5, 11E2, E8D9, 10H6, and 4C9 are shown in SEQ ID NOs: 20, 21, 22, 23, 24, 25, 78, and 88, respectively. The amino acid sequences of the $V_H$ CDR3s of 1B4, E4H9, 3C2, 6A5, 11E2, E8D9, 10H6, and 4C9 are shown in SEQ ID NOs: 26, 27, 28, 29, 30, 31, 79, and 89, respectively. The amino acid sequences of the $V_k$ CDR1s of 1B4, E4H9, 3C2, 3C2a, 6A5, 11E2, E8D9, 10H6, 10H6a, and 4C9 are shown in SEQ ID NOs: 32, 33, 34, 35, 36, 37, 38, 80, 90, and 95, respectively. The amino acid sequences of the $V_k$ CDR2s of 1B4, E4H9, 3C2, 3C2a, 6A5, 11E2, E8D9, 10H6, 10H6a, and 4C9 are shown in SEQ ID NOs: 39, 40, 41, 42, 43, 44, 45, 81, 91, and 96, respectively. The amino acid sequences of the $V_k$ CDR3s of 1B4, E4H9, 3C2, 3C2a, 6A5, 11E2, E8D9, 10H6, 10H6a, and 4C9 are shown in SEQ ID NOs: 46, 47, 48, 49, 50, 51, 52, 82, 92, and 97, respectively. The CDR regions are delineated using the Kabat system (Kabat, E. A., et al. (1991) Sequences of Proteins of Immunological Interest, Fifth Edition, U.S. Department of Health and Human Services, NIH Publication No. 91-3242).

Given that each of these antibodies can bind to BTLA and that antigen-binding specificity is provided primarily by the CDR1, CDR2, and CDR3 regions, the $V_H$ CDR1, CDR2, and CDR3 sequences and $V_k$ CDR1, CDR2, and CDR3 sequences can be "mixed and matched" (i.e., CDRs from different antibodies can be mixed and match, although each antibody must contain a $V_H$ CDR1, CDR2, and CDR3 and a $V_k$ CDR1, CDR2, and CDR3) to create other anti-BTLA binding molecules of the disclosure. BTLA binding of such "mixed and matched" antibodies can be tested using the binding assays described above and in the Examples (e.g., ELISAs, Biacore analysis). Preferably, when $V_H$ CDR sequences are mixed and matched, the CDR1, CDR2 and/or CDR3 sequence from a particular $V_H$ sequence is replaced with a structurally similar CDR sequence(s). Likewise, when $V_k$ CDR sequences are mixed and matched, the CDR1, CDR2 and/or CDR3 sequence from a particular $V_k$ sequence preferably is replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences disclosed herein for monoclonal antibodies antibodies 1B4, E4H9, 3C2, 3C2a, 6A5, 11E2, E8D9, 10H6, 10H6a, and 4C9.

Accordingly, in another aspect, the disclosure provides an isolated monoclonal antibody, or antigen binding portion thereof comprising:
  (a) a heavy chain variable region CDR1 comprising an amino acid sequence selected from the group consisting of SEQ ID NOs: 14, 15, 16, 17, 18, 19, 77, and 87;
  (b) a heavy chain variable region CDR2 comprising an amino acid sequence selected from the group consisting of SEQ ID NOs: 20, 21, 22, 23, 24, 25, 78, and 88;
  (c) a heavy chain variable region CDR3 comprising an amino acid sequence selected from the group consisting of SEQ ID NOs: 26, 27, 28, 29, 30, 31, 79, and 89;
  (d) a light chain variable region CDR1 comprising an amino acid sequence selected from the group consisting of SEQ ID NOs: 32, 33, 34, 35, 36, 37, 38, 80, 90, and 95;
  (e) a light chain variable region CDR2 comprising an amino acid sequence selected from the group consisting of SEQ ID NOs: 39, 40, 41, 42, 43, 44, 45, 81, 91, and 96; and
  (f) a light chain variable region CDR3 comprising an amino acid sequence selected from the group consisting of SEQ ID NOs: 46, 47, 48, 49, 50, 51, 52, 82, 92, and 97;
  wherein the antibody specifically binds BTLA, preferably human BTLA.

In a preferred embodiment, the antibody comprises:
(a) a heavy chain variable region CDR1 comprising SEQ ID NO: 14;
(b) a heavy chain variable region CDR2 comprising SEQ ID NO: 20;
(c) a heavy chain variable region CDR3 comprising SEQ ID NO: 26;
(d) a light chain variable region CDR1 comprising SEQ ID NO: 32;
(e) a light chain variable region CDR2 comprising SEQ ID NO: 39; and
(f) a light chain variable region CDR3 comprising SEQ ID NO: 46.

In another preferred embodiment, the antibody comprises:
(a) a heavy chain variable region CDR1 comprising SEQ ID NO: 15;
(b) a heavy chain variable region CDR2 comprising SEQ ID NO: 21;
(c) a heavy chain variable region CDR3 comprising SEQ ID NO: 27;
(d) a light chain variable region CDR1 comprising SEQ ID NO: 33;
(e) a light chain variable region CDR2 comprising SEQ ID NO: 40; and
(f) a light chain variable region CDR3 comprising SEQ ID NO: 47.

In another preferred embodiment, the antibody comprises:
(a) a heavy chain variable region CDR1 comprising SEQ ID NO: 16;
(b) a heavy chain variable region CDR2 comprising SEQ ID NO: 22;
(c) a heavy chain variable region CDR3 comprising SEQ ID NO: 28;
(d) a light chain variable region CDR1 comprising SEQ ID NO: 34;
(e) a light chain variable region CDR2 comprising SEQ ID NO: 41; and
(f) a light chain variable region CDR3 comprising SEQ ID NO: 48.

In another preferred embodiment, the antibody comprises:
(a) a heavy chain variable region CDR1 comprising SEQ ID NO: 16;
(b) a heavy chain variable region CDR2 comprising SEQ ID NO: 22;
(c) a heavy chain variable region CDR3 comprising SEQ ID NO: 28;
(d) a light chain variable region CDR1 comprising SEQ ID NO: 35;
(e) a light chain variable region CDR2 comprising SEQ ID NO: 42; and
(f) a light chain variable region CDR3 comprising SEQ ID NO: 49.

In another preferred embodiment, the antibody comprises:
(a) a heavy chain variable region CDR1 comprising SEQ ID NO: 17;
(b) a heavy chain variable region CDR2 comprising SEQ ID NO: 23;
(c) a heavy chain variable region CDR3 comprising SEQ ID NO: 29;
(d) a light chain variable region CDR1 comprising SEQ ID NO: 36;
(e) a light chain variable region CDR2 comprising SEQ ID NO: 43; and
(f) a light chain variable region CDR3 comprising SEQ ID NO: 50.

In another preferred embodiment, the antibody comprises:
(a) a heavy chain variable region CDR1 comprising SEQ ID NO: 18;
(b) a heavy chain variable region CDR2 comprising SEQ ID NO: 24;
(c) a heavy chain variable region CDR3 comprising SEQ ID NO: 30;
(d) a light chain variable region CDR1 comprising SEQ ID NO: 37;
(e) a light chain variable region CDR2 comprising SEQ ID NO: 44; and
(f) a light chain variable region CDR3 comprising SEQ ID NO: 51.

In another preferred embodiment, the antibody comprises:
(a) a heavy chain variable region CDR1 comprising SEQ ID NO: 19;
(b) a heavy chain variable region CDR2 comprising SEQ ID NO: 25;
(c) a heavy chain variable region CDR3 comprising SEQ ID NO: 31;
(d) a light chain variable region CDR1 comprising SEQ ID NO: 38;
(e) a light chain variable region CDR2 comprising SEQ ID NO: 45; and
(f) a light chain variable region CDR3 comprising SEQ ID NO: 52.

In another preferred embodiment, the antibody comprises:
(a) a heavy chain variable region CDR1 comprising SEQ ID NO: 77;
(b) a heavy chain variable region CDR2 comprising SEQ ID NO: 78;
(c) a heavy chain variable region CDR3 comprising SEQ ID NO: 79;
(d) a light chain variable region CDR1 comprising SEQ ID NO: 80;
(e) a light chain variable region CDR2 comprising SEQ ID NO: 81; and
(f) a light chain variable region CDR3 comprising SEQ ID NO: 82.

In another preferred embodiment, the antibody comprises:
(a) a heavy chain variable region CDR1 comprising SEQ ID NO: 87;
(b) a heavy chain variable region CDR2 comprising SEQ ID NO: 88;
(c) a heavy chain variable region CDR3 comprising SEQ ID NO: 89;
(d) a light chain variable region CDR1 comprising SEQ ID NO: 90;
(e) a light chain variable region CDR2 comprising SEQ ID NO: 91; and
(f) a light chain variable region CDR3 comprising SEQ ID NO: 92.

In another preferred embodiment, the antibody comprises:
(a) a heavy chain variable region CDR1 comprising SEQ ID NO: 77;
(b) a heavy chain variable region CDR2 comprising SEQ ID NO: 78;
(c) a heavy chain variable region CDR3 comprising SEQ ID NO: 79;
(d) a light chain variable region CDR1 comprising SEQ ID NO: 95;
(e) a light chain variable region CDR2 comprising SEQ ID NO: 96; and
(f) a light chain variable region CDR3 comprising SEQ ID NO: 97.

It is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, for example, Klimka et al., *British J. of Cancer* 83(2):252-260 (2000) (describing the production of a humanized anti-CD30 antibody using only the heavy chain variable domain CDR3 of murine anti-CD30 antibody Ki-4); Beiboer et al., *J. Mol. Biol.* 296:833-849 (2000) (describing recombinant epithelial glycoprotein-2 (EGP-2) antibodies using only the heavy chain CDR3 sequence of the parental murine MOC-31 anti-EGP-2 antibody); Rader et al., *Proc. Natl. Acad. Sci. U.S.A.* 95:8910-8915 (1998) (describing a panel of humanized anti-integrin $\alpha_v\beta_3$ antibodies using a heavy and light chain variable CDR3 domain of a murine anti-integrin $\alpha_v\beta_3$ antibody LM609 wherein each member antibody comprises a distinct sequence outside the CDR3 domain and capable of binding the same epitope as the parent muring antibody with affinities as high or higher than the parent murine antibody); Barbas et al., *J. Am. Chem. Soc.* 116:2161-2162 (1994) (disclosing that the CDR3 domain provides the most significant contribution to antigen binding); Barbas et al., *Proc. Natl. Acad. Sci. U.S.A.* 92:2529-2533 (1995) (describing the grafting of heavy chain CDR3 sequences of three Fabs (SI-1, SI-40, and SI-32) against human placental DNA onto the heavy chain of an anti-tetanus toxoid Fab thereby replacing the existing heavy chain CDR3 and demonstrating that the CDR3 domain alone conferred binding specificity); and Ditzel et al., *J. Immunol.* 157:739-749 (1996) (describing grafting studies wherein transfer of only the heavy chain CDR3 of a parent polyspecific Fab LNA3 to a heavy chain of a monospecific IgG tetanus toxoid-binding Fab p313 antibody was sufficient to retain binding specificity of the parent Fab). Each of these references is hereby incorporated by reference in its entirety.

Accordingly, within certain aspects, the present disclosure provides monoclonal antibodies comprising one or more heavy and/or light chain CDR3 domain from a non-human antibody, such as a mouse or rat antibody, wherein the monoclonal antibody is capable of specifically binding to BTLA. Within some embodiments, such inventive antibodies comprising one or more heavy and/or light chain CDR3 domain from a non-human antibody (a) are capable of competing for binding with; (b) retain the functional characteristics; (c) bind to the same epitope; and/or (d) have a similar binding affinity as the corresponding parental non-human antibody.

Within other aspects, the present disclosure provides monoclonal antibodies comprising one or more heavy and/or light chain CDR3 domain from a first human antibody, such as, for example, a human antibody obtained from a non-human animal, wherein the first human antibody is capable of specifically binding to BTLA and wherein the CDR3 domain from the first human antibody replaces a CDR3 domain in a human antibody that is lacking binding specificity for BTLA to generate a second human antibody that is capable of specifically binding to BTLA. Within some embodiments, such inventive antibodies comprising one or more heavy and/or light chain CDR3 domain from the first human antibody (a) are capable of competing for binding with; (b) retain the functional characteristics; (c) bind to the same epitope; and/or (d) have a similar binding affinity as the corresponding parental first human antibody.

Antibodies Having Particular Germline Sequences

In certain embodiments, an antibody of the disclosure comprises a heavy chain variable region from a particular germline heavy chain immunoglobulin gene and/or a light chain variable region from a particular germline light chain immunoglobulin gene.

For example, in a preferred embodiment, the disclosure provides an isolated monoclonal antibody, or an antigen-binding portion thereof, comprising a heavy chain variable region that is the product of or derived from a human $V_H$ 2-05 gene, wherein the antibody specifically binds BTLA, preferably human BTLA. In another preferred embodiment, the disclosure provides an isolated monoclonal antibody, or an antigen-binding portion thereof, comprising a heavy chain variable region that is the product of or derived from a human $V_H$ 2-70 gene, wherein the antibody specifically binds BTLA, preferably human BTLA. In another preferred embodiment, the disclosure provides an isolated monoclonal antibody, or an antigen-binding portion thereof, comprising a heavy chain variable region that is the product of or derived from a human $V_H$ 4-59 gene, wherein the antibody specifically binds BTLA, preferably human BTLA. In another preferred embodiment, the disclosure provides an isolated monoclonal antibody, or an antigen-binding portion thereof, comprising a heavy chain variable region that is the product of or derived from a human $V_H$ 3-20 gene, wherein the antibody specifically binds BTLA, preferably human BTLA. In another preferred embodiment, the disclosure provides an isolated monoclonal antibody, or an antigen-binding portion thereof, comprising a heavy chain variable region that is the product of or derived from a human $V_H$ 3-33 gene, wherein the antibody specifically binds BTLA, preferably human BTLA. In yet another preferred embodiment, the disclosure provides an isolated monoclonal antibody, or an antigen-binding portion thereof, comprising a light chain variable region that is the product of or derived from a human $V_K$ A27 gene, wherein the antibody specifically binds BTLA, preferably human BTLA. In yet another preferred embodiment, the disclosure provides an isolated monoclonal antibody, or an antigen-binding portion thereof, comprising a light chain variable region that is the product of or derived from a human $V_K$ L18 gene, wherein the antibody specifically binds BTLA, preferably human BTLA. In yet another preferred embodiment, the disclosure provides an isolated monoclonal antibody, or an antigen-binding portion thereof, comprising a light chain variable region that is the product of or derived from a human $V_K$ L15 gene, wherein the antibody specifically binds BTLA, preferably human BTLA. In yet another preferred embodiment, the disclosure provides an isolated monoclonal antibody, or an antigen-binding portion thereof, comprising a light chain variable region that is the product of or derived from a human $V_K$ 04 gene, wherein the antibody specifically binds BTLA, preferably human BTLA. In yet another preferred embodiment, the disclosure provides an isolated monoclonal antibody, or antigen-binding portion thereof, wherein the antibody:

(a) comprises a heavy chain variable region that is the product of or derived from a human $V_H$ 2-05, 2-70, 4-59, 3-20, or 3-33 (which gene encodes the amino acid sequence set forth in SEQ ID NO: 66, 67, 68, 69, or 99 respectively);

(b) comprises a light chain variable region that is the product of or derived from a human $V_K$ A27, L18, L15 or 04 gene (which gene encodes the amino acid sequence set forth in SEQ ID NO: 70, 71, or 72, respectively); and (c) specifically binds to BTLA.

Examples of antibodies having $V_H$ and $V_K$ of $V_H$ 2-05 and $V_K$ A27, respectively are 1B4, 6A5, and E8D9. An example of an antibody having a $V_H$ and $V_K$ of $V_H$ 2-70 and $V_K$ A27, respectively is E4H9. An example of an antibody having a $V_H$ and $V_K$ of $V_H$ 4-59 and $V_K$ L18, respectively is 3C2. An example of an antibody having a $V_H$ and $V_K$ of $V_H$ 4-59 and $V_K$ A27, respectively is 3C2a. An example of an antibody having a $V_H$ and $V_K$ of $V_H$ 3-20 and $V_K$ 115, respectively is 11E2. An example of an antibody having a $V_H$ and $V_K$ of $V_H$ 3-33 and V$_K$ 04, respectively is 10H6. An example of an antibody having a V$_H$ and V$_K$ of V$_H$ 3-33 and V$_K$ A27, respectively is 10H6a. An example of an antibody having a V$_H$ and V$_K$ of V$_H$ 2-05 and V$_K$ A27, respectively is 4C9.

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, an antibody of the disclosure comprises heavy and light chain variable regions comprising amino acid sequences that are homologous to the amino acid sequences of the preferred antibodies described herein, and wherein the antibodies retain the desired functional properties of the anti-BTLA antibodies of the disclosure.

For example, the disclosure provides an isolated monoclonal antibody, or antigen binding portion thereof, comprising a heavy chain variable region and a light chain variable region, wherein:

(a) the heavy chain variable region comprises an amino acid sequence that is at least 80% homologous to an amino acid sequence selected from the group consisting of SEQ ID NOs: 1, 2, 3, 4, 5, 6, 74, and 85;

(b) the light chain variable region comprises an amino acid sequence that is at least 80% homologous to an amino acid sequence selected from the group consisting of SEQ ID NOs: 7, 8, 9, 10, 11, 12, 13, 75, 76, and 86; and the antibody exhibits one or more of the following properties:

(i) the antibody binds to human BTLA with a K$_D$ of $1 \times 10^{-7}$ M or less;

(ii) the antibody does not substantially bind to human TrkB, CD28, CTLA-4, PD-1 or ICOS;

(iii) the antibody inhibits the binding of HVEM to BTLA;

(iv) the antibody stimulates immune responses;

(v) the antibody stimulates antibody responses;

(vi) the antibody inhibits tumor cell growth in vivo.

In other embodiments the antibody inhibits or suppresses immune responses.

In other embodiments, the V$_H$ and/or V$_L$ amino acid sequences may be 85%, 90%, 95%, 96%, 97%, 98% or 99% homologous to the sequences set forth above. An antibody having V$_H$ and V$_L$ regions having high (i.e., 80% or greater) homology to the V$_H$ and V$_L$ regions of the sequences set forth above, can be obtained by mutagenesis (e.g., site-directed or PCR-mediated mutagenesis) of nucleic acid molecules encoding SEQ ID NOs: 53, 54, 55, 56, 57, 58, 59, 60, 61, 62, 63, 64, and/or 65, followed by testing of the encoded altered antibody for retained function (i.e., the functions set forth in (c) through (g) above) using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present disclosure can further be used as a "query sequence" to perform a search against public databases to, for example, identify related sequences. Such searches can be performed using the XBLAST program (version 2.0) of Altschul, et al. (1990) *J. Mol. Biol.* 215:403-10. BLAST protein searches can be performed with the XBLAST program, score=50, wordlength=3 to obtain amino acid sequences homologous to the antibody molecules of the disclosure. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used (see www.ncbi.nlm.nih.gov).

Antibodies with Conservative Modifications

In certain embodiments, an antibody of the disclosure comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., 1B4, E4H9, 3C2, 3C2a, 6A5, 11E2, and E8D9), or conservative modifications thereof, and wherein the antibodies retain the desired functional properties of the anti- BTLA antibodies of the disclosure. Accordingly, the disclosure provides an isolated monoclonal antibody, or antigen binding portion thereof, comprising a heavy chain variable region comprising CDR1, CDR2, and CDR3 sequences and a light chain variable region comprising CDR1, CDR2, and CDR3 sequences, wherein:

(a) the heavy chain variable region CDR3 sequence comprises an amino acid sequence selected from the group consisting of amino acid sequences of SEQ ID NOs: 26, 27, 28, 29, 30, 31, 79, and 89, and conservative modifications thereof;

(b) the light chain variable region CDR3 sequence comprises an amino acid sequence selected from the group consisting of amino acid sequence of SEQ ID NOs: 46, 47, 48, 49, 50, 51, 52, 82, 92, and 97, and conservative modifications thereof; and the antibody exhibits one or more of the following properties:

(i) the antibody binds to human BTLA with a $K_D$ of $1\times10^{-7}$ M or less;

(ii) the antibody does not substantially bind to human TrkB, PD-1, CD28, CTLA-4 or ICOS;

(iii) the antibody inhibits the binding of HVEM to BTLA;

(iv) the antibody stimulates immune responses;

(v) the antibody stimulates antibody responses;

(vi) the antibody inhibits tumor cell growth in vivo.

In other embodiments the antibody inhibits or suppresses an immune response.

In a preferred embodiment, the heavy chain variable region CDR2 sequence comprises an amino acid sequence selected from the group consisting of amino acid sequences of SEQ ID NOs: 20, 21, 22, 23, 24, 25, 78, and 88, and conservative modifications thereof; and the light chain variable region CDR2 sequence comprises an amino acid sequence selected from the group consisting of amino acid sequences of SEQ ID NOs: 39, 40, 41, 42, 43, 44, 45, 81, 91, and 96, and conservative modifications thereof. In another preferred embodiment, the heavy chain variable region CDR1 sequence comprises an amino acid sequence selected from the group consisting of amino acid sequences of SEQ ID NOs: 14, 15, 16, 17, 18, 19, 77, and 87, and conservative modifications thereof; and the light chain variable region CDR1 sequence comprises an amino acid sequence selected from the group consisting of amino acid sequences of SEQ ID NOs: 32, 33, 34, 35, 36, 37, 38, 80, 90, and 95, and conservative modifications thereof.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the disclosure by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the disclosure can be replaced with other amino acid residues from the same side chain family and the altered antibody can be tested for retained function (i.e., the functions set forth in (c) through (g) above) using the functional assays described herein.

Antibodies that Bind to the Same Epitope as Anti-BTLA Antibodies of the Disclosure In another embodiment, the disclosure provides antibodies that bind to the same epitope on human BTLA as any of the BTLA monoclonal antibodies of the disclosure (i.e., antibodies that have the ability to cross-compete for binding to BTLA with any of the monoclonal antibodies of the disclosure). In preferred embodiments, the reference antibody for cross-competition studies can be the monoclonal antibody 1B4 (having $V_H$ and $V_L$ sequences as shown in SEQ ID NOs: 1 and 7, respectively), or the monoclonal antibody E4H9 (having $V_H$ and $V_L$ sequences as shown in SEQ ID NOs: 2 and 8, respectively), or the monoclonal antibody 3C2 (having $V_H$ and $V_L$ sequences as shown in SEQ ID NOs: 3 and 9, respectively), or the monoclonal antibody 3C2a (having $V_H$ and $V_L$ sequences as shown in SEQ ID NOs: 3 and 10, respectively), or the monoclonal antibody 6A5 (having $V_H$ and $V_L$ sequences as shown in SEQ ID NOs: 4 and 11, respectively), or the monoclonal antibody 11E2 (having $V_H$ and $V_L$ sequences as shown in SEQ ID NOs: 5 and 12, respectively), or the monoclonal antibody E8D9 (having $V_H$ and $V_L$ sequences as shown in SEQ ID NOs: 6 and 13, respectively), or the monoclonal antibody 10H6 (having $V_H$ and $V_L$ sequences as shown in SEQ ID NOs: 74 and 75, respectively), or the monoclonal antibody 10H6a (having $V_H$ and $V_L$ sequences as shown in SEQ ID NOs: 74 and 76, respectively), or the monoclonal antibody 4C9 (having $V_H$ and $V_L$ sequences as shown in SEQ ID NOs: 85 and 86, respectively). Such cross-competing antibodies can be identified based on their ability to cross-compete with 1B4, E4H9, 3C2, 3C2a, 6A5, 11E2, E8D9, 10H6, 10H6a or 4C9 in standard BTLA binding assays. For example, BIAcore analysis, ELISA assays or flow cytometry may be used to demonstrate cross-competition with the antibodies of the current disclosure. The ability of a test antibody to inhibit the binding of, for example, 1B4, E4H9, 3C2, 3C2a, 6A5, 11E2, E8D9, 10H6, 10116a or 4C9, to human BTLA demonstrates that the test antibody can compete with 1B4, E4H9, 3C2, 3C2a, 6A5, 11E2, E8D9, 10H6, 10H6a or 4C9 for binding to human BTLA and thus binds to the same epitope on human BTLA as 1B4, E4H9, 3C2, 3C2a, 6A5, 11E2, E8D9, 10H6, 10H6a or 4C9. In a preferred embodiment, the antibody that binds to the same epitope on human BTLA as 1B4, E4H9, 3C2, 3C2a, 6A5, 11E2, E8D9, 10H6, 10H6a or 4C9 is a human monoclonal antibody. Such human monoclonal antibodies can be prepared and isolated as described in the Examples.

Engineered and Modified Antibodies

An antibody of the disclosure further can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; Queen, C. et al. (1989) *Proc. Natl. Acad. See. U.S.A.* 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of the disclosure pertains to an isolated monoclonal antibody, or antigen binding portion thereof, comprising a heavy chain variable region comprising CDR1, CDR2, and CDR3 sequences comprising an amino acid sequence selected from the group consisting of SEQ ID NOs: 14, 15, 16, 17, 18, 19, 77, and 87, SEQ ID NOs: 20, 21, 22, 23, 24, 25, 78, and 88, and SEQ ID NOs: 26, 27, 28, 29, 30, 31, 79, and 89, respectively, and a light chain variable region comprising CDR1, CDR2, and CDR3 sequences comprising an amino acid sequence selected from the group consisting of SEQ ID NOs: 32, 33, 34, 35, 36, 37, 38, 80, 90, and 95, SEQ ID NOs: 39, 40, 41, 42, 43, 44, 45, 81, 91, and 96, and SEQ ID NOs: 46, 47, 48, 49, 50, 51, 52, 82, 92, and 97, respectively. Thus, such antibodies contain the $V_H$ and $V_L$ CDR sequences of monoclonal antibodies 1B4, E4H9, 3C2, 3C2a, 6A5, 11E2, E8D9, 10H6, 10H6A, and 4C9, yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_H$ Segments Reveals a Strong Bias in their Usage" *Eur. J. Immunol.* 24:827-836; the contents of each of which are expressly incorporated herein by reference.

Antibody protein sequences are compared against a compiled protein sequence database using one of the sequence similarity searching methods called the Gapped BLAST (Altschul et al. (1997) *Nucleic Acids Research* 25:3389-3402), which is well known to those skilled in the art. BLAST is a heuristic algorithm in that a statistically significant alignment between the antibody sequence and the database sequence is likely to contain high-scoring segment pairs (HSP) of aligned words. Segment pairs whose scores cannot be improved by extension or trimming is called a hit. Briefly, the nucleotide sequences of VBASE origin (http://vbase.mrc-cpe.cam.ac.uk/vbase1/list2.php) are translated and the region between and including FR1 through FR3 framework region is retained. The database sequences have an average length of 98 residues. Duplicate sequences which are exact matches over the entire length of the protein are removed. A BLAST search for proteins using the program blastp with default, standard parameters except the low complexity filter which is turned off and the substitution matrix of BLOSUM62, filters for top 5 hits yielding sequence matches. The nucleotide sequences are translated in all six frames and the frame with no stop codons in the matching segment of the database sequence is considered the potential hit. This is in turn confirmed using the BLAST program tblastx. This translates the antibody sequence in all six frames and compares those translations to the VBASE nucleotide sequences dynamically translated in all six frames.

The identities are exact amino acid matches between the antibody sequence and the protein database over the entire length of the sequence. The positives (identities+substitution match) are not identical but amino acid substitutions guided by the BLOSUM62 substitution matrix. If the antibody sequence matches two of the database sequences with same identity, the hit with most positives would be decided to be the matching sequence hit.

Preferred framework sequences for use in the antibodies of the disclosure are those that are structurally similar to the framework sequences used by selected antibodies of the disclosure, e.g., similar to the $V_H$ 2-05 framework sequences (SEQ ID NO: 66) and/or the $V_H$ 2-70 framework sequences (SEQ ID NO: 67) and/or the $V_H$ 4-59 framework sequences (SEQ ID NO: 68) and/or the $V_H$ 3-20 framework sequences (SEQ ID NO: 69) and/or the $V_H$ 3-33 framework sequences (SEQ ID NO: 99) and/or the $V_K$ A27 framework sequences (SEQ ID NO: 70) and/or the $V_K$ L18 framework sequences (SEQ ID NO: 71) and/or the $V_K$ L15 framework sequences (SEQ ID NO: 72) and/or the $V_K$ 04 framework sequences (SEQ ID NO: 100) used by preferred monoclonal antibodies of the disclosure. The $V_H$ CDR1, CDR2, and CDR3 sequences, and the $V_K$ CDR1, CDR2, and CDR3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the $V_H$ and/or $V_K$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations may be amino acid substitutions, additions or deletions, but are preferably substitutions. Moreover, typically no more than one, two, three, four or five residues within a CDR region are altered.

Accordingly, in another embodiment, the disclosure provides isolated anti-BTLA monoclonal antibodies, or antigen binding portions thereof, comprising a heavy chain variable region comprising: (a) a $V_H$ CDR1 region comprising an amino acid sequence selected from the group consisting of SEQ ID NOs: 14, 15, 16, 17, 18, 19, 77, and 87, or an amino acid sequence having one, two, three, four or five amino acid substitutions, deletions or additions as compared to SEQ ID NOs: 14, 15, 16, 17, 18, 19, 77, and 87; (b) a $V_H$ CDR2 region comprising an amino acid sequence selected from the group consisting of SEQ ID NOs: 20, 21, 22, 23, 24, 25, 78, and 88, or an amino acid sequence having one, two, three, four or five amino acid substitutions, deletions or additions as compared to SEQ ID NOs: 20, 21, 22, 23, 24, 25, 78, and 88; (c) a $V_H$ CDR3 region comprising an amino acid sequence selected from the group consisting of SEQ ID NOs: 26, 27, 28, 29, 30, 31, 79, and 89, or an amino acid sequence having one, two, three, four or five amino acid substitutions, deletions or additions as compared to SEQ ID NOs: 26, 27, 28, 29, 30, 31, 79, and 89; (d) a $V_K$ CDR1 region comprising an amino acid sequence selected from the group consisting of SEQ ID NOs: 32, 33, 34, 35, 36, 37, 38, 80, 90, and 95, or an amino acid sequence having one, two, three, four or five amino acid substitutions, deletions or additions as compared to SEQ ID NOs: 32, 33, 34, 35, 36, 37, 38, 80, 90, and 95; (e) a $V_K$ CDR2 region comprising an amino acid sequence selected from the group consisting of SEQ ID NOs: 39, 40, 41, 42, 43, 44, 45, 81, 91, and 96, or an amino acid sequence having one, two, three, four or five amino acid substitutions, deletions or additions as compared to SEQ ID NOs: 39, 40, 41, 42, 43, 44, 45, 81, 91, and 96; and (f) a $V_K$ CDR3 region comprising an amino acid sequence selected from the group consisting of SEQ ID NOs: 46, 47, 48, 49, 50, 51, 52, 82, 92, and 97, or an amino acid sequence having one, two, three, four or five amino acid substitutions, deletions or additions as compared to SEQ ID NOs: 46, 47, 48, 49, 50, 51, 52, 82, 92, and 97.

Engineered antibodies of the disclosure include those in which modifications have been made to framework residues within $V_H$ and/or $V_K$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived.

For example, Table 1 below shows a number of amino acid changes in the framework regions of the anti-BTLA antibodies 1B4, E4H9, 3C2, 3C2a, 6A5, 11E2, E8D9, 10H6, 10H6a and 4C9 that differ from the parent germline sequence. To return one or more of the amino acid residues in the framework region sequences to their germline configuration, the somatic mutations can be "backmutated" to the germline sequence by, for example, site-directed mutagenesis or PCR-mediated mutagenesis.

The alignment of $V_H$ region for 1B4 against the parent germline $V_H$ 2-05 amino acid sequence is shown in FIG. 7. The alignment of $V_k$ region for 1B4 against the parent germline $V_k$ A27 amino acid sequence is shown in FIG. 8. The alignment of $V_H$ region for E4H9 against the parent germline $V_H$ 2-70 amino acid sequence is shown in FIG. 9. The alignment of $V_k$ region for E4H9 against the parent germline $V_k$ A27 amino acid sequence is shown in FIG. 10. The alignment of $V_H$ region for 3C2 against the parent germline $V_H$ 4-59 amino acid sequence is shown in FIG. 11. The alignment of $V_k$ region for 3C2 against the parent germline $V_k$ L18 amino acid sequence is shown in FIG. 12. The alignment of $V_k$ region for 3C2a against the parent germline $V_k$ L15 amino acid sequence is shown in FIG. 13. The alignment of $V_H$ region for 6A5 against the parent germline $V_H$ 2-05 amino acid sequence is shown in FIG. 14. The alignment of $V_k$ region for 6A5 against the parent germline $V_k$ A27 amino acid sequence is shown in FIG. 15. The alignment of $V_H$ region for 11E2 against the parent germline $V_H$ 3-20 amino acid sequence is shown in FIG. 16. The alignment of $V_k$ region for 11E2 against the parent germline $V_k$ L15 amino acid sequence is shown in FIG. 17. The alignment of $V_H$ region for E8D9 against the parent germline $V_H$ 2-05 amino acid sequence is shown in FIG. 18. The alignment of $V_k$ region for E8D9 against the parent germline $V_k$ A27 amino acid sequence is shown in FIG. 19. The alignment of $V_H$ region for 10H6 against the parent germline $V_H$ 3-33 amino acid sequence is shown in FIG. 22. The alignment of $V_k$ region for 10H6 against the parent germline $V_k$ 04 amino acid sequence is shown in FIG. 23. The alignment of $V_k$ region for 10H6a against the parent germline $V_k$ 04 A27 amino acid sequence is shown in FIG. 24. The alignment of $V_H$ region for 4C9 against the parent germline $V_H$ 2-05 amino acid sequence is shown in FIG. 26. The alignment of $V_k$ region for 4C9 against the parent germline $V_k$ A27 amino acid sequence is shown in FIG. 27.

TABLE 1

Modifications to antibodies 1B4, E4H9, 3C2, 6A5, 11E2 from the germline configuration.

| Anti-BTLA Ab | Amino acid position | Amino acid of antibody | Original amino acid of germline configuration |
|---|---|---|---|
| 1B4 $V_H$ | 30 | N | S |
|  | 72 | S | T |
| E4H9 $V_H$ | 86 | D | N |
| 3C2 $V_H$ | 24 | I | V |
|  | 69 | M | I |
|  | 72 | E | D |
| 6A5 $V_H$ | 85 | A | T |
| 11E2 $V_H$ | 12 | I | V |
|  | 91 | S | T |
|  | 95 | Y | H |
| 10H6 $V_H$ | 33 | D | G |
|  | 50 | A | V |
|  | 53 | N | Y |
| 10H6a $V_k$ | 32 | I | S |
| 4C9 $V_H$ | 37 | A | G |
|  | 56 | D | N |
|  | 85 | S | T |
| 4C9 $V_k$ | 32 | T | S |
|  | 35 | V | A |

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the disclosure may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the disclosure may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al.

The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγR1, FcγRII, FcγRIII and FcRn have been mapped and variants with improved binding have been described (see Shields, R. L. et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their carbohydrates. The Ms704, Ms705, and Ms709 FUT8$^{-/-}$ cell lines were created by the targeted disruption of the FUT8 gene in CHO/DG44 cells using two replacement vectors (see U.S. Patent Publication No. 20040110704 by Yamane et al. and Yamane-Ohnuki et al. (2004) *Biotechnol Bioeng* 87:614-22). As another example, EP 1,176,195 by Hanai et al. describes a cell line with a functionally disrupted FUT8 gene, which encodes a fucosyl transferase, such that antibodies expressed in such a cell line exhibit hypofucosylation by reducing or eliminating the alpha 1,6 bond-related enzyme. Hanai et al. also describe cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) *J. Biol. Chem.* 277:26733-26740). PCT Publication WO 99/54342 by Umana et al. describes cell lines engineered to express glycoprotein-modifying glycosyl transferases (e.g., beta(1,4)—N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180). Alternatively, the fucose residues of the antibody may be cleaved off using a fucosidase enzyme. For example, the fucosidase alpha-L-fucosidase removes fucosyl residues from antibodies (Tarentino, A. L. et al. (1975) *Biochem.* 14:5516-23).

Another modification of the antibodies herein that is contemplated by the disclosure is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the disclosure. See for example, EP 0 154 316 by Nishimura et al. and EP 0 401 384 by Ishikawa et al.

Methods of Engineering Antibodies

As discussed above, the anti-BTLA antibodies having $V_H$ and $V_K$ sequences disclosed herein can be used to create new anti-BTLA antibodies by modifying the VH and/or $V_K$ sequences, or the constant region(s) attached thereto. Thus, in another aspect of the disclosure, the structural features of an anti-BTLA antibody of the disclosure, e.g. 1B4, E4H9, 3C2, 3C2a, 6A5, 11E2, or E8D9, are used to create structurally related anti-BTLA antibodies that retain at least one functional property of the antibodies of the disclosure, such as binding to human BTLA. For example, one or more CDR regions of 1B4, E4H9, 3C2, 3C2a, 6A5, 11E2, or E8D9, or mutations thereof, can be combined recombinantly with known framework regions and/or other CDRs to create additional, recombinantly-engineered, anti-BTLA antibodies of the disclosure, as discussed above. Other types of modifications include those described in the previous section. The starting material for the engineering method is one or more of the $V_H$ and/or $V_K$ sequences provided herein, or one or more CDR regions thereof. To create the engineered antibody, it is not necessary to actually prepare (i.e., express as a protein) an antibody having one or more of the $V_H$ and/or $V_K$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the disclosure provides a method for preparing an anti-BTLA antibody comprising:

(a) providing: (i) a heavy chain variable region antibody sequence comprising a CDR1 sequence selected from the group consisting of SEQ ID NOs: 14, 15, 16, 17, 18, 19, 77, and 87, a CDR2 sequence selected from the group consisting of SEQ ID NOs: 20, 21, 22, 23, 24, 25, 78, and 88, and/or a CDR3 sequence selected from the group consisting of SEQ ID NOs: 26, 27, 28, 29, 30, 31, 79, and 89; and/or (ii) a light chain variable region antibody sequence comprising a CDR1 sequence selected from the group consisting of SEQ ID NOs: 32, 33, 34, 35, 36, 37, 38, 80, 90, and 95, a CDR2 sequence selected from the group consisting of SEQ ID NOs: 39, 40, 41, 42, 43, 44, 45, 81, 91, and 96, and/or a CDR3 sequence selected from the group consisting of SEQ ID NOs: 46, 47, 48, 49, 50, 51, 52, 82, 92, and 97;

(b) altering at least one amino acid residue within the heavy chain variable region antibody sequence and/or the light chain variable region antibody sequence to create at least one altered antibody sequence; and (c) expressing the altered antibody sequence as a protein.

Standard molecular biology techniques can be used to prepare and express the altered antibody sequence.

Preferably, the antibody encoded by the altered antibody sequence(s) is one that retains one, some or all of the functional properties of the anti-BTLA antibodies described herein, which functional properties include, but are not limited to:

(a) the antibody binds to human BTLA with a $K_D$ of $1 \times 10^{-7}$ M or less;

(b) the antibody does not substantially bind to human TrkB, PD-1, CD28, CTLA-4 or ICOS;

(c) the antibody inhibits the binding of HVEM to BTLA;

(d) the antibody stimulates immune responses;

(e) the antibody stimulates antibody responses;

(f) the antibody inhibits tumor cell growth in vivo.]

In other embodiments, the antibodies inhibit or suppress immune response.

The functional properties of the altered antibodies can be assessed using standard assays available in the art and/or described herein, such as those set forth in the Examples (e.g., flow cytometry, binding assays).

In certain embodiments of the methods of engineering antibodies of the disclosure, mutations can be introduced randomly or selectively along all or part of an anti-BTLA antibody coding sequence and the resulting modified anti-BTLA antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies of the Disclosure

Another aspect of the disclosure pertains to nucleic acid molecules that encode the antibodies of the disclosure. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid of the disclosure can be, for example, DNA or RNA and may or may not contain intronic sequences. In a preferred embodiment, the nucleic acid is a cDNA molecule.

Nucleic acids of the disclosure can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Preferred nucleic acids molecules of the disclosure are those encoding the VH and VL sequences of the 1B4, E4H9, 3C2, 3C2a, 6A5, 11E2, E8D9, 10H6, 10H6a or 4C9 monoclonal antibodies. DNA sequences encoding the VH sequences of 1B4, E4H9, 3C2, 6A5, 11E2, E8D9, 10H6 and 4C9 are shown in SEQ ID NOs: 53, 54, 55, 56, 56, 58, 83 and 93, respectively. DNA sequences encoding the VL sequences of 1B4, E4H9, 3C2, 3C2a, 6A5, 11E2, E8D9, 10H6, 10H6a or 4C9 are shown in SEQ ID NOs: 59, 60, 61, 62, 63, 64, 65, 84, 98, and 94, respectively.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly_4-Ser)_3$, such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., (1990) *Nature* 348:552-554).

Production of Monoclonal Antibodies of the Disclosure

Monoclonal antibodies (mAbs) of the present disclosure can be produced by a variety of techniques, including conventional monoclonal antibody methodology e.g., the standard somatic cell hybridization technique of Kohler and Milstein (1975) *Nature* 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies of the present disclosure can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In a preferred embodiment, the antibodies of the disclosure are human monoclonal antibodies. Such human monoclonal antibodies directed against BTLA can be generated using transgenic or transchromosomic mice carrying parts of the human immune system rather than the mouse system. These transgenic and transchromosomic mice include mice referred to herein as HuMAb mice and KM Mice™, respectively, and are collectively referred to herein as "human Ig mice."

The HuMAb Mouse® (Medarex, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) *Nature* 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol.* 13: 65-93, and Harding, F. and Lonberg, N. (1995) *Ann. N.Y. Acad. Sci.* 764:536-546). The preparation and use of HuMab mice, and the genomic modifications carried by such mice, is further described in Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Taylor, L. et al. (1994) International Immunology 6: 579-591; and Fishwild, D. et al. (1996) *Nature Biotechnology* 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies of the disclosure can be raised using a mouse that carries human immunoglobulin sequences on transgenes and transchomosomes, such as a mouse that carries a human heavy chain transgene and a human light chain transchromosome. Such mice, referred to herein as "KM Mice™", are described in detail in PCT Publication WO 02/43478 to Ishida et al.

Still further, alternative transgenic animal systems expressing human immunoglobulin genes are available in the art and can be used to raise anti-BTLA antibodies of the disclosure. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-BTLA antibodies of the disclosure. For example, mice carrying both a human heavy chain transchromosome and a human light chain tranchromosome, referred to as "TC mice" can be used; such mice are described in Tomizuka et al. (2000) *Proc. Natl. Acad. Sci. USA* 97:722-727. Furthermore, cows carrying human heavy and light chain transchromosomes have been described in the art (Kuroiwa et al. (2002) *Nature Biotechnology* 20:889-894) and can be used to raise anti-BTLA antibodies of the disclosure.

Human monoclonal antibodies of the disclosure can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the disclosure can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunization of Human Ig Mice

When human Ig mice are used to raise human antibodies of the disclosure, such mice can be immunized with a purified or enriched preparation of BTLA antigen and/or recombinant BTLA, or an BTLA fusion protein, as described by Lonberg, N. et al. (1994) Nature 368(6474): 856-859; Fishwild, D. et al. (1996) *Nature Biotechnology* 14: 845-851; and PCT Publication WO 98/24884 and WO 01/14424. Preferably, the mice will be 6-16 weeks of age upon the first infusion. For example, a purified or recombinant preparation (5-50 µg) of BTLA antigen can be used to immunize the human Ig mice intraperitoneally.

Detailed procedures to generate fully human monoclonal antibodies to BTLA are described in Example 1 below. Cumulative experience with various antigens has shown that the transgenic mice respond when initially immunized intraperitoneally (IP) with antigen in Ribi (Sigma M 6536: MPL+ TDM), followed by every other week IP immunizations (up to a total of 6) with antigen in adjuvant. However, adjuvants other than Ribi (Freund's complete and Freund's incomplete adjuvants) are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below), and mice with sufficient titers of anti-BTLA human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. In addition, both HCo7 and HCol2 transgene can be bred together into a single mouse having two different human heavy chain transgenes (HCo7/HCo12). Alternatively or additionally, the KM Mouse™ strain can be used, as described in Example 1.

Generation of Hybridomas Producing Human Monoclonal Antibodies

To generate hybridomas producing human monoclonal antibodies of the disclosure, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to P3x63-Ag8.653 nonsecreting mouse myeloma cells (ATCC, CRL 1580) with 50% PEG. Cells are plated at approximately $2 \times 10^5$ in flat bottom microtiter plates, followed by a two week incubation in selective medium containing 10% FBS, 3-5% Origen (IGEN), OPI supplement (Sigma O 5003: $1.1 \times 10^{-3}$ M Oxalo acetic acid, $4.5 \times 10^{-4}$ M sodium Pyruvate, and 24 international units/L Bovine Insulin), 4 mM L-glutamine, 0.055 mM 2-mercaptoethanol, 50 units/ml penicillin, 50 mg/ml streptomycin, and 1×HAT (Sigma H 0262). After approximately two weeks, cells can be cultured in medium in which the HAT is replaced with HT (Sigma H 0137). Individual wells can then be screened by ELISA for human monoclonal IgG antibodies. The antibody secreting hybridomas can be replated, screened again, and if still positive for human IgG, the hybridomas can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

Generation of Transfectomas Producing Monoclonal Antibodies

Antibodies of the disclosure also can be produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_K$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or (3-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) Mol. Cell. Biol. 8:466-472).

In addition to the antibody chain genes and regulatory sequences, the recombinant expression vectors of the disclosure may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr—host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the disclosure in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) Immunology Today 6:12-13).

Preferred mammalian host cells for expressing the recombinant antibodies of the disclosure include Chinese Hamster Ovary (CHO cells) (including dhfr—CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Characterization of Antibody Binding to Antigen

Antibodies of the disclosure can be tested for binding to BTLA by, for example, standard ELISA. Briefly, microtiter plates are coated with purified BTLA at 1 μg/ml in PBS, and then blocked with 1% bovine serum albumin in PBS/tween. Dilutions of antibody (e.g., dilutions of plasma from BTLA-immunized mice) are added to each well and incubated for 1-2 hours at ambient temperature. The plates are washed with PBS/Tween and then incubated with secondary reagent (e.g., for human antibodies, a goat-anti-human IgG Fc-specific polyclonal reagent) conjugated to alkaline phosphatase for 1 hour at 37° C. After washing, the plates are developed with pNPP substrate (1 mg/ml), and analyzed at OD of 405-650. Preferably, mice which develop the highest titers will be used for fusions.

An ELISA assay as described above can also be used to screen for hybridomas that show positive reactivity with BTLA immunogen. Hybridomas that bind with high avidity to BTLA are subcloned and further characterized. One clone from each hybridoma, which retains the reactivity of the parent cells (by ELISA), can be chosen for making a 5-10 vial cell bank stored at −140° C., and for antibody purification.

To purify anti-BTLA antibodies, selected hybridomas can be grown to a volume of 1-2 L in tissue culture flasks or spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

To determine if the selected anti-BTLA monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using BTLA coated-ELISA plates as described above. Biotinylated mAb binding can be detected with a strep-avidin-alkaline phosphatase probe. Additionally, similar competition studies can be done by FACS on BTLA-CHO cells. Binding of biotin labeled BTLA antibodies to cells can be detected with a streptavidin-phycoerythrin probe.

To determine the isotype of purified antibodies, isotype ELISAs can be performed using reagents specific for antibodies of a particular isotype. For example, to determine the isotype of a human monoclonal antibody, wells of microtiter plates can be coated with 1 µg/ml of anti-human immunoglobulin overnight at 4° C. After blocking with 1% BSA, the plates are reacted with 1 µg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

FACS assays are used to verify that antibodies of the disclosure are binding to native BTLA expressed on cells. Briefly, dilutions of antibody in PBS1% BSA plus 0.5% sodium azide (FACS buffer) are incubated with transfected CHO cells expressing BTLA ($10^5$ cells) for 30 minutes at 4° C. Cells are washed twice by centrifugation, aspiration of supernatant, and addition of fresh FACS buffer. Antibody binding to BTLA on cells is detected by incubating the cells in PE labeled goat anti-human IgG (Fc specific) antibody for 30 min at 4° C., washing the cells 2× as above, and analyzing by FACS.

Anti-BTLA human IgGs can be further tested for reactivity with BTLA antigen by Western blotting. Briefly, BTLA can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Antibody Physical Properties

The antibodies of the present disclosure may be further characterized by the various physical properties of the anti-BTLA antibodies. Various assays may be used to detect and/or differentiate different classes of antibodies based on these physical properties.

In some embodiments, antibodies of the present disclosure may contain one or more glycosylation sites in either the light or heavy chain variable region. The presence of one or more glycosylation sites in the variable region may result in increased immunogenicity of the antibody or an alteration of the pK of the antibody due to altered antigen binding (Marshall et al (1972) *Annu Rev Biochem* 41:673-702; Gala F A and Morrison S L (2004) *J Immunol* 172:5489-94; Wallick et al (1988) *J Exp Med* 168:1099-109; Spiro R G (2002) *Glycobiology* 12:43R-56R; Parekh et al (1985) *Nature* 316:452-7; Mimura et al. (2000) *Mol Immunol* 37:697-706). Glycosylation has been known to occur at motifs containing an N-X-S/T sequence. Variable region glycosylation may be tested using a Glycoblot assay, which cleaves the antibody to produce a Fab, and then tests for glycosylation using an assay that measures periodate oxidation and Schiff base formation. Alternatively, variable region glycosylation may be tested using Dionex light chromatography (Dionex-LC), which cleaves saccharides from a Fab into monosaccharides and analyzes the individual saccharide content. In some instances, it is preferred to have an anti-BTLA antibody that does not contain variable region glycosylation. This can be achieved either by selecting antibodies that do not contain the glycosylation motif in the variable region or by mutating residues within the glycosylation motif using standard techniques well known in the art.

In a preferred embodiment, the antibodies of the present disclosure do not contain asparagine isomerism sites. A deamidation or isoaspartic acid effect may occur on N-G or D-G sequences, respectively. The deamidation or isoaspartic acid effect results in the creation of isoaspartic acid which decreases the stability of an antibody by creating a kinked structure off a side chain carboxy terminus rather than the main chain. The creation of isoaspartic acid can be measured using an iso-quant assay, which uses a reverse-phase HPLC to test for isoaspartic acid.

Each antibody will have a unique isoelectric point (pI), but generally antibodies will fall in the pH range of between 6 and 9.5. The pI for an IgG1 antibody typically falls within the pH range of 7-9.5 and the pI for an IgG4 antibody typically falls within the pH range of 6-8. Antibodies may have a pI that is outside this range. Although the effects are generally unknown, there is speculation that antibodies with a pI outside the normal range may have some unfolding and instability under in vivo conditions. The isoelectric point may be tested using a capillary isoelectric focusing assay, which creates a pH gradient and may utilize laser focusing for increased accuracy (Janini et al (2002) *Electrophoresis* 23:1605-11; Ma et al. (2001) *Chromatographia* 53:S75-89; Hunt et al (1998) *J Chromatogr A* 800:355-67). In some instances, it is preferred to have an anti-BTLA antibody that contains a pI value that falls in the normal range. This can be achieved either by selecting antibodies with a pI in the normal range, or by mutating charged surface residues using standard techniques well known in the art.

Each antibody will have a melting temperature that is indicative of thermal stability (Krishnamurthy Rand Manning M C (2002) *Curr Pharm Biotechnol* 3:361-71). A higher thermal stability indicates greater overall antibody stability in vivo. The melting point of an antibody may be measure using techniques such as differential scanning calorimetry (Chen et al (2003) *Pharm Res* 20:1952-60; Ghirlando et al (1999) *Immunol Lett* 68:47-52). $T_{M1}$ indicates the temperature of the initial unfolding of the antibody. $T_{M2}$ indicates the temperature of complete unfolding of the antibody. Generally, it is preferred that the $T_{M1}$ of an antibody of the present disclosure is greater than 60° C., preferably greater than 65° C., even more preferably greater than 70° C. Alternatively, the thermal stability of an antibody may be measure using circular dichroism (Murray et al. (2002) *J. Chromatogr Sci* 40:343-9).

In a preferred embodiment, antibodies are selected that do not rapidly degrade. Fragmentation of an anti-BTLA antibody may be measured using capillary electrophoresis (CE) and MALDI-MS, as is well understood in the art (Alexander A J and Hughes D E (1995) *Anal Chem* 67:3626-32).

In another preferred embodiment, antibodies are selected that have minimal aggregation effects. Aggregation may lead to triggering of an unwanted immune response and/or altered or unfavorable pharmacokinetic properties. Generally, antibodies are acceptable with aggregation of 25% or less, preferably 20% or less, even more preferably 15% or less, even more preferably 10% or less and even more preferably 5% or less. Aggregation may be measured by several techniques well known in the art, including size-exclusion column (SEC) high performance liquid chromatography (HPLC), and light scattering to identify monomers, dimers, trimers or multimers.

Immunoconjugates

In another aspect, the present disclosure features an anti-BTLA antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to an antibody of the disclosure include duocarmycins, calicheamicins, maytansines and auristatins, and derivatives thereof. An example of a calicheamicin antibody conjugate is commercially available (Mylotarg™; Wyeth-Ayerst).

Cytotoxins can be conjugated to antibodies of the disclosure using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) Adv. Drug Deliv. Rev. 55:199-215; Trail, P. A. et al. (2003) Cancer Immunol. Immunother. 52:328-337; Payne, G. (2003) Cancer Cell 3:207-212; Allen, T. M. (2002) Nat. Rev. Cancer 2:750-763; Pastan, I. and Kreitman, R. J. (2002) Curr. Opin. Investig. Drugs 3:1089-1091; Senter, P. D. and Springer, C. J. (2001) Adv. Drug Deliv. Rev. 53:247-264.

Antibodies of the present disclosure also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$ and lutetium$^{177}$. Method for preparing radioimmunconjugates are established in the art. Examples of radioimmunoconjugates are commercially available, including Zevalin™ (IDEC Pharmaceuticals) and Bexxar™ (Corixa Pharmaceuticals), and similar methods can be used to prepare radioimmunoconjugates using the antibodies of the disclosure.

The antibody conjugates of the disclosure can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Bispecific Molecules

In another aspect, the present disclosure features bispecific molecules comprising an anti-BTLA antibody, or a fragment thereof, of the disclosure. An antibody of the disclosure, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the disclosure may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the disclosure, an antibody of the disclosure can be functionally linked (e.g., by chemical coupling, genetic fusion, non-covalent association or otherwise) to one or more other binding molecules, such as another antibody, antibody fragment, peptide or binding mimetic, such that a bispecific molecule results.

Accordingly, the present disclosure includes bispecific molecules comprising at least one first binding specificity for BTLA and a second binding specificity for a second target epitope. In a particular embodiment of the disclosure, the second target epitope is an Fc receptor, e.g., human FcγRI (CD64) or a human Fox receptor (CD89). Therefore, the disclosure includes bispecific molecules capable of binding both to FcγR or FcαR expressing effector cells (e.g., monocytes, macrophages or polymorphonuclear cells (PMNs)), and to target cells expressing BTLA. These bispecific molecules target BTLA expressing cells to effector cell and trigger Fc receptor-mediated effector cell activities, such as phagocytosis of BTLA expressing cells, antibody dependent cell-mediated cytotoxicity (ADCC), cytokine release, or generation of superoxide anion.

In an embodiment of the disclosure in which the bispecific molecule is multispecific, the molecule can further include a third binding specificity, in addition to an anti-Fc binding specificity and an anti-BTLA binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the $F_C$ receptor or target cell antigen. The "anti-enhancement factor portion" can bind an $F_C$ receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g. via CD2, CD3, CD8, CD28, CD4, CD40, ICAM-1 or other immune cell that results in an increased immune response against the target cell).

In one embodiment, the bispecific molecules of the disclosure comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

In one embodiment, the binding specificity for an Fcγ receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), Fcγ RII (CD32), and FcγRIII (CD16). In one preferred embodiment, the Fcγ receptor a human high affinity FcγRI. The human FcγRI is a 72 kDa molecule, which shows high affinity for monomeric IgG ($10^8$-$10^9 M^{-1}$).

The production and characterization of certain preferred anti-Fcγ monoclonal antibodies are described by Fanger et al. in PCT Publication WO 88/00052 and in U.S. Pat. No. 4,954,617, the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this disclosure are mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The production and characterization of the H22 antibody is described in Graziano, R. F. et al. (1995) *J. Immunol.* 155 (10): 4996-5002 and PCT Publication WO 94/10332. The H22 antibody producing cell line was deposited at the American Type Culture Collection under the designation HA022CL1 and has Accession No. CRL 11177.

In still other preferred embodiments, the binding specificity for an Fc receptor is provided by an antibody that binds to a human IgA receptor, e.g., an Fc-alpha receptor (Fc αRI (CD89)), the binding of which is preferably not blocked by human immunoglobulin A (IgA). The term "IgA receptor" is intended to include the gene product of one α-gene (Fc αRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity ($\approx 5 \times 10^7 M^{-1}$) for both IgA1 and IgA2, which is increased upon exposure to cytokines such as G-CSF or GM-CSF (Morton, H. C. et al. (1996) *Critical Reviews in Immunology* 16:423-440). Four FcαRI-specific monoclonal antibodies, identified as A3, A59, A62 and A77, which bind FcαRI outside the IgA ligand binding domain, have been described (Monteiro, R. C. et al. (1992) *J. Immunol.* 148: 1764).

FcαRI and FcγRI are preferred trigger receptors for use in the bispecific molecules of the disclosure because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); (4) mediate enhanced antigen presentation of antigens, including self-antigens, targeted to them.

While human monoclonal antibodies are preferred, other antibodies which can be employed in the bispecific molecules of the disclosure are murine, chimeric and humanized monoclonal antibodies.

The bispecific molecules of the present disclosure can be prepared by conjugating the constituent binding specificities, e.g., the anti-FcR and anti-BTLA binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio) propionate (SPDP), and sulfosuccinimidyl 4-(N-maleimidomethyl)cyclohaxane-1-carboxylate (sulfo-SMCC) (see e.g., Karpovsky et al. (1984) *J. Exp. Med.* 160: 1686; Liu, M A et al. (1985) *Proc. Natl. Acad. Sci. USA* 82:8648). Other methods include those described in Paulus (1985) Behring Ins. Mitt. No. 78, 118-132; Brennan et al. (1985) *Science* 229:81-83), and Glennie et al. (1987) *J. Immunol.* 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand× Fab fusion protein. A bispecific molecule of the disclosure can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

Pharmaceutical Compositions

In another aspect, the present disclosure provides a composition, e.g., a pharmaceutical composition, containing one or a combination of monoclonal antibodies, or antigen-binding portion(s) thereof, of the present disclosure, formulated together with a pharmaceutically acceptable carrier. Such compositions may include one or a combination of (e.g., two or more different) antibodies, or immunoconjugates or bispecific molecules of the disclosure. For example, a pharmaceutical composition of the disclosure can comprise a combination of antibodies (or immunoconjugates or bispecifics) that bind to different epitopes on the target antigen or that have complementary activities.

Pharmaceutical compositions of the disclosure also can be administered in combination therapy, i.e., combined with other agents. For example, the combination therapy can include an anti-BTLA antibody of the present disclosure combined with at least one other anti-inflammatory or immunosuppressant agent. Examples of therapeutic agents that can be used in combination therapy are described in greater detail below in the section on uses of the antibodies of the disclosure.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

The pharmaceutical compounds of the disclosure may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the disclosure is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the disclosure are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-BTLA antibody of the disclosure include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-BTLA antibody of the disclosure preferably results in a decrease in severity of disease symptoms, an increase in frequency and duration of disease symptom-free periods, or a prevention of impairment or disability due to the disease affliction. For example, for the treatment of tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present disclosure can be administered via one or more routes of administration using one or more of a variety of methods known in the art. As will be appreciated by the skilled artisan, the route and/or mode of administration will vary depending upon the desired results. Preferred routes of administration for antibodies of the disclosure include intravenous, intramuscular, intradermal, intraperitoneal, subcutaneous, spinal or other parenteral routes of administration, for example by injection or infusion.

The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the disclosure can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition of the disclosure can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present disclosure include: U.S. Pat. No. 4,487,603, which discloses an implantable micro-infusion pump for dispensing medication at a controlled rate; U.S. Pat. No. 4,486,194, which discloses, a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the human monoclonal antibodies of the disclosure can be formulated to ensure proper distribution in vivo, For example, the blood-brain barrier (BBB) excludes many highly hydrophilic compounds. To ensure that the therapeutic compounds of the disclosure cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

Uses and Methods of the Disclosure

The antibodies, antibody compositions and methods of the present disclosure have numerous in vitro and in vivo utilities involving, for example, detection of BTLA or enhancement of immune response by blockade of BTLA. In some embodiments, the antibodies suppress immune response by binding BTLA. In this embodiment the antibody functions as an agonist. In a preferred embodiment, the antibodies of the present disclosure are human antibodies. For example, these molecules can be administered to cells in culture, in vitro or ex vivo, or to human subjects, e.g., in vivo, to enhance immunity in a variety of situations. Accordingly, in one aspect, the disclosure provides a method of modifying an immune response in a subject comprising administering to the subject the antibody, or antigen-binding portion thereof, of the disclosure such that the immune response in the subject is modified. Preferably, the response is enhanced, stimulated or upregulated.

As used herein, the term "subject" is intended to include human and non-human animals. Non-human animals includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses. Preferred subjects include human patients in need of enhancement of an immune response. The methods are particularly suitable for treating human patients having a disorder that can be treated by augmenting the T-cell mediated immune response. In a particular embodiment, the methods are particularly suitable for treatment of cancer cells in vivo. To achieve antigen-specific enhancement of immunity, the anti-BTLA antibodies can be administered together with an antigen of interest. When antibodies to BTLA are administered together with another agent, the two can be administered in either order or simultaneously.

The disclosure further provides methods for detecting the presence of human BTLA antigen in a sample, or measuring the amount of human BTLA antigen, comprising contacting the sample, and a control sample, with a human monoclonal antibody, or an antigen binding portion thereof, which specifically binds to human BTLA, under conditions that allow for formation of a complex between the antibody or portion thereof and human BTLA. The formation of a complex is then detected, wherein a difference complex formation between the sample compared to the control sample is indicative the presence of human BTLA antigen in the sample.

Given the specific binding of the antibodies of the disclosure for BTLA, compared to CD28, ICOS and CTLA-4, the antibodies of the disclosure can be used to specifically detect BTLA expression on the surface of cells and, moreover, can be used to purify BTLA via immunoaffinity purification.

Cancer

Blockade of BTLA by antibodies can enhance the immune response to cancerous cells in the patient. The ligand for BTLA, HVEM, is TNFR family member and is inducible of some somatic tissues and in lymphoid cells, including T, B, NK, dendritic and myeloid cells. (Murphy et al., Nat. Reviews Immunology, 6, 671-681, 2006) Immune suppression induced by HVEM/BTLA interaction can be reversed by inhibiting the local interaction of BTLA to HVEM. (Watanabe et al., Nat. Immunol., 4, 670-679, 2003; Otsuki et al., BBRC 344, 1121-1127, 2006) In one aspect, the present disclosure relates to treatment of a subject in vivo using an anti-BTLA antibody such that growth of cancerous tumors is inhibited. An anti-BTLA antibody may be used alone to inhibit the growth of cancerous tumors. Alternatively, an anti- BTLA antibody may be used in conjunction with other immunogenic agents, standard cancer treatments, or other antibodies, as described below.

Accordingly, in one embodiment, the disclosure provides a method of inhibiting growth of tumor cells in a subject, comprising administering to the subject a therapeutically effective amount of an anti-BTLA antibody, or antigen-binding portion thereof. Preferably, the antibody is a human anti-BTLA antibody (such as any of the human anti-human BTLA antibodies described herein). Additionally or alternatively, the antibody may be a chimeric or humanized anti-BTLA antibody.

Preferred cancers whose growth may be inhibited using the antibodies of the disclosure include cancers typically responsive to immunotherapy. Non-limiting examples of preferred cancers for treatment include melanoma (e.g., metastatic malignant melanoma), renal cancer, prostate cancer, breast cancer, colon cancer and lung cancer. Examples of other cancers that may be treated using the methods of the disclosure include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present disclosure is also useful for treatment of metastatic cancers.

Optionally, antibodies to BTLA can be combined with an immunogenic agent, such as cancerous cells, purified tumor antigens (including recombinant proteins, peptides, and carbohydrate molecules), cells, and cells transfected with genes encoding immune stimulating cytokines (He et al (2004) *J. Immunol.* 173:4919-28). Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF (discussed further below).

In humans, some tumors have been shown to be immunogenic such as melanomas. It is anticipated that by raising the threshold of T cell activation by BTLA blockade, we may expect to activate tumor responses in the host.

BTLA blockade may be most effective when combined with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, Cancer: Principles and Practice of Oncology. Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci. U.S.A.* 90: 3539-43).

The study of gene expression and large scale gene expression patterns in various tumors has led to the definition of so called tumor specific antigens (Rosenberg, S A (1999) Immunity 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. BTLA blockade may be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al. (1994) Science 266: 2011-2013). (These somatic tissues may be protected from immune attack by various means). Tumor antigen may also be "neo-antigens" expressed in cancer cells because of somatic mutations that alter protein sequence or create fusion proteins between two unrelated sequences (ie. bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with BTLA blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) *Science* 269:1585-1588; Tamura, Y. et al. (1997) Science 278:117-120).

Dendritic cells (DC) are potent antigen presenting cells that can be used to prime antigen-specific responses. DC's can be produced ex vivo and loaded with various protein and peptide antigens as well as tumor cell extracts (Nestle, F. et al. (1998) *Nature Medicine* 4: 328-332). DCs may also be transduced by genetic means to express these tumor antigens as well. DCs have also been fused directly to tumor cells for the purposes of immunization (Kugler, A. et al. (2000) *Nature Medicine* 6:332-336). As a method of vaccination, DC immunization may be effectively combined with BTLA blockade to activate more potent anti-tumor responses.

BTLA blockade may also be combined with standard cancer treatments. BTLA blockade may be effectively combined with chemotherapeutic regimes. In these instances, it may be possible to reduce the dose of chemotherapeutic reagent administered (Mokyr, M. et al. (1998) *Cancer Research* 58: 5301-5304). An example of such a combination is an anti-BTLA antibody in combination with decarbazine for the treatment of melanoma. Another example of such a combination is an anti-BTLA antibody in combination with interleukin-2 (IL-2) for the treatment of melanoma. The scientific rationale behind the combined use of BTLA blockade and chemotherapy is that cell death, that is a consequence of the cytotoxic action of most chemotherapeutic compounds, should result in increased levels of tumor antigen in the antigen presentation pathway. Other combination therapies that may result in synergy with BTLA blockade through cell death are radiation, surgery, and hormone deprivation. Each of these protocols creates a source of tumor antigen in the host. Angiogenesis inhibitors may also be combined with BTLA blockade. Inhibition of angiogenesis leads to tumor cell death which may feed tumor antigen into host antigen presentation pathways.

BTLA blocking antibodies can also be used in combination with bispecific antibodies that target Fc alpha or Fc gamma receptor-expressing effectors cells to tumor cells (see, e.g., U.S. Pat. Nos. 5,922,845 and 5,837,243). Bispecific antibodies can be used to target two separate antigens. For example anti-Fc receptor/anti tumor antigen (e.g., Her-2/neu) bispecific antibodies have been used to target macrophages to sites of tumor. This targeting may more effectively activate tumor specific responses. The T cell arm of these responses would by augmented by the use of BTLA blockade. Alternatively, antigen may be delivered directly to DCs by the use of bispecific antibodies which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al. (1986) *J. Exp. Med.* 163: 1037-1050), IL-10 (Howard, M. & O'Garra, A. (1992) *Immunology Today* 13: 198-200), and Fas ligand (Hahne, M. et al. (1996) Science 274: 1363-1365). Antibodies to each of these entities may be used in combination with anti-BTLA to counteract the effects of the immunosuppressive agent and favor tumor immune responses by the host.

Other antibodies which may be used to activate host immune responsiveness can be used in combination with anti-BTLA. These include molecules on the surface of dendritic cells which activate DC function and antigen presentation. Anti-CD40 antibodies are able to substitute effectively for T cell helper activity (Ridge, J. et al. (1998) Nature 393: 474-478) and can be used in conjuction with BTLA antibodies (Ito, N. et al. (2000) *Immunobiology* 201 (5) 527-40). Activating antibodies to T cell costimulatory molecules such as CTLA-4 (e.g., U.S. Pat. No. 5,811,097), OX-40 (Weinberg, A. et al. (2000) *Immunol* 164: 2160-2169), 4-1BB (Melero, I. et al. (1997) *Nature Medicine* 3: 682-685 (1997), and ICOS (Hutloff, A. et al. (1999) *Nature* 397: 262-266) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. BTLA blockade can be used to increase the effectiveness of the donor engrafted tumor specific T cells.

There are also several experimental treatment protocols that involve ex vivo activation and expansion of antigen specific T cells and adoptive transfer of these cells into recipients in order to antigen-specific T cells against tumor (Greenberg, R. & Riddell, S. (1999) *Science* 285: 546-51). These methods may also be used to activate T cell responses to infectious agents such as CMV. Ex vivo activation in the presence of anti-BTLA antibodies may be expected to increase the frequency and activity of the adoptively transferred T cells.
Infectious Diseases Other methods of the disclosure are used to treat patients that have been exposed to particular toxins or pathogens. Accordingly, another aspect of the disclosure provides a method of treating an infectious disease in a subject comprising administering to the subject an anti-BTLA antibody, or antigen-binding portion thereof, such that the subject is treated for the infectious disease. Preferably, the antibody is a human anti-human BTLA antibody (such as any of the human anti-BTLA antibodies described herein). Additionally or alternatively, the antibody can be a chimeric or humanized antibody.

Similar to its application to tumors as discussed above, antibody mediated BTLA blockade can be used alone, or as an adjuvant, in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to HIV, Hepatitis (B, & C), Influenza, Herpes, *Giardia, Malaria, Leishmania, Staphylococcus aureus, Pseudomonas Aeruginosa*. BTLA blockade is particularly useful against established infections by agents such as HIV that present altered antigens over the course of the infections. These novel epitopes are recognized as foreign at the time of anti-human BTLA administration, thus provoking a strong T cell response that is not dampened by negative signals through BTLA.

Some examples of pathogenic viruses causing infections treatable by methods of the disclosure include HIV, hepatitis (B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the disclosure include chlamydia, rickettsial bacteria, mycobacteria, staphylococci, streptococci, pneumonococci, meningococci and conococci, *klebsiella, proteus, serratia*, pseudomonas, *legionella*, diphtheria, *salmonella*, bacilli, cholera, tetanus, botulism, anthrax, plague, leptospirosis, and Lymes disease bacteria.

Some examples of pathogenic fungi causing infections treatable by methods of the disclosure include *Candida* (albicans, krusei, glabrata, tropicalis, etc.), *Cryptococcus neoformans, Aspergillus* (fumigatus, niger, etc.), *Genus Mucorales* (mucor, absidia, rhizophus), *Sporothrix schenkii, Blastomyces dermatitidis, Paracoccidioides brasiliensis, Coccidioides immitis* and *Histoplasma capsulatum*.

Some examples of pathogenic parasites causing infections treatable by methods of the disclosure include *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi, Nippostrongylus brasiliensis*.

In all of the above methods, BTLA blockade can be combined with other forms of immunotherapy such as cytokine treatment (e.g., interferons, GM-CSF, G-CSF, IL-2), or bispecific antibody therapy, which provides for enhanced presentation of tumor antigens (see, e.g., Holliger (1993) *Proc. Natl. Acad. Sci. USA* 90:6444-6448; Poljak (1994) *Structure* 2:1121-1123).
Autoimmune Reactions Anti-BTLA antibodies may provoke and amplify autoimmune responses. Indeed, induction of anti-tumor responses using tumor cell and peptide vaccines reveals that many anti-tumor responses involve anti-self reactivities (depigmentation observed in anti-CTLA-4+ GM-CSF-modified B16 melanoma in van Elsas et al. supra; depigmentation in Trp-2 vaccinated mice (Overwijk, W. et al. (1999) *Proc. Natl. Acad. Sci. U.S.A.* 96: 2982-2987); autoimmune prostatitis evoked by TRAMP tumor cell vaccines (Hurwitz, A. (2000) supra), melanoma peptide antigen vaccination and vitilago observed in human clinical trials (Rosenberg, S A and White, D E (1996) *J. Immunother Emphasis Tumor Immunol* 19 (1): 81-4).

Therefore, it is possible to consider using anti-BTLA blockade in conjunction with various self proteins in order to devise vaccination protocols to efficiently generate immune responses against these self proteins for disease treatment. For example, Alzheimers disease involves inappropriate accumulation of Aβ peptide in amyloid deposits in the brain; antibody responses against amyloid are able to clear these amyloid deposits (Schenk et al., (1999) *Nature* 400: 173-177).

Other self proteins may also be used as targets such as IgE for the treatment of allergy and asthma, and TNFα for rhematoid arthritis. Finally, antibody responses to various hormones may be induced by the use of anti-BTLA antibody. Neutralizing antibody responses to reproductive hormones may be used for contraception. Neutralizing antibody response to hormones and other soluble factors that are required for the growth of particular tumors may also be considered as possible vaccination targets.

Analogous methods as described above for the use of anti-BTLA antibody can be used for induction of therapeutic autoimmune responses to treat patients having an inappropriate accumulation of other self-antigens, such as amyloid deposits, including Aβ in Alzheimer's disease, cytokines such as TNFα, and IgE.

Also, in some embodiment, agonism can also be used to decrease an autoimmune response. Anti BTLA antibodies are useful as agonists, thereby suppressing immune responses otherwise mediated by immune cells expressing BTLA. Some examples of diseases that can be treated using such agonist antibodies include autoimmune disease, transplant rejection, and inflammation.

Vaccines

Anti-BTLA antibodies may be used to stimulate antigen-specific immune responses by coadministration of an anti-BTLA antibody with an antigen of interest (e.g., a vaccine). Accordingly, in another aspect the disclosure provides a method of enhancing an immune response to an antigen in a subject, comprising administering to the subject: (i) the antigen; and (ii) an anti-BTLA antibody, or antigen-binding portion thereof, such that an immune response to the antigen in the subject is enhanced. Preferably, the antibody is a human anti-human BTLA antibody (such as any of the human anti-BTLA antibodies described herein). Additionally or alternatively, the antibody can be a chimeric or humanized antibody. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

Suitable routes of administering the antibody compositions (e.g., human monoclonal antibodies, multispecific and bispecific molecules and immunoconjugates) of the disclosure in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, human anti-BTLA antibodies of the disclosure can be co-administered with one or other more therapeutic agents, e.g., a cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cis-platin bleomycin sulfate, carmustine, chlorambucil, decarbazine and cyclophosphamide hydroxyurea which, by themselves, are only effective at levels which are toxic or subtoxic to a patient. Cisplatin is intravenously administered as a 100 mg/dose once every four weeks and adriamycin is intravenously administered as a 60-75 mg/ml dose once every 21 days. Co-administration of the human anti-BTLA antibodies, or antigen binding fragments thereof, of the present disclosure with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Also within the scope of the present disclosure are kits comprising the antibody compositions of the disclosure (e.g., human antibodies, bispecific or multispecific molecules, or immunoconjugates) and instructions for use. The kit can further contain a least one additional reagent, or one or more additional human antibodies of the disclosure (e.g., a human antibody having a complementary activity which binds to an epitope in BTLA antigen distinct from the first human antibody). Kits typically include a label indicating the intended use of the contents of the kit. The term label includes any writing, or recorded material supplied on or with the kit, or which otherwise accompanies the kit.

The present disclosure is further illustrated by the following examples which should not be construed as further limiting. The contents of all figures and all references, patents and published patent applications cited throughout this application are expressly incorporated herein by reference.

EXAMPLES

Example 1

Generation of Human Monoclonal Antibodies Against BTLA

Antigen

Immunization protocols utilized as antigen both (i) a recombinant fusion protein comprising the extracellular portion of BTLA and (ii) membrane bound full-length BTLA. Both antigens were generated by recombinant transfection methods in a CHO cell line.

Transgenic HuMab and KM Mice™

Fully human monoclonal antibodies to BTLA were prepared using the HCo7 strain of HuMab transgenic mice and the KM strain of transgenic transchromosomic mice, each of which express human antibody genes. In each of these mouse strains, the endogenous mouse kappa light chain gene has been homozygously disrupted as described in Chen et al. (1993) *EMBO J.* 12:811-820 and the endogenous mouse heavy chain gene has been homozygously disrupted as described in Example 1 of PCT Publication WO 01/09187. Each of these mouse strains carries a human kappa light chain transgene, KCo5, as described in Fishwild et al. (1996) *Nature Biotechnology* 14:845-851. The HCo7 strain carries the HCo7 human heavy chain transgene as described in U.S. Pat. Nos. 5,545,806; 5,625,825; and 5,545,807. The KM strain contains the SC20 transchromosome as described in PCT Publication WO 02/43478.

HuMab and KM Immunizations:

To generate fully human monoclonal antibodies to BTLA, HuMab mice and KM Mice™ were immunized with purified recombinant BTLA fusion protein and BTLA-transfected CHO cells as antigen. General immunization schemes for HuMab mice are described in Lonberg, N. et al (1994) *Nature* 368(6474): 856-859; Fishwild, D. et al. (1996) *Nature Biotechnology* 14: 845-851 and PCT Publication WO 98/24884. A purified recombinant preparation (5-50 µg) of BTLA fusion protein antigen and $5-10\times10^6$ cells were used to immunize the HuMab mice and KM Mice™ intraperitonealy (Ip), or subcutaneously (Sc).

TABLE 2

Immuniaztion Schedule for BTLA KM Mice ™

| Mouse | BTLA-Ig* Day 0 | Cells**/ Ig-Ribi Day 7 | BTLA-Ig Day 20 | Titer Day 31 | Cells Day 53 | Titer Day 62 | Cells Day 86 | BTLA-Ig iv Day 87 | Fusion Day 90 |
|---|---|---|---|---|---|---|---|---|---|
| 55911 | Ig-Ribi | Ig-Ribi | Ig-Ribi | 1350 | Cells | 12150 | Cells | Ig-PBS | Fusion-55911 |
| 55919 | | Cells | Ig-Ribi | 1350 | Cells | 4050 | Cells | Ig-PBS | Fusion-55919 |

*BTLA-Ig 25 ug/mouse in Ribi adjuvant
*Cells = $10^7$ CHO-BTLA cells per mouse

Transgenic KM Mice™ were immunized over a period of 90 days with a combination of BTLA Ig antigen and BTLA expressed on CHO cells as outlined in Table 2. BTLA-Ig was administered in Ribi adjuvant as a Sc+Ip immunization, or as an intervenous injection in PBS before fusion. Cells ($1\times10^7$/mouse) were administered Ip in PBS. The immunization schedule is shown in Table 2. The immune response was monitored by retroorbital bleeds. The plasma was screened by ELISA (as described below), and mice with sufficient titers of anti-BTLA human immunogolobulin were used for fusions. Mice were boosted intravenously with antigen 3 days before sacrifice and removal of the spleen. Ten HuMab and ten KM Mice™ were immunized.

Selection of HuMab or KM Mice™ Producing Anti-BTLA Antibodies:

To select HuMab or KM Mice™ producing antibodies that bound BTLA, sera from immunized mice were tested by ELISA as described by Fishwild, D. et al. (1996). Briefly, microtiter plates were coated with purified recombinant BTLA fusion protein from transfected CHO cells at 1 µg/ml in PBS, 100 µl/wells incubated 4° C. overnight then blocked with 200 µl/well of 1% BSA in PBS/Tween (0.05%). Dilutions of sera from BTLA-immunized mice were added to each well and incubated for 1-2 hours at ambient temperature. The plates were washed with PBS/Tween and then incubated with a goat-anti-human IgG polyclonal antibody conjugated with alkaline phosphatase (AP) for 1 hour at room temperature. After washing, the plates were developed with pNPP substrate (Sigma N 2770) and analyzed by spectrophotometer at OD 405. Mice that developed the highest titers of anti-BTLA antibodies were used for fusions. Fusions were performed as described below and hybridoma supernatants were tested for anti-BTLA activity by ELISA and FACS.

Generation of Hybridomas Producing Human Monoclonal Antibodies to BTLA:

The mouse splenocytes, isolated from the KM Mice™, were fused with PEG to a mouse myeloma cell line based upon standard protocols. The resulting hybridomas were then screened for the production of antigen-specific antibodies. Single cell suspensions of splenocytes from immunized mice were fused to an equal number of the P3x63-Ag8.653 non-secreting mouse myeloma cells (ATCC, CRL 1580) with 50% PEG (Sigma) or by electrofusion (E-fusion, Cyto Pulse™ technology). Cells are plated at approximately $2\times10^5$ in flat bottom microtiter plates, followed by a two week incubation in selective medium containing 10% FBS, 3-5% Origen (IGEN), OPI supplement (Sigma O 5003: $1.1\times10^{-3}$ M Oxalo acetic acid, $4.5\times10^{-4}$ M sodium Pyruvate, and 24 international units/L Bovine Insulin), 4 mM L-glutamine, 0.055 mM 2-mercaptoethanol, 50 units/ml penicillin, 50 mg/ml streptomycin, and 1×HAT. After approximately two weeks, cells can be cultured in medium in which the HAT is replaced with HT. Individual wells were then screened by ELISA and FACS (described above) for human anti-BTLA monoclonal IgG antibodies. The antibody-secreting hybridomas were replated, screened again and, if still positive for human IgG, anti-BTLA monoclonal antibodies were subcloned at least twice by limiting dilution. The stable subclones were then cultured in vitro to generate small amounts of antibody in tissue culture medium for further characterization.

Hybridoma clones 1B4, E4H9, 3C2, 6A5, 11E2, E8D9, 10H6 and 4C9 were selected for further analysis.

Example 2

Structural Characterization of Human Monoclonal Antibodies 1B4, E4H9, 3C2, 3C2a, 6A5, 11E2, E8D9, 10H6 and 4C9

The cDNA sequences encoding the heavy and light chain variable regions of the 1B4, E4H9, 3C2, 3C2a, 6A5, 11E2, E8D9, 10H6 and 4C9 monoclonal antibodies were obtained from the 1B4, E4H9, 3C2, 3C2a, 6A5, 11E2, E8D9, 10H6 and 4C9 hybridomas, respectively, using standard PCR techniques and were sequenced using standard DNA sequencing techniques.

The nucleotide and amino acid sequences of the heavy chain variable region of 1B4 are shown in FIG. 1A and in SEQ ID NO: 53 and 1, respectively.

The nucleotide and amino acid sequences of the light chain variable region of 1B4 are shown in FIG. 1B and in SEQ ID NO: 59 and 7, respectively.

Comparison of the 1B4 heavy chain immunoglobulin sequence to the known human germline immunoglobulin heavy chain sequences demonstrated that the 1B4 heavy chain utilizes a VH segment from human germline VH 2-05, a D segment from human germline 3-10, and a JH segment from human germline JH 6b. The alignment of the 1B4 VH sequence to the germline VH 2-05 sequence is shown in FIG. 7. Further analysis of the 1B4 VH sequence using the Kabat system of CDR region determination led to the delineation of the heavy chain CDR1, CDR2 and CD3 regions as shown in FIGS. 1A and 7, and in SEQ ID NOs: 14, 20 and 26, respectively.

Comparison of the 1B4 light chain immunoglobulin sequence to the known human germline immunoglobulin light chain sequences demonstrated that the 1B4 light chain utilizes a VL segment from human germline VK A27 and a JK segment from human germline JK 5. The alignment of the 1B4 VL sequence to the germline VK A27 sequence is shown in FIG. 8. Further analysis of the 1B4 VL sequence using the Kabat system of CDR region determination led to the delineation of the light chain CDR1, CDR2 and CD3 regions as shown in FIGS. 1B and 8, and in SEQ ID NOs: 32, 39 and 46, respectively.

The nucleotide and amino acid sequences of the heavy chain variable region of E4H9 are shown in FIG. 2A and in SEQ ID NO: 54 and 2, respectively.

The nucleotide and amino acid sequences of the light chain variable region of E4H9 are shown in FIG. 2B and in SEQ ID NO: 60 and 8, respectively.

Comparison of the E4H9 heavy chain immunoglobulin sequence to the known human germline immunoglobulin heavy chain sequences demonstrated that the E4H9 heavy chain utilizes a VH segment from human germline VH 2-70, a D segment from human germline 3-10, and a JH segment from human germline JH 6b. The alignment of the E4H9 VH sequence to the germline VH 2-70 sequence is shown in FIG. 9. Further analysis of the E4H9 VH sequence using the Kabat system of CDR region determination led to the delineation of the heavy chain CDR1, CDR2 and CD3 regions as shown in FIGS. 2A and 9, and in SEQ ID NOs: 15, 21 and 27, respectively.

Comparison of the E4H9 light chain immunoglobulin sequence to the known human germline immunoglobulin light chain sequences demonstrated that the E4H9 light chain utilizes a VL segment from human germline VK A27 and a JK segment from human germline JK 3. The alignment of the E4H9 VL sequence to the germline VK A27 sequence is shown in FIG. 10. Further analysis of the E4H9 VL sequence using the Kabat system of CDR region determination led to the delineation of the light chain CDR1, CDR2 and CD3 regions as shown in FIGS. 2B and 33, and in SEQ ID NOs: 40, and 47, respectively.

The nucleotide and amino acid sequences of the heavy chain variable region of 3C2 are shown in FIG. 3A and in SEQ ID NO: 55 and 3, respectively.

The nucleotide and amino acid sequences of the light chain variable region of 3C2 are shown in FIG. 3B and in SEQ ID NO: 61 and 9, respectively.

Comparison of the 3C2 heavy chain immunoglobulin sequence to the known human germline immunoglobulin heavy chain sequences demonstrated that the 3C2 heavy chain utilizes a VH segment from human germline VH 4-59, a D segment from human germline 6-19, and a JH segment from human germline JH 4b. The alignment of the 3C2 VH sequence to the germline VH 4-59 sequence is shown in FIG. 11. Further analysis of the 3C2 VH sequence using the Kabat system of CDR region determination led to the delineation of the heavy chain CDR1, CDR2 and CD3 regions as shown in FIGS. 3A and 11, and in SEQ ID NOs: 16, 22 and 28, respectively.

Comparison of the 3C2 light chain immunoglobulin sequence to the known human germline immunoglobulin light chain sequences demonstrated that the 3C2 light chain utilizes a VL segment from human germline VK L18 and a JK segment from human germline JK 4. The alignment of the 3C2 VL sequence to the germline VK L18 sequence is shown in FIG. 12. Further analysis of the 3C2 VL sequence using the Kabat system of CDR region determination led to the delineation of the light chain CDR1, CDR2 and CD3 regions as shown in FIGS. 3B and 11, and in SEQ ID NOs: 34, 41 and 48, respectively.

The nucleotide and amino acid sequences of the light chain variable region of 3C2a are shown in FIG. 3C and in SEQ ID NO: 62 and 10, respectively.

Comparison of the 3C2a light chain immunoglobulin sequence to the known human germline immunoglobulin light chain sequences demonstrated that the 3C2a light chain utilizes a VL segment from human germline VK A27 and a JK segment from human germline JK 2. The alignment of the 3C2a VL sequence to the germline VK A27 sequence is shown in FIG. 13. Further analysis of the 3C2a VL sequence using the Kabat system of CDR region determination led to the delineation of the light chain CDR1, CDR2 and CD3 regions as shown in FIGS. 3C and 12, and in SEQ ID NOs: 35, 42 and 49, respectively.

The nucleotide and amino acid sequences of the heavy chain variable region of 6A5 are shown in FIG. 4A and in SEQ ID NO: 56 and 4, respectively.

The nucleotide and amino acid sequences of the light chain variable region of 6A5 are shown in FIG. 4B and in SEQ ID NO: 63 and 11, respectively.

Comparison of the 6A5 heavy chain immunoglobulin sequence to the known human germline immunoglobulin heavy chain sequences demonstrated that the 6A5 heavy chain utilizes a VH segment from human germline VH 2-05, a D segment from the human germline 3-10, and a JH segment from human germline JH 6b. The alignment of the 6A5 VH sequence to the germline VH 2-05 sequence is shown in FIG. 14. Further analysis of the 6A5 VH sequence using the Kabat system of CDR region determination led to the delineation of the heavy chain CDR1, CDR2 and CD3 regions as shown in FIGS. 4A and 14, and in SEQ ID NOs: 17, 23 and 29, respectively.

Comparison of the 6A5 light chain immunoglobulin sequence to the known human germline immunoglobulin light chain sequences demonstrated that the 6A5 light chain utilizes a VL segment from human germline VK A27 and a JK segment from human germline JK 5. The alignment of the 6A5 VL sequence to the germline VK A27 sequence is shown in FIG. 15. Further analysis of the 6A5 VL sequence using the Kabat system of CDR region determination led to the delineation of the light chain CDR1, CDR2 and CD3 regions as shown in FIGS. 4B and 36, and in SEQ ID NOs: 43, and 50, respectively.

The nucleotide and amino acid sequences of the heavy chain variable region of 11E2 are shown in FIG. 5A and in SEQ ID NO: 57 and 5, respectively.

The nucleotide and amino acid sequences of the light chain variable region of 11E2 are shown in FIG. 5B and in SEQ ID NO: 64 and 12, respectively.

Comparison of the 11E2 heavy chain immunoglobulin sequence to the known human germline immunoglobulin heavy chain sequences demonstrated that the 11E2 heavy chain utilizes a VH segment from human germline VH 3-20, a D segment from human germline 3-10, and a JH segment from human germline JH 6b. The alignment of the 11E2 VH sequence to the germline VH 3-20 sequence is shown in FIG. 16. Further analysis of the 11E2 VH sequence using the Kabat system of CDR region determination led to the delineation of the heavy chain CDR1, CDR2 and CD3 regions as shown in FIGS. 5A and 16, and in SEQ ID NOs: 18, 24 and 30, respectively.

Comparison of the 11E2 light chain immunoglobulin sequence to the known human germline immunoglobulin light chain sequences demonstrated that the 11E2 light chain utilizes a VL segment from human germline VK L15 and a JK segment from human germline JK 1. The alignment of the 11 E2 VL sequence to the germline VK L15 sequence is shown in FIG. 17. Further analysis of the 11E2 VL sequence using the Kabat system of CDR region determination led to the delineation of the light chain CDR1, CDR2 and CD3 regions as shown in FIGS. 5B and 17, and in SEQ ID NOs: 37, 44 and 51, respectively.

The nucleotide and amino acid sequences of the heavy chain variable region of E8D9 are shown in FIG. 6A and in SEQ ID NO: 57 and 5, respectively.

The nucleotide and amino acid sequences of the light chain variable region of E8D9 are shown in FIG. 6B and in SEQ ID NO: 65 and 13, respectively.

Comparison of the E8D9 heavy chain immunoglobulin sequence to the known human germline immunoglobulin heavy chain sequences demonstrated that the E8D9 heavy chain utilizes a VH segment from human germline VH 2-05, a D segment from human germline 3-10, and a JH segment from human germline JH 6b. The alignment of the E8D9 V11 sequence to the germline VH 2-05 sequence is shown in FIG. 18. Further analysis of the E8D9 VH sequence using the Kabat system of CDR region determination led to the delineation of the heavy chain CDR1, CDR2 and CD3 regions as shown in FIGS. 6A and 18, and in SEQ ID NOs: 19, 25 and 31, respectively.

Comparison of the E8D9 light chain immunoglobulin sequence to the known human germline immunoglobulin light chain sequences demonstrated that the E8D9 light chain utilizes a VL segment from human germline VK A27 and a JK segment from human germline JK 4. The alignment of the E8D9 VL sequence to the germline VK A27 sequence is shown in FIG. 19. Further analysis of the E8D9 VL sequence using the Kabat system of CDR region determination led to the delineation of the light chain CDR1, CDR2 and CD3 regions as shown in FIGS. 6B and 19, and in SEQ ID NOs: 38, 45 and 52, respectively.

The nucleotide and amino acid sequences of the heavy chain variable region of 10H6 are shown in FIG. 21A and in SEQ ID NO: 83 and 74, respectively.

The nucleotide and amino acid sequences of the light chain variable region of 10H6 are shown in FIG. 21B and in SEQ ID NO: 84 and 75, respectively.

Comparison of the 10H6 heavy chain immunoglobulin sequence to the known human germline immunoglobulin heavy chain sequences demonstrated that the 10H6 heavy chain utilizes a V11 segment from human germline V113-33, a D segment from human germline 3-10, and a JH segment from human germline JH 6b. The alignment of the 10H6 VH sequence to the germline VH 4-59 sequence is shown in FIG. 22. Further analysis of the 10H6 VH sequence using the Kabat system of CDR region determination led to the delineation of the heavy chain CDR1, CDR2 and CD3 regions as shown in FIGS. 21A and 22, and in SEQ ID NOs: 77, 78 and 79, respectively.

Comparison of the 10H6 light chain immunoglobulin sequence to the known human germline immunoglobulin light chain sequences demonstrated that the 10H6 light chain utilizes a VL segment from human germline VK 04, which is classified as a pseudogene. However, in this situation, it is actually being expressed. The 10H6 light chain also utilizes a JK segment from human germline JK 2. The alignment of the 10H6 VL sequence to the germline VK 04 sequence is shown in FIG. 23. Further analysis of the 10H6 VL sequence using the Kabat system of CDR region determination led to the delineation of the light chain CDR1, CDR2 and CD3 regions as shown in FIGS. 21B and 23, and in SEQ ID NOs: 80, 81 and 82, respectively.

The nucleotide and amino acid sequences of the light chain variable region of 10H6a are shown in FIG. 21C and in SEQ ID NO: 98 and 76, respectively.

Comparison of the 10H6a light chain immunoglobulin sequence to the known human germline immunoglobulin light chain sequences demonstrated that the 10H6a light chain utilizes a VL segment from human germline VK A27 and a JK segment from human germline JK 5. The alignment of the 10H6a VL sequence to the germline VK A27 sequence is shown in FIG. 24. Further analysis of the 10H6a VL sequence using the Kabat system of CDR region determination led to the delineation of the light chain CDR1, CDR2 and CD3 regions as shown in FIGS. 21C and 24, and in SEQ ID NOs: 95, 96 and 97, respectively.

The nucleotide and amino acid sequences of the heavy chain variable region of 4C9 are shown in FIG. 25A and in SEQ ID NO: 93 and 85, respectively.

The nucleotide and amino acid sequences of the light chain variable region of 4C9 are shown in FIG. 25B and in SEQ ID NO: 94 and 86, respectively.

Comparison of the 4C9 heavy chain immunoglobulin sequence to the known human germline immunoglobulin heavy chain sequences demonstrated that the 4C9 heavy chain utilizes a VH segment from human germline VH 2-05, a D segment from human germline 3-10, and a JH segment from human germline JH 6b. The alignment of the 4C9 VH sequence to the germline VH 2-05 sequence is shown in FIG. 26. Further analysis of the 4C9 VH sequence using the Kabat system of CDR region determination led to the delineation of the heavy chain CDR1, CDR2 and CD3 regions as shown in FIGS. 25A and 26, and in SEQ ID NOs: 87, 88, and 89, respectively.

Comparison of the 4C9 light chain immunoglobulin sequence to the known human germline immunoglobulin light chain sequences demonstrated that the 4C9 light chain utilizes a VL segment from human germline VK A27, a JK segment from human germline JK 1. The alignment of the 4C9 VL sequence to the germline VK A27 sequence is shown in FIG. 27. Further analysis of the 4C9 VL sequence using the Kabat system of CDR region determination led to the delineation of the light chain CDR1, CDR2 and CD3 regions as shown in FIGS. 25B and 27, and in SEQ ID NOs: 90, 91, and 92, respectively.

Example 3

Characterization of Binding of Anti-BTLA Human Monoclonal Antibodies

In this example, binding affinity and binding kinetics of anti-BTLA antibodies were examined by Biacore analysis. Binding kinetics and inhibition were examined by flow cytometry.

Binding Affinity and Kinetics

Anti-BTLA antibodies were characterized for affinities and binding kinetics by Biacore analysis (Biacore AB, Uppsala, Sweden). Purified recombinant human BTLA fusion protein was covalently linked to a CM5 chip (carboxy methyl dextran coated chip) via primary amines, using standard amine coupling chemistry and kit provided by Biacore. Binding was measured by flowing the antibodies in HBS EP buffer (provided by Biacore AB) at a concentration of 267 nM at a flow rate of 50 μl/min. The antigen-antibody association kinetics was followed for 3 minutes and the dissociation kinetics was followed for 7 minutes. The association and dissociation curves were fit to a 1:1 Langmuir binding model using BIAevaluation software (Biacore AB). To minimize the effects of avidity in the estimation of the binding constants, only the initial segment of data corresponding to association and dissociation phases were used for fitting. The $K_D$ values that were determined are shown in Table 3.

TABLE 3

KD, Mass of H and L chains, BiaCore

| Clone | Isotype | KD × 10–9 M | Heavy Chain Mass (D) | Light Chain Mass (D) |
|---|---|---|---|---|
| 6A5 | IgG4 | | 23793.4 | 50541.3 |
| E4H9 | IgG4 | 0.13 | 23692.3 | 50916.9 |
| E8D9 | IgG4 | | 23525.0 | |
| 1B4 | IgG1 | 2.88 | 23585.0 | |
| 3C2 | IgG1 | 0.88 | | |
| 11E2 | IgG1 | 0.61 | 23697.0 | 50405.6 |

Binding Specificity by Flow Cytometry

Chinese hamster ovary (CHO) cell lines that express recombinant human BTLA at the cell surface were developed and used to determine the specificity of BTLA human monoclonal antibodies by flow cytometry. CHO cells were transfected with expression plasmids containing full length cDNA encoding transmembrane forms of BTLA. Binding of the anti-BTLA human monoclonal antibodies was assessed by incubating the transfected cells with the anti-BTLA human monoclonal antibodies at a concentration from 0.01 nM to 66 nM. The antibodies were incubated with $10^5$ BTLA CHO cells for 60 minutes at 4° C. in PBS1% BSA. Cells were washed 2× in PBS-1% BSA and stained with PE labeled anti-Human IgG (Jackson InmmuoResearch 109-115-098). The $EC_{50}$ was determined graphically by plotting the mean flourescence intensity (MFI) versus the log of the antibody concentration using Prism graphing software (GraphPad software). Flow cytometric analyses were performed using a FACSArray flow cytometry (Becton Dickinson, San Jose, Calif.). The results are depicted in FIG. 28A.

Example 4

Anti-BTLA Antibodies Inhibit HVEM Ligand Binding to Cells Expressing BTLA

Figure 28B:
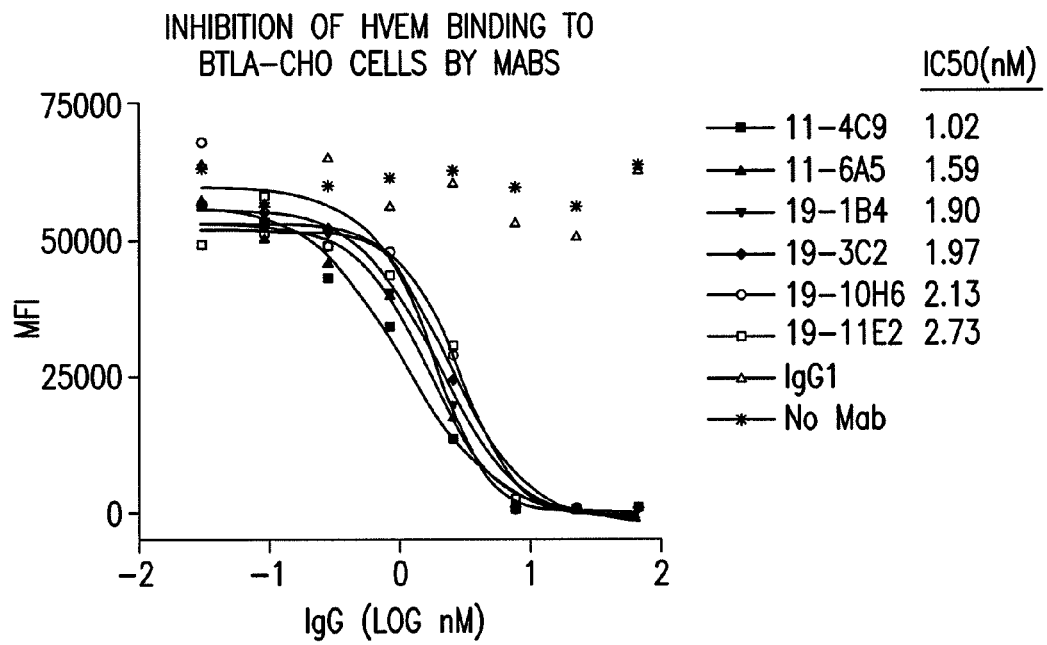
FIG. 28B and FIG. 28C demonstrate anti-BTLA antibodies prevent HVEM binding to BTLA-CHO cells in a concentration dependent manner.
Figure 28C:
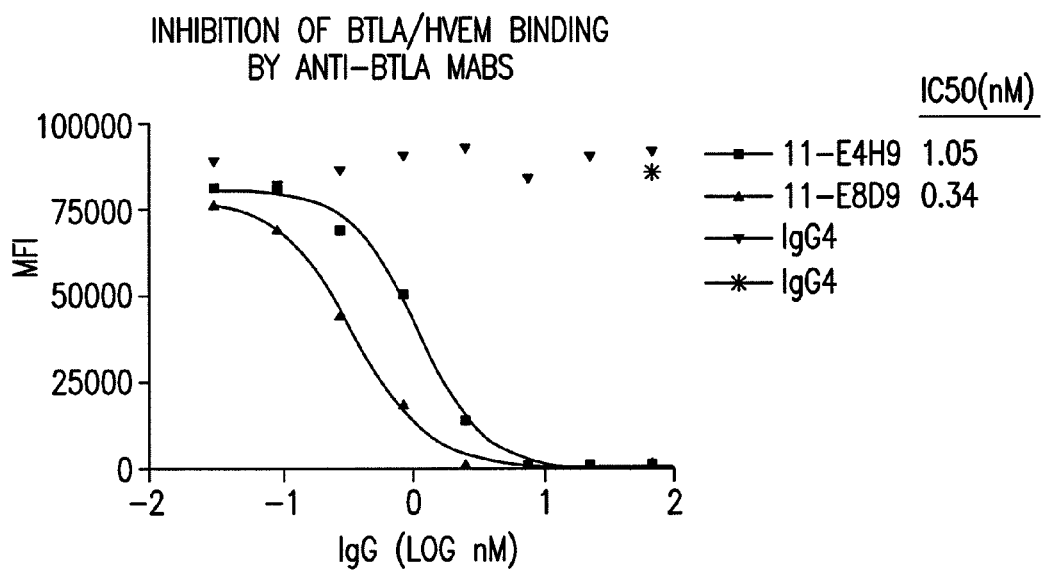

The ability of BTLA Mabs to block binding of BTLA to HVEM was also determined by FACS, and is expressed as the concentration of anti-BTLA IgG to block half the maximal binding of HVEM Ig to $10^5$ BTLA CHO cells ($IC_{50}$). BTLA CHO cells and antibody at various concentrations were pre-incubated for 30 minutes at 4° C., and then 0.5 ug/ml biotin labeled HVEM Ig (R & D Systems BAF 356) was added to the BTLA CHO-IgG mix and incubated for another 30 minutes. Cells were washed 2× in PBS-1% BSA, and binding of biotin HVEM Ig was detected by FACS after staining the cells with streptavidin-PE (BD Parmingen 3554061). $IC_{50}$ values were determined graphically using the Prism software (GraphPad Software). Results are depicted in FIG. 28B and FIG. 28C.

Example 5

Determination of Anti-BTLA Antibody Specificity

An ELISA assay was developed to verify the specificity of a panel of anti-BTLA antibodies for the BTLA receptor and to show that there is no substantial cross-reactivity with other members of the CD28 family of receptors.

ELISA plates were coated overnight with fusion proteins consisting of the extracellular domains of a panel of CD28 receptor family molecules fused to the Fc portion of human IgG (Table 4). The plates were washed and blocked to minimize non-specific binding. A panel of anti-BTLA antibodies and isotype control antibodies (Table 5), and positive control detection antibodies (Table 3), all diluted to 1 ug/mL, were added in duplicate to the assay plates for one hour. After extensive washing the appropriate HRP-conjugated detection antibodies were added to the plates for one hour followed by washing and development using 3, 3', 5, 5'-tetramethylbenzidine (TMB) as substrate. Optical density measurements at 650 nm were recorded.

TABLE 4

| Plate Coating Reagents | | | Control Detection Reagents | | |
|---|---|---|---|---|---|
| Protein | Source | Cat. No. | Protein | Source | Cat. No. |
| TrkB-lg | R&D Systems | 688-TK | mu-anti-HuTrkB | R&D Systems | MAB397 |
| PD-1-lg | R&D Systems | 1086-PD | mu-αtHuPD1 clone MIH4 | eBioscience | 14-9969-82 |
| CTLA4-lg | R&D Systems | 325-CT | anti-CTLA4 | Medarex | n/a |
| ICOS-lg | R&D Systems | 169-CS | goat-anti-HuICOS | R&D Systems | AF169 |
| CD28-lg | R&D Systems | 342-CD | anti-hCD28, clone CD28.2 | eBioscience | 16-0289-85 |
| h5BTLA-lg | Medarex | n/a | | | |

TABLE 5

| Anti-BTLA Clone or Isotype Control | Source | Cat No. |
|---|---|---|
| 11 E4H9.3 | Medarex | n/a |
| 19 1B4.1 | Medarex | n/a |
| 19 3C2.16 | Medarex | n/a |
| 11 6A5.10 | Medarex | n/a |
| 19 11E2.9 | Medarex | n/a |
| 11 E8D9.3 | Medarex | n/a |
| huIgG1 Isotype | Medarex | n/a |
| huIgG4 Isotype | Medarex | n/a |

Figure 29A:
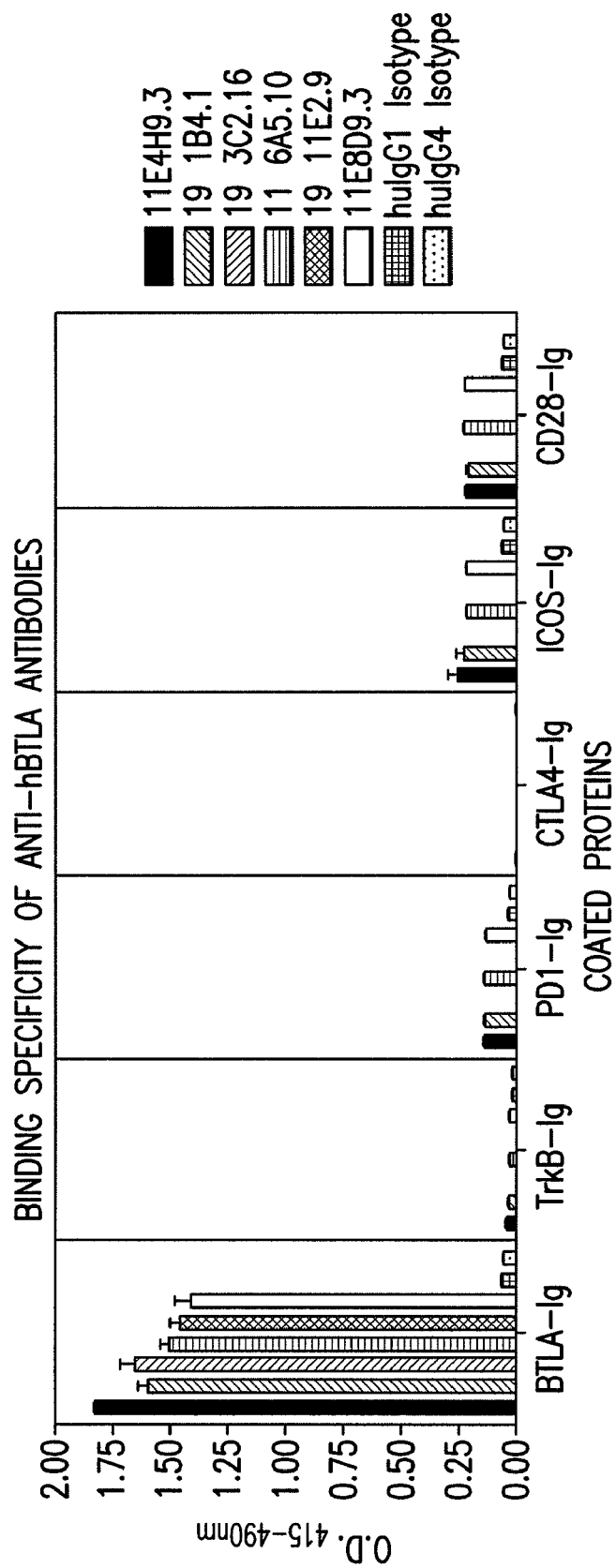
FIG. 29 demonstrates antigen specificity of anti-BTLA antibodies. A. Depicts binding specificity of various anti-BTLA antibodies compared to their binding to other CD28 molecules. B. Depicts antigen specific control.
Figure 29B:
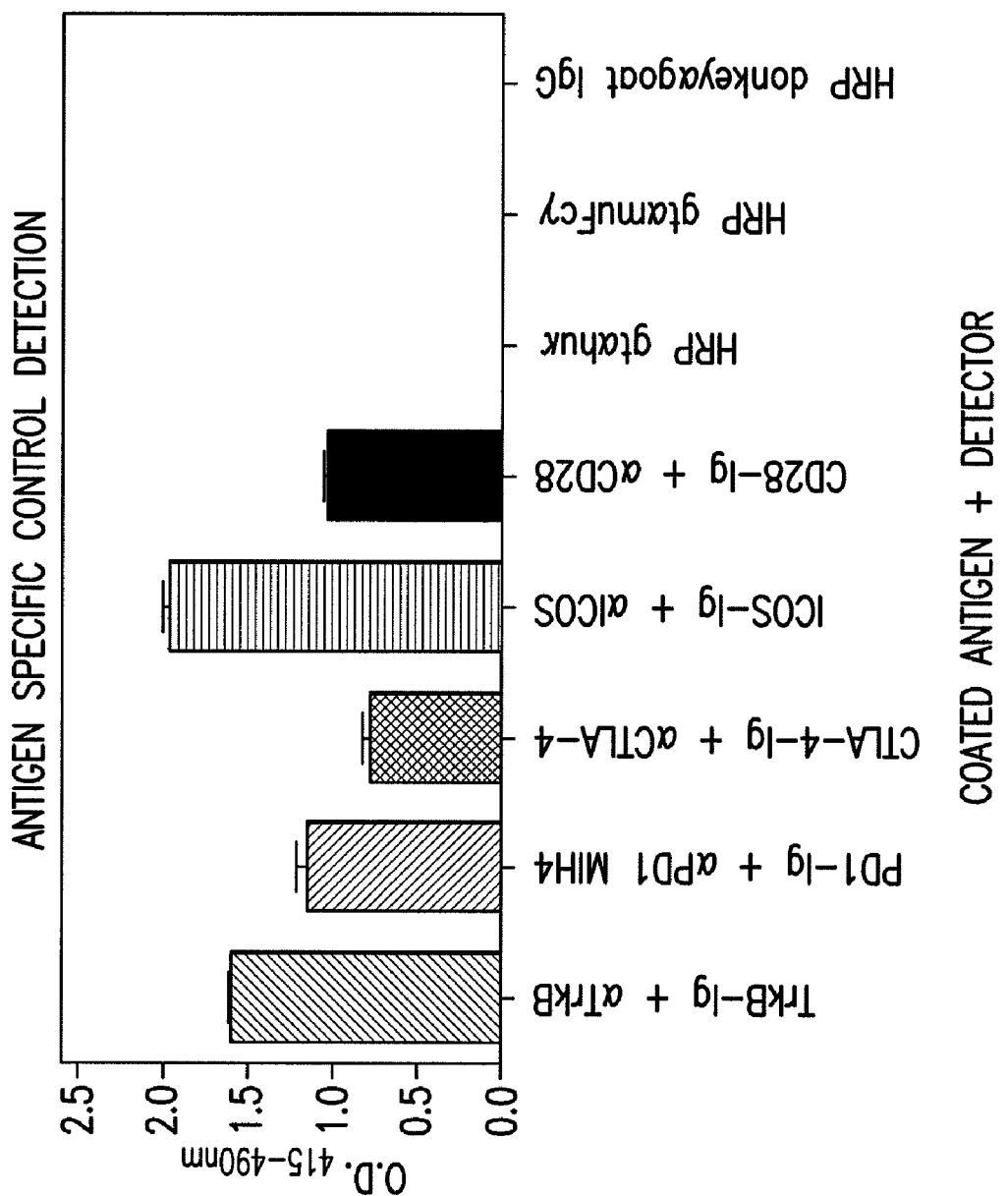

In comparison to the BTLA-specific reactivity that was observed (FIGS. 29A & 29B), there was no substantial cross-reaction with any of the other CD28 family member receptors tested. These results indicate that the panel of anti-BTLA antibodies tested here specifically bind to human BTLA.

Example 6

Treatment of In Vivo Tumor Model Using Anti-BTLA Antibodies

Mice implanted with a cancerous tumor are treated in vivo with anti-BTLA antibodies to examine the in vivo effect of the antibodies on tumor growth. As a positive control, an anti-CTLA-4 antibody is used, since such antibodies have been shown to inhibit tumor growth in vivo.

For the tumor studies, female AJ mice between 6-8 weeks of age (Harlan Laboratories) are randomized by weight into 6 groups. The mice are implanted subcutaneously in the right flank with $2\times10^6$ SA1/N fibrosarcoma cells dissolved in 200 µl of DMEM media on day 0. The mice are treated with PBS vehicle, or antibodies at 10 mg/kg. The animals are dosed by intraperitoneal injection with approximately 200 µl of PBS containing antibody or vehicle on days 1, 4, 8 and 11. Each group contains 10 animals and the groups consist of: (i) a vehicle group, (ii) control mouse IgG, (iii) control hamster IgG, (iv) hamster anti-mouse BTLA antibody and (v) the fully human anti-BTLA. The mice are monitored twice weekly for tumor growth for approximately 6 weeks. Using an electronic caliper, the tumors are measured three dimensionally (height×width×length) and tumor volume is calculated. Mice are euthanized when the tumors reach tumor end point (1500 mm$^3$) or show greater than 15% weight loss.

Example 7

Additional Binding Characterization of Antibodies

The binding of the 1B4, E4H9, 3C2, 6A5, 11E2 and 10116 antibodies to recombinant BTLA protein was examined by BIAcore™ using an antibody capture method. Each of the six anti-BTLA monoclonal antibodies were captured using anti-CH1, a reagent antibody that is specific towards the heavy chain constant region 1 of human antibody (Zymed, Clone HP6045, Stock conc. 1.0 mg/mL). Anti-CH1 was coated on a CM5 chip (BR-1000-14, Research Grade) at high density (6200-7960 RUs). The coating was carried out based on the standard immobilization procedure recommended by the manufacturer. The 1B4, E4H9, 3C2, 6A5, 11E2 and 10116 purified antibodies, with concentrations ranging from 1-10 µg/mL, were each then captured on the anti-CH1 coated chip surface at a flow-rate of 10 µl/min for 0.5-1 minute. A single concentration of recombinant human BTLA fusion protein (200 nM) was injected over captured antibody for 4 minutes at a flow rate of 300 min. The antigen was allowed to dissociate for 10 minutes. The chip surface was regenerated after each cycle with 10 µL of 30 mM NaOH, followed by 30 µl of HBS EP wash. Isotype controls were run on the chip, and the data used to subtract non-specific binding. All the experiments were carried out on a Biacore 3000 surface plasmon resonance instrument, using BIAcore Control software v 3.2. Data analysis was carried out using BiaEvaluation v3.2 software. The results are shown in Table 6 below.

TABLE 6

Binding Affinity and Kinetics of Anti-BTLA Antibodies to Human BTLA

| Antibody | $K_D \times 10^{-9}$ (M) | $k_{on} \times 10^4$ (1/Ms) | $k_{off} \times 10^{-4}$ (1/s) |
|---|---|---|---|
| 1B4 | 5.74 | 4.94 | 2.84 |
| E4H9 | 0.006 | 4.57 | 0.003 |
| 3C2 | 6.65 | 4.52 | 3.01 |
| 6A5 | 0.09 | 3.89 | 0.04 |
| 11E2 | 8.54 | 2.8 | 9.84 |
| 10H6 | 3.82 | 4.0 | 1.53 |

The BIAcore results for 1B4, E4H9, 3C2, 6A5, 11E2 and 10H6 confirm the flow cytometry and earlier BIAcore results (described in Example 3, above) that the antibodies are capable of binding with high affinity to human BTLA. It is noted that the $K_D$ values obtained using the antibody capture method described in this example differ somewhat from the $K_D$ values described in Example 3, in which the antigen capture method was used. This may be due to the fact that the antibody capture method used in this example does not have an antibody avidity component to it. Additionally or alternatively, the differences in affinities between the two methods may be indicative of differences in the molecular recognition process by the mAbs for antigen captured on the surface of the chip versus antigen in solution.

---

We claim:

1. An isolated monoclonal antibody or antigen binding portion thereof, comprising a heavy chain variable region that comprises CDR1, CDR2, and CDR3 domains; and a light chain variable region that comprises CDR1, CDR2, and CDR3 domains, wherein:
   (a) the heavy chain variable region CDR3 comprises amino acids having the sequence set forth in SEQ ID NO: 26; and the light chain variable region CDR3 comprises amino acids having the sequence set forth in SEQ ID NO: 46 and conservative modifications thereof;
   (b) the heavy chain variable region CDR3 comprises amino acids having the sequence set forth in SEQ ID NO: 27; and the light chain variable region CDR3 comprises amino acids having the sequence set forth in SEQ ID NO: 47 and conservative modifications thereof;
   (c) the heavy chain variable region CDR3 comprises amino acids having the sequence set forth in SEQ ID NO: 28; and the light chain variable region CDR3 comprises amino acids having the sequence set forth in SEQ ID NO: 48 and conservative modifications thereof;
   (d) the heavy chain variable region CDR3 comprises amino acids having the sequence set forth in SEQ ID NO: 28; and the light chain variable region CDR3 comprises amino acids having the sequence set forth in SEQ ID NO: 49 and conservative modifications thereof;

(e) the heavy chain variable region CDR3 comprises amino acids having the sequence set forth in SEQ ID NO: 29; and the light chain variable region CDR3 comprises amino acids having the sequence set forth in SEQ ID NO: 50 and conservative modifications thereof;
(f) the heavy chain variable region CDR3 comprises amino acids having the sequence set forth in SEQ ID NO: 30; and the light chain variable region CDR3 comprises amino acids having the sequence set forth in SEQ ID NO: 51 and conservative modifications thereof;
(g) the heavy chain variable region CDR3 comprises amino acids having the sequence set forth in SEQ ID NO: 31; and the light chain variable region CDR3 comprises amino acids having the sequence set forth in SEQ ID NO: 52 and conservative modifications thereof;
(h) the heavy chain variable region CDR3 comprises amino acids having the sequence set forth in SEQ ID NO: 79; and the light chain variable region CDR3 comprises amino acids having the sequence set forth in SEQ ID NO: 82 and conservative modifications thereof;
(i) the heavy chain variable region CDR3 comprises amino acids having the sequence set forth in SEQ ID NO: 79; and the light chain variable region CDR3 comprises amino acids having the sequence set forth in SEQ ID NO: 97 and conservative modifications thereof; or
(j) the heavy chain variable region CDR3 comprises amino acids having the sequence set forth in SEQ ID NO: 89; and the light chain variable region CDR3 comprises amino acids having the sequence set forth in SEQ ID NO: 92 and conservative modifications thereof; and wherein antibody or antigen-binding portion thereof specifically binds to human BTLA.

2. An isolated monoclonal antibody or antigen binding portion thereof, wherein antibody or antigen-binding portion thereof cross-competes for binding to BTLA with a reference antibody or reference antigen-binding portion thereof comprising a heavy chain variable region that comprises CDR1, CDR2, and CDR3 domains; and a light chain variable region that comprises CDR1, CDR2, and CDR3 domains, wherein:
(a) the heavy chain variable region CDR3 of the reference antibody or reference antigen-binding portion thereof comprises amino acids having the sequence set forth in SEQ ID NO: 26; and the light chain variable region CDR3 of the reference antibody or reference antigen-binding portion thereof comprises amino acids having the sequence set forth in SEQ ID NO: 46;
(b) the heavy chain variable region CDR3 of the reference antibody or reference antigen-binding portion thereof comprises amino acids having the sequence set forth in SEQ ID NO: 27; and the light chain variable region CDR3 of the reference antibody or reference antigen-binding portion thereof comprises amino acids having the sequence set forth in SEQ ID NO: 47;
(c) the heavy chain variable region CDR3 of the reference antibody or reference antigen-binding portion thereof comprises amino acids having the sequence set forth in SEQ ID NO: 28; and the light chain variable region CDR3 of the reference antibody or reference antigen-binding portion thereof comprises amino acids having the sequence set forth in SEQ ID NO: 48;
(d) the heavy chain variable region CDR3 of the reference antibody or reference antigen-binding portion thereof comprises amino acids having the sequence set forth in SEQ ID NO: 28; and the light chain variable region CDR3 of the reference antibody or reference antigen-binding portion thereof comprises amino acids having the sequence set forth in SEQ ID NO: 49;
(e) the heavy chain variable region CDR3 of the reference antibody or reference antigen-binding portion thereof comprises amino acids having the sequence set forth in SEQ ID NO: 29; and the light chain variable region CDR3 of the reference antibody or reference antigen-binding portion thereof comprises amino acids having the sequence set forth in SEQ ID NO: 50;
(f) the heavy chain variable region CDR3 of the reference antibody or reference antigen-binding portion thereof comprises amino acids having the sequence set forth in SEQ ID NO: 30; and the light chain variable region CDR3 of the reference antibody or reference antigen-binding portion thereof comprises amino acids having the sequence set forth in SEQ ID NO: 51;
(g) the heavy chain variable region CDR3 of the reference antibody or reference antigen-binding portion thereof comprises amino acids having the sequence set forth in SEQ ID NO: 31; and the light chain variable region CDR3 of the reference antibody or reference antigen-binding portion thereof comprises amino acids having the sequence set forth in SEQ ID NO: 52;
(h) the heavy chain variable region CDR3 of the reference antibody or reference antigen-binding portion thereof comprises amino acids having the sequence set forth in SEQ ID NO: 79; and the light chain variable region CDR3 of the reference antibody or reference antigen-binding portion thereof comprises amino acids having the sequence set forth in SEQ 7ID NO: 82;
(i) the heavy chain variable region CDR3 of the reference antibody or reference antigen-binding portion thereof comprises amino acids having the sequence set forth in SEQ ID NO: 79; and the light chain variable region CDR3 of the reference antibody or reference antigen-binding portion thereof comprises amino acids having the sequence set forth in SEQ ID NO: 97; or
(j) the heavy chain variable region CDR3 of the reference antibody or reference antigen-binding portion thereof comprises amino acids having the sequence set forth in SEQ ID NO: 89; and the light chain variable region CDR3 of the reference antibody or reference antigen-binding portion thereof comprises amino acids having the sequence set forth in SEQ ID NO: 92.

3. The antibody or antigen binding portion thereof, of claim 2, wherein the reference antibody or reference antigen binding portion thereof contains heavy chain variable region and light chain variable region CDR3 and CDR2 domains selected from the group consisting, of:
(a) a heavy chain variable region CDR3 comprising amino acids having the sequence set forth in SEO ID NO:26; a light chain variable region CDR3 comprising amino acids having the sequence set forth in SEQ ID NO:46; a heavy chain variable region CDR2 comprising amino acids having the sequence set forth in SEQ ID NO: 20; and a light chain variable region CDR2 comprising amino acids having the sequence set forth in SEQ ID NO: 39;
(b) a heavy chain variable region CDR3 comprising amino acids having the sequence set forth in SEQ ID NO:27; a light chain variable region CDR3 comprising amino acids having the sequence set forth in SEQ ID N0:47; a heavy chain variable region CDR2 comprising amino acids having the sequence set forth in SEQ ID NO: 21; and a light chain variable region CDR2 comprising amino acids having the sequence set forth in SEQ ID NO: 40;
(c) a heavy chain variable region CDR3 comprising amino acids having the sequence set forth in SEQ ID NO:28; a light chain variable region CDR3 comprising amino acids having the sequence set forth in SEQ ID NO:48; a heavy chain variable region CDR2 comprising amino acids having the sequence set forth in SEQ ID NO: 22; and a light chain variable region CDR2 comprising amino acids having the sequence set forth in SEQ ID NO: 41;

(d) a heavy chain variable region CDR3 comprising amino acids having the sequence set forth in SEQ ID NO:28; a light chain variable region CDR3 comprising amino acids having the sequence set forth in SEQ ID NO:49; a heavy chain variable region CDR2 comprising amino acids having the sequence set forth in SEQ ID NO: 22; and a light chain variable region CDR2 comprising amino acids having the sequence set forth in SEQ ID NO: 42;

(e) a heavy chain variable region CDR3 comprising amino acids having the sequence set forth in SEQ ID NO:29; a light chain variable region CDR3 comprising amino acids having the sequence set forth in SEQ ID NO:50; a heavy chain variable region CDR2 comprising amino acids having the sequence set forth in SEQ ID NO: 23; and a light chain variable region CDR2 comprising amino acids having the sequence set forth in SEQ ID NO: 43;

(f) a heavy chain variable region CDR3 comprising amino acids having the sequence set forth in SEQ ID NO:30; a light chain variable region CDR3 comprising amino acids having the sequence set forth in SEQ ID NO:51; a heavy chain variable region CDR2 comprising amino acids having the sequence set forth in SEQ ID NO: 24; and a light chain variable region CDR2 comprising amino acids having the sequence set forth in SEQ ID NO: 44;

(g) a heavy chain variable region CDR3 comprising amino acids having the sequence set forth in SEQ ID NO:31; a light chain variable region CDR3 comprising amino acids having the sequence set forth in SEQ ID NO:52; a heavy chain variable region CDR2 comprising amino acids having the sequence set forth in SEQ ID NO: 25; and a light chain variable region CDR2 comprising amino acids having the sequence set forth in SEQ ID NO: 45;

(h) a heavy chain variable region CDR3 comprising amino acids having the sequence set forth in SEQ ID NO:79; a light chain variable region CDR3 comprising amino acids having the sequence set forth in SEQ ID NO:82; a heavy chain variable region CDR2 comprising amino acids having the sequence set forth in SEQ ID NO: 78; and a light chain variable region CDR2 comprising amino acids having the sequence set forth in SEQ ID NO: 81;

(i) a heavy chain variable region CDR3 comprising amino acids having the sequence set forth in SEQ ID NO:79; a light chain variable region CDR3 comprising amino acids having the sequence set forth in SEQ ID NO:97; a heavy chain variable region CDR2 comprising amino acids having the sequence set forth in SEQ ID NO: 78; and a light chain variable region CDR2 comprising amino acids having the sequence set forth in SEQ ID NO: 96; or (j) a heavy chain variable region CDR3 comprising amino acids having the sequence set forth in SEQ ID NO:89; a light chain variable region CDR3 comprising amino acids having the sequence set forth in SEQ ID NO:92; a heavy chain variable region CDR2 comprising amino acids having the sequence set forth in SEQ ID NO: 88; and a light chain variable region CDR2 comprising amino acids having the sequence set forth in SEQ ID NO: 91.

4. The antibody or antigen binding portion thereof, of claim 3, wherein the reference antibody or reference antigen binding portion thereof contains heavy chain variable region and light chain variable region CDR3, CDR2, and CDR1 domains selected from the group consisting of:

(a) a heavy chain variable region CDR3 comprising amino acids having the sequence set forth in SEQ ID NO:26; a light chain variable region CDR3 comprising amino acids having the sequence set forth in SEQ ID NO:46; a heavy chain variable region CDR2 comprising amino acids having the sequence set forth in SEQ ID NO: 20; a light chain variable region CDR2 comprising amino acids having the sequence set forth in SEQ ID NO: 39; a heavy chain variable region CDR1 comprising amino acids having the sequence set forth in SEQ ID NO: 14; and a light chain variable region CDR1 comprising amino acids having the sequence set forth in SEQ ID NO: 32;

(b) a heavy chain variable region CDR3 comprising amino acids having the sequence set forth in SEQ ID NO:27; a light chain variable region CDR3 comprising amino acids having the sequence set forth in SEQ ID NO:47; a heavy chain variable region CDR2 comprising amino acids having the sequence set forth in SEQ ID NO: 21; a light chain variable region CDR2 comprising amino acids having the sequence set forth in SEQ ID NO: 40; a heavy chain variable region CDR1 comprising amino acids having the sequence set forth in SEQ ID NO: 15; and a light chain variable region CDR1 comprising amino acids having the sequence set forth in SEQ ID NO: 33;

(c) a heavy chain variable region CDR3 comprising amino acids having the sequence set forth in SEQ ID NO:28; a light chain variable region CDR3 comprising amino acids having the sequence set forth in SEQ ID NO:48; a heavy chain variable region CDR2 comprising amino acids having the sequence set forth in SEQ ID NO: 22; and a light chain variable region CDR2 comprising amino acids having the sequence set forth in SEQ ID NO: 41; a heavy chain variable region CDR1 comprising amino acids having the sequence set forth in SEQ ID NO: 16; and a light chain variable region CDR1 comprising amino acids having the sequence set forth in SEQ ID NO: 34;

(d) a heavy chain variable region CDR3 comprising amino acids having the sequence set forth in SEQ ID NO:28; a light chain variable region CDR3 comprising amino acids having the sequence set forth in SEQ ID NO:49; a heavy chain variable region CDR2 comprising amino acids having the sequence set forth in SEQ ID NO: 22; and a light chain variable region CDR2 comprising amino acids having the sequence set forth in SEQ ID NO: 42; a heavy chain variable region CDR1 comprising amino acids having the sequence set forth in SEQ ID NO: 16; and a light chain variable region CDR1 comprising amino acids having the sequence set forth in SEQ ID NO: 35;

(e) a heavy chain variable region CDR3 comprising amino acids having the sequence set forth in SEQ ID NO:29; a light chain variable region CDR3 comprising amino acids having the sequence set forth in SEQ ID NO:50; a heavy chain variable region CDR2 comprising amino acids having the sequence set forth in SEP ID NO: 23; and a light chain variable region CDR2 comprising amino acids having the sequence set forth in SEQ ID NO: 43; a heavy chain variable region CDR1 comprising amino acids having the sequence set forth in SEQ ID NO: 17; and a light chain variable region CDR1 comprising amino acids having the sequence set forth in SEQ ID NO: 36;

(f) a heavy chain variable region CDR3 comprising amino acids having the sequence set forth in SEQ ID NO:30; a light chain variable region CDR3 comprising amino acids having the sequence set forth in SEQ ID NO:51; a heavy chain variable region CDR2 comprising amino acids having the sequence set forth in SEQ ID NO: 24; and a ligh chain variable region CDR2 comprising amino acids having the sequence set forth in SEQ ID NO: 44; a heavy chain variable region CDR1 comprising amino acids having the sequence set forth in SEQ ID NO: 18; and a light chain variable region CDR1 comprising amino acids having the sequence set forth in SEQ ID NO: 37;

(g) a heavy chain variable region CDR3 comprising amino acids having the sequence set forth in SEQ ID NO:31; a light chain variable region CDR3 comprising amino acids having the sequence set forth in SEQ ID NO:52; a heavy chain variable region CDR2 comprising amino acids having the sequence set forth in SEQ ID NO: 25; and a light chain variable region CDR2 comprising amino acids having the sequence set forth in SEQ ID NO: 45; a heavy chain variable region CDR1 comprising amino acids having the sequence set forth in SEQ ID NO: 19; and a light chain variable region CDR1 comprising amino acids having the sequence set forth in SEQ ID NO: 38;

(h) a heavy chain variable region CDR3 comprising amino acids having the sequence set forth in SEQ ID NO:79; a light chain variable region CDR3 comprising amino acids having the sequence set forth in SEQ ID NO:82; a heavy chain variable region CDR2 comprising amino acids having the sequence set forth in SEQ ID NO: 78; and a light chain variable region CDR2 comprising amino acids having the sequence set forth in SEQ ID NO: 81; a heavy chain variable region CDR1 binding portion thereof comprises comprising amino acids having the sequence set forth in SEQ ID NO: 77; and a light chain variable region CDR1 comprising amino acids having the sequence set forth in SEQ ID NO: 80;

(i) a heavy chain variable region CDR3 comprising amino acids having the sequence set forth in SEQ ID NO:79; a light chain variable region CDR3 comprising amino acids having the sequence set forth in SEQ ID NO:97; a heavy chain variable region CDR2 comprising amino acids having the sequence set forth in SEQ ID NO: 78; and a light chain variable region CDR2 comprising amino acids having the sequence set forth in SEQ ID NO: 96; a heavy chain variable region CDR1 comprising amino acids having the sequence set forth in SEQ ID NO: 77; and a light chain variable region CDR1 comprising amino acids having the sequence set forth in SEQ ID NO: 95; or (j) a heavy chain variable region CDR3 comprising amino acids having the sequence set forth in SEQ ID NO:89; a light chain variable region CDR3 comprising amino acids having the sequence set forth in SEQ ID NO:92; a heavy chain variable region CDR2 comprising amino acids having the sequence set forth in SEQ ID NO: 88; and a light chain variable region CDR2 comprising amino acids having the sequence set forth in SEQ ID NO: 91; a heavy chain variable region CDR1 comprising amino acids having the sequence set forth in SEQ ID NO: 87; and a light chain variable region CDR1 comprising amino acids having the sequence set forth in SEQ ID NO: 90.

5. The antibody or antigen-binding portion thereof, of claim 1, wherein (a) the heavy chain variable region CDR3 comprises amino acids having the sequence set forth in SEQ ID NO: 26; the light chain variable region CDR3 comprises amino acids having the sequence set forth in SEQ ID NO: 46 and conservative modifications thereof; the heavy chain variable region CDR2 comprises amino acids having the sequence set forth in SEQ ID NO: 20 and conservative modifications thereof; and the light chain variable region CDR2 comprises amino acids having the sequence set forth in SEQ ID NO: 39 and conservative modifications thereof;

(b) the heavy chain variable region CDR3 comprises amino acids having the sequence set forth in SEQ ID NO: 27; the light chain variable region CDR3 comprises amino acids having the sequence set forth in SEQ ID NO: 47 and conservative modifications thereof; the heavy chain variable region CDR2 comprises amino acids having the sequence set forth in SEQ ID NO: 21 and conservative modifications thereof; and the light chain variable region CDR2 comprises amino acids having the sequence set forth in SEQ ID NO: 40 and conservative modifications thereof;

(c) the heavy chain variable region CDR3 comprises amino acids having the sequence set forth in SEQ ID NO: 28; the light chain variable region CDR3 comprises amino acids having the sequence set forth in SEQ ID NO: 48 and conservative modifications thereof; the heavy chain variable region CDR2 comprises amino acids having the sequence set forth in SEQ ID NO: 22 and conservative modifications thereof; and the light chain variable region CDR2 comprises amino acids having the sequence set forth in SEQ ID NO: 41 and conservative modifications thereof;

(d) the heavy chain variable region CDR3 comprises amino acids having the sequence set forth in SEQ ID NO: 28; the light chain variable region CDR3 comprises amino acids having the sequence set forth in SEQ ID NO: 49 and conservative modifications thereof; the heavy chain variable region CDR2 comprises amino acids having the sequence set forth in SEQ ID NO: 22 and conservative modifications thereof; and the light chain variable region CDR2 comprises amino acids having the sequence set forth in SEQ ID NO: 42 and conservative modifications thereof;

(e) the heavy chain variable region CDR3 comprises amino acids having the sequence set forth in SEQ ID NO: 29; the light chain variable region CDR3 comprises amino acids having the sequence set forth in SEQ ID NO: 50 and conservative modifications thereof; the heavy chain variable region CDR2 comprises amino acids having the sequence set forth in SEQ ID NO: 23 and conservative modifications thereof; and the light chain variable region CDR2 comprises amino acids having the sequence set forth in SEQ ID NO: 43 and conservative modifications thereof;

(f) the heavy chain variable region CDR3 comprises amino acids having the sequence set forth in SEQ ID NO: 30; the light chain variable region CDR3 comprises amino acids having the sequence set forth in SEQ ID NO: 51 and conservative modifications thereof; the heavy chain variable region CDR2 comprises amino acids having the sequence set forth in SEQ ID NO: 24 and conservative modifications thereof; and the light chain variable region CDR2 comprises amino acids having the sequence set forth in SEQ ID NO: 44 and conservative modifications thereof;

(g) the heavy chain variable region CDR3 comprises amino acids having the sequence set forth in SEQ ID NO: 31; the light chain variable region CDR3 comprises amino acids having the sequence set forth in SEQ ID NO: 52 and conservative modifications thereof; the heavy chain variable region CDR2 comprises amino acids having the sequence set forth in SEQ ID NO: 25 and conservative modifications thereof; and the light chain variable region CDR2 comprises amino acids having the sequence set forth in SEQ ID NO: 45 and conservative modifications thereof;

(h) the heavy chain variable region CDR3 comprises amino acids having the sequence set forth in SEQ ID NO: 79; the light chain variable region CDR3 comprises amino acids having the sequence set forth in SEQ ID NO: 82 and conservative modifications thereof; the heavy chain variable region CDR2 comprises amino acids having the sequence set forth in SEQ ID NO: 78 and conservative modifications thereof; and the light chain variable region CDR2 comprises amino acids having the sequence set forth in SEQ ID NO: 81 and conservative modifications thereof;

(i) the heavy chain variable region CDR3 comprises amino acids having the se uence set forth in SEQ ID NO: 79; the light chain variable region CDR3 comprises amino acids having the sequence set forth in SEQ ID NO: 97 and conservative modifications thereof; the heavy chain variable region CDR2 comprises amino acids having the sequence set forth in SEQ ID NO: 78 and conservative modifications thereof; and the light chain variable region CDR2 comprises amino acids having the sequence set forth in SEQ ID NO: 96 and conservative modifications thereof; or (j) the heavy chain variable region CDR3 comprises amino acids having the sequence set forth in SEQ ID NO: 89; the light chain variable region CDR3 comprises amino acids having the sequence set forth in SEQ ID NO: 92 and conservative modifications thereof; the heavy chain variable region CDR2 comprises amino acids having the sequence set forth in SEQ ID NO: 88 and conservative modifications thereof; and the light chain variable region CDR2 comprises amino acids having the sequence set forth in SEQ ID NO: 91 and conservative modifications thereof.

6. The antibody or antigen binding portion thereof, of claim 5, wherein (a) the heavy chain variable region CDR3 comprises amino acids having the sequence set forth in SEQ ID NO: 26; the light chain variable region CDR3 comprises amino acids havin the sequence set forth in SEQ ID NO: 46 and conservative modifications thereof; the heavy chain variable region CDR2 comprises amino acids having the sequence set forth in SEQ ID NO: 20 and conservative modifications thereof; the light chain variable region CDR2 comprises amino acids having the sequence set forth in SEQ ID NO: 39 and conservative modifications thereof, the heavy chain variable region CDR1 comprises amino acids having the sequence set forth in SEQ ID NO: 14 and conservative modifications thereof; and the light chain variable region CDR1 comprises amino acids having the sequence set forth in SEQ ID NO: 32 and conservative modifications thereof;

(b) the heavy chain variable region CDR3 comprises amino acids having the sequence set forth in SEQ ID NO: 27; the light chain variable region CDR3 comprises amino acids having the sequence set forth in SEQ ID NO: 47 and conservative modifications thereof; the heavy chain variable region CDR2 comprises amino acids having the sequence set forth in SEQ ID NO: 21 and conservative modifications thereof; the light chain variable region CDR2 comprises amino acids having the sequence set forth in SEQ ID NO: 40 and conservative modifications thereof; the heavy chain variable region CDR1 comprises amino acids having the sequence set forth in SEQ ID NO: 15 and conservative modifications thereof; and the light chain variable region CDR1 comprises amino acids having the sequence set forth in SEQ ID NO: 33 and conservative modifications thereof;

(c) the heavy chain variable region CDR3 comprises amino acids having the sequence set forth in SEQ ID NO: 28; the light chain variable region CDR3 comprises amino acids having the sequence set forth in SEQ ID NO: 48 and conservative modifications thereof; the heavy chain variable region CDR2 comprises amino acids having the sequence set forth in SEQ ID NO: 22 and conservative modifications thereof; the light chain variable region CDR2 comprises amino acids having the sequence set forth in SEQ ID NO: 41 and conservative modifications thereof; the heavy chain variable region CDR1 comprises amino acids having the sequence set forth in SEQ ID NO: 16 and conservative modifications thereof; and the light chain variable region CDR1 comprises amino acids having the sequence set forth in SEQ ID NO: 34 and conservative modifications thereof;

(d) the heavy chain variable region CDR3 comprises amino acids having the sequence set forth in SEQ ID NO: 28; the light chain variable region CDR3 comprises amino acids having the sequence set forth in SEQ ID NO: 49 and conservative modifications thereof; the heavy chain variable region CDR2 comprises amino acids having the sequence set forth in SEQ ID NO: 22 and conservative modifications thereof; the light chain variable region CDR2 comprises amino acids having the sequence set forth in SEQ ID NO: 42 and conservative modifications thereof; the heavy chain variable region CDR1 comprises amino acids having the sequence set forth in SEQ ID NO: 16 and conservative modifications thereof; and the light chain variable region CDR1 comprises amino acids having the sequence set forth in SEQ ID NO: 35 and conservative modifications thereof;

(e) the heavy chain variable region CDR3 comprises amino acids having the sequence set forth in SEQ ID NO: 29; the light chain variable region CDR3 comprises amino acids having the sequence set forth in SEQ ID NO: 50 and conservative modifications thereof; the heavy chain variable region CDR2 comprises amino acids having the sequence set forth in SEQ ID NO: 23 and conservative modifications thereof; the light chain variable region CDR2 comprises amino acids having the sequence set forth in SEQ ID NO: 43 and conservative modifications thereof the heavy chain variable region CDR1 comprises amino acids having the sequence set forth in SEQ ID NO: 17 and conservative modifications thereof; and the light chain variable region CDR1 comprises amino acids having the sequence set forth in SEQ ID NO: 36 and conservative modifications thereof;

(f) the heavy chain variable region CDR3 comprises amino acids having the sequence set forth in SEQ ID NO: 30; the light chain variable region CDR3 comprises amino acids having the sequence set forth in SEQ ID NO: 51 and conservative modifications thereof; the heavy chain variable region CDR2 comprises amino acids having the sequence set forth in SEQ ID NO: 24 and conservative modifications thereof; the light chain variable region CDR2 comprises amino acids having the sequence set forth in SEQ ID NO: 44 and conservative modifications thereof; the heavy chain variable region CDR1 comprises amino acids having the sequence set forth in SEQ ID NO: 18 and conservative modifications thereof; and the light chain variable region CDR1 comprises amino acids having the sequence set forth in SEQ ID NO: 37 and conservative modifications thereof;

(g) the heavy chain variable region CDR3 comprises amino acids having the sequence set forth in SEQ ID NO: 31; the light chain variable region CDR3 comprises amino acids having the sequence set forth in SEQ ID NO: 52 and conservative modifications thereof; the heavy chain variable region CDR2 comprises amino acids having the sequence set forth in SEQ ID NO: 25 and conservative modifications thereof; the light chain variable region CDR2 comprises amino acids having the sequence set forth in SEQ ID NO: 45 and conservative modifications thereof; the heavy chain variable region CDR1 comprises amino acids having the sequence set forth in SEQ ID NO: 19 and conservative modifications thereof; and the light chain variable region CDR1 comprises amino acids having the sequence set forth in SEQ ID NO: 38 and conservative modifications thereof;

(h) the heavy chain variable region CDR3 comprises amino acids having the sequence set forth in SEQ ID NO: 79; the light chain variable region CDR3 comprises amino acids having the sequence set forth in SEQ ID NO: 82 and conservative modifications thereof; the heavy chain variable region CDR2 comprises amino acids having the sequence set forth in SEQ ID NO: 78 and conservative modifications thereof; the light chain variable region CDR2 comprises amino acids having the sequence set forth in SEQ ID NO: 81 and conservative modifications thereof; the heavy chain variable region CDR1 comprises amino acids having the sequence set forth in SEQ ID NO: 77 and conservative modifications thereof; and the light chain variable region CDR1 comprises amino acids having the sequence set forth in SEQ ID NO: 80 and conservative modifications thereof;

(i) the heavy chain variable region CDR3 comprises amino acids having the sequence set forth in SEQ ID NO: 79; the light chain variable region CDR3 comprises amino acids having the sequence set forth in SEQ ID NO: 97 and conservative modifications thereof; the heavy chain variable region CDR2 comprises amino acids having the sequence set forth in SEQ ID NO: 78 and conservative modifications thereof; the light chain variable region CDR2 comprises amino acids having the sequence set forth in SEQ ID NO: 96 and conservative modifications thereof; the heavy chain variable region CDR1 comprises amino acids having the sequence set forth in SEQ ID NO: 77 and conservative modifications thereof; and the light chain variable region CDR1 comprises amino acids having the sequence set forth in SEQ ID NO: 95 and conservative modifications thereof; or (j) the heavy chain variable region CDR3 comprises amino acids having the sequence set forth in SEQ ID NO: 89; the light chain variable region CDR3 comprises amino acids having the sequence set forth in SEQ ID NO: 92 and conservative modifications thereof; the heavy chain variable region CDR2 comprises amino acids having the sequence set forth in SEQ ID NO: 88 and conservative modifications thereof; the light chain variable region CDR2 comprises amino acids having the sequence set forth in SEQ ID NO: 91 and conservative modifications thereof; the heavy chain variable region CDR1 comprises amino acids having the sequence set forth in SEQ ID NO: 87 and conservative modifications thereof; and the light chain variable region CDR1 comprises amino acids having the sequence set forth in SEQ ID NO: 90 and conservative modifications thereof.

7. The antibody or an antigen-binding portion thereof, of any one of claims 2-4, wherein the reference antibody or reference antigen-binding portion thereof comprises:
(a) a heavy chain variable region comprising amino acids having the sequence set forth in SEQ ID NO: 1; and a light chain variable region comprising amino acids having the sequence set forth in SEQ ID NO 7;
(b) a heavy chain variable region comprising amino acids having the sequence set forth in SEQ ID NO: 2; and a light chain variable region comprising amino acids having the sequence set forth in SEQ ID NO: 8;
(c) a heavy chain variable region comprising amino acids having the sequence set forth in SEQ ID NO: 3; and a light chain variable region comprising amino acids having the sequence set forth in SEQ ID NO: 9;
(d) a heavy chain variable region comprising amino acids having the sequence set forth in SEQ ID NO: 3; and a light chain variable region comprising amino acids having the sequence set forth in SEQ ID NO: 10;
(e) a heavy chain variable region comprising amino acids having the sequence set forth in SEQ ID NO: 4; and a light chain variable region comprising amino acids having the sequence set forth in SEQ ID NO: 11;
(f) a heavy chain variable region comprising amino acids having the sequence set forth in SEQ ID NO: 5; and a light chain variable region comprising amino acids having the sequence set forth in SEQ ID NO: 12;
(g) a heavy chain variable region comprising amino acids having the sequence set forth in SEQ ID NO: 6; and a light chain variable region comprising amino acids having the sequence set forth in SEQ ID NO: 13;
(h) a heavy chain variable region comprising amino acids having the sequence set forth in SEQ ID NO: 74; and a light chain variable region comprising amino acids having the sequence set forth in SEQ ID NO: 75;
(i) a heavy chain variable region comprising amino acids having the sequence set forth in SEQ ID NO: 74; and a light chain variable region comprising amino acids having the sequence set forth in SEQ ID NO: 76; or
(j) a heavy chain variable region comprising amino acids having the sequence set forth in SEQ ID NO: 85; and a light chain variable region comprising amino acids having the sequence set forth in SEQ ID NO: 86.

8. The antibody or an antigen-binding portion thereof, of claim 7, wherein the reference antibody or reference antigen-binding portion thereof comprises a heavy chain variable region comprising amino acids having the sequence set forth in SEQ ID NO: 3; and a light chain variable region comprising amino acids having the sequence set forth in SEQ ID NO 9.

9. The antibody or an antigen-binding portion thereof, of claim 7, wherein the reference antibody or reference antigen-binding portion thereof comprises a heavy chain variable region comprising amino acids having the sequence set forth in SEQ ID NO: 5; and a light chain variable region comprising amino acids having the sequence set forth in SEQ ID NO 12.

10. The isolated monoclonal antibody, or antigen binding portion thereof, of claim 1, comprising:

(a) a heavy chain variable region CDR1 comprising amino acid sequence of SEQ ID NO:16;
(b) a heavy chain variable region CDR2 comprising amino acid sequence of SEQ ID NO:22;
(c) a heavy chain variable region CDR3 comprising amino acid sequence of SEQ ID NO:28;
(d) a light chain variable region CDR1 comprising amino acid sequence of SEQ ID NO:34;
(e) a light chain variable region CDR2 comprising amino acid sequence of SEQ ID NO:41; and
(f) a light chain variable region CDR3 comprising amino acid sequence of SEQ ID NO:48;
wherein antibody specifically binds BTLA.

11. The isolated monoclonal antibody, or antigen binding portion thereof, of claim 1, comprising:
(a) a heavy chain variable region CDR1 comprising amino acid sequence of SEQ ID NO:18;
(b) a heavy chain variable region CDR2 comprising amino acid sequence of SEQ ID NO:24;
(c) a heavy chain variable region CDR3 comprising amino acid sequence of SEQ ID NO:30;
(d) a light chain variable region CDR1 comprising amino acid sequence of SEQ ID NO:37;
(e) a light chain variable region CDR2 comprising amino acid sequence of SEQ ID NO:44; and
(f) a light chain variable region CDR3 comprising amino acid sequence of SEQ ID NO:51;
wherein antibody specifically binds BTLA.

12. The isolated monoclonal antibody, or antigen binding portion thereof, of claim 1, wherein antibody or antigen-binding portion thereof comprises a heavy chain variable region comprising amino acids having the sequence set forth in SEQ ID NO: 3; and a light chain variable region comprising amino acids having the sequence set forth in SEQ ID NO 9.

13. The isolated monoclonal antibody, or antigen binding portion thereof, of claim 1, wherein antibody or antigen-binding portion thereof comprises a heavy chain variable region comprising amino acids having the sequence set forth in SEQ ID NO: 5; and a light chain variable region comprising amino acids having the sequence set forth in SEQ ID NO 12.

14. The antibody or antigen-binding portion thereof, of claim 1 or 2, wherein antibody or antigen-binding portion thereof, is linked to a therapeutic agent.

15. The antibody or antigen binding portion thereof, of claim 14, wherein the therapeutic agent is a cytotoxin.

16. The antibody or antigen binding portion thereof, of claim 14, wherein the therapeutic agent is a radioactive isotope.

17. The antibody or antigen-binding portion thereof, of claim 1 or 2, linked to a second functional moiety having a different binding specificity than said antibody or antigen binding portion thereof.

18. A pharmaceutical composition comprising antibody or antigen-binding portion thereof, of claim 1 or 2, and a pharmaceutically acceptable carrier.

* * * * *

UNITED STATES PATENT AND TRADEMARK OFFICE
CERTIFICATE OF CORRECTION

| | |
|---|---|
| PATENT NO. | : 8,247,537 B2 |
| APPLICATION NO. | : 12/515004 |
| DATED | : August 21, 2012 |
| INVENTOR(S) | : Alan Korman et al. |

It is certified that error appears in the above-identified patent and that said Letters Patent is hereby corrected as shown below:

Column 117, claim 2, line 34: "wherein antibody" should read -- wherein the antibody --

Column 118, claim 2, line 28: "SEQ 7ID NO" should read -- SEQ ID NO --

Column 118, claim 3, line 60: "N0" should read -- NO --

Column 120, claim 4, line 66: "SEP" should read -- SEQ --

Column 128, claim 12, line 2: "wherein antibody" should read -- wherein the antibody --

Column 128, claim 13, line 8: "wherein antibody" should read -- wherein the antibody --

Column 128, claim 14, line 14: "wherein antibody" should read -- wherein the antibody --

Column 128, claim 18, line 25: "comprising antibody" should read -- comprising the antibody --

Signed and Sealed this
Twenty-third Day of October, 2012

David J. Kappos
*Director of the United States Patent and Trademark Office*

SEQUENCE LISTING

```
<160> NUMBER OF SEQ ID NOS: 100

<210> SEQ ID NO 1
<211> LENGTH: 128
<212> TYPE: PRT
<213> ORGANISM: Homo sapiens

<400> SEQUENCE: 1

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Asn Thr Ile
            20                  25                  30

Gly Val Gly Val Asn Trp Ile Arg Gln Pro Pro Gly Lys Ala Leu Glu
        35                  40                  45

Trp Leu Ala Leu Ile Tyr Trp Asp Asp Lys Arg Tyr Ser Pro Ser
```

```
                50                  55                  60
Leu Lys Arg Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala His Ser Gly Ile Thr Glu Val Arg Gly Val Ile Ile His Tyr
                100                 105                 110

Tyr Gly Met Asp Val Trp Gly Gln Gly Thr Thr Val Thr Val Ser Ser
                115                 120                 125

<210> SEQ ID NO 2
<211> LENGTH: 128
<212> TYPE: PRT
<213> ORGANISM: Homo sapiens

<400> SEQUENCE: 2

Gln Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
                 20                  25                  30

Gly Met Cys Val Ser Trp Ile Arg Gln Pro Pro Gly Lys Ala Leu Glu
                 35                  40                  45

Trp Leu Ala Leu Ile Asp Trp Asp Asp Val Lys Tyr Tyr Ser Ser Ser
 50                  55                  60

Leu Lys Thr Arg Leu Thr Ile Ser Lys Asp Thr Ser Lys Asn Gln Val
 65                  70                  75                  80

Val Leu Thr Met Thr Asp Met Asp Pro Val Asp Thr Ala Thr Tyr Tyr
                 85                  90                  95

Cys Ala Arg Ile Arg Phe Thr Met Phe Arg Gly Val Tyr Tyr Tyr Tyr
                100                 105                 110

Tyr Gly Leu Asp Val Trp Gly Gln Gly Thr Thr Val Thr Val Ser Ser
                115                 120                 125

<210> SEQ ID NO 3
<211> LENGTH: 120
<212> TYPE: PRT
<213> ORGANISM: Homo sapiens

<400> SEQUENCE: 3

Gln Val Gln Leu Gln Glu Ser Gly Pro Gly Leu Val Lys Pro Ser Glu
  1               5                  10                  15

Thr Leu Ser Leu Thr Cys Thr Ile Ser Gly Gly Ser Ile Ser Asn Tyr
                 20                  25                  30

Tyr Trp Asn Trp Ile Arg Gln Pro Pro Gly Lys Gly Leu Glu Trp Ile
                 35                  40                  45

Gly Tyr Ile Tyr Tyr Ser Thr Ser Thr Lys Tyr Asn Pro Ser Leu Lys
 50                  55                  60

Ser Arg Val Thr Met Ser Val Glu Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Val Lys Val Tyr Ser Thr Gly Trp Phe Phe Asp Tyr Trp Gly Gln
                100                 105                 110

Gly Thr Leu Val Thr Val Ser Ser
                115                 120

<210> SEQ ID NO 4
```

```
<211> LENGTH: 128
<212> TYPE: PRT
<213> ORGANISM: Homo sapiens

<400> SEQUENCE: 4

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asp Asp Asp Lys Arg Tyr Ser Pro Ser
50                  55                  60

Leu Lys Ser Arg Leu Thr Ile Thr Lys Asp Thr Ser Lys Asn Gln Val
65                  70                  75                  80

Val Leu Thr Met Ala Asn Met Asp Pro Val Asp Thr Ala Thr Tyr Tyr
                85                  90                  95

Cys Ala His Ile Arg Ile Thr Glu Val Arg Gly Val Ile Ile Ser Tyr
            100                 105                 110

Tyr Gly Met Asp Val Trp Gly Gln Gly Thr Thr Val Thr Val Ser Ser
        115                 120                 125

<210> SEQ ID NO 5
<211> LENGTH: 127
<212> TYPE: PRT
<213> ORGANISM: Homo sapiens

<400> SEQUENCE: 5

Glu Val Gln Leu Val Glu Ser Gly Gly Gly Val Ile Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Ala Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Ser Ala Leu Tyr Tyr Cys
                85                  90                  95

Ala Arg Asp Tyr Tyr Tyr Gly Pro Gly Ser Pro Asn Tyr Phe Tyr Tyr
            100                 105                 110

Ala Met Asp Val Trp Gly Gln Gly Thr Thr Val Thr Val Ser Ser
        115                 120                 125

<210> SEQ ID NO 6
<211> LENGTH: 128
<212> TYPE: PRT
<213> ORGANISM: Homo sapiens

<400> SEQUENCE: 6

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asp Asp Asp Lys Arg Tyr Ser Pro Ser
```

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Thr Ser Ile Thr Glu Val Arg Gly Ala Ile Ile Tyr Tyr
            100                 105                 110

Tyr Gly Met Asp Val Trp Gly Gln Gly Thr Thr Val Thr Val Ser Ser
        115                 120                 125

<210> SEQ ID NO 7
<211> LENGTH: 107
<212> TYPE: PRT
<213> ORGANISM: Homo sapiens

<400> SEQUENCE: 7

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Ile
                85                  90                  95

Thr Phe Gly Gln Gly Thr Arg Leu Glu Ile Lys
            100                 105

<210> SEQ ID NO 8
<211> LENGTH: 109
<212> TYPE: PRT
<213> ORGANISM: Homo sapiens

<400> SEQUENCE: 8

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Ile Thr Phe Gly Pro Gly Thr Lys Val Asp Ile Lys
            100                 105

<210> SEQ ID NO 9
<211> LENGTH: 107
<212> TYPE: PRT
<213> ORGANISM: Homo sapiens

<400> SEQUENCE: 9

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105
```

<210> SEQ ID NO 10
<211> LENGTH: 108
<212> TYPE: PRT
<213> ORGANISM: Homo sapiens

<400> SEQUENCE: 10

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys
            100                 105
```

<210> SEQ ID NO 11
<211> LENGTH: 109
<212> TYPE: PRT
<213> ORGANISM: Homo sapiens

<400> SEQUENCE: 11

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Ile Thr Phe Gly Gln Gly Thr Arg Leu Glu Ile Lys
            100                 105
```

```
<210> SEQ ID NO 12
<211> LENGTH: 107
<212> TYPE: PRT
<213> ORGANISM: Homo sapiens

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys
            100                 105

<210> SEQ ID NO 13
<211> LENGTH: 107
<212> TYPE: PRT
<213> ORGANISM: Homo sapiens

<400> SEQUENCE: 13

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly His Ser Leu
                85                  90                  95

Thr Phe Gly Gly Gly Thr Lys Val Glu Ile Lys
            100                 105

<210> SEQ ID NO 14
<211> LENGTH: 7
<212> TYPE: PRT
<213> ORGANISM: Homo sapiens

<400> SEQUENCE: 14

Thr Ile Gly Val Gly Val Asn
1               5

<210> SEQ ID NO 15
<211> LENGTH: 7
<212> TYPE: PRT
<213> ORGANISM: Homo sapiens

<400> SEQUENCE: 15

Thr Ser Gly Met Cys Val Ser
1               5
```

```
<210> SEQ ID NO 16
<211> LENGTH: 5
<212> TYPE: PRT
<213> ORGANISM: Homo sapiens

<400> SEQUENCE: 16

Asn Tyr Tyr Trp Asn
1               5

<210> SEQ ID NO 17
<211> LENGTH: 7
<212> TYPE: PRT
<213> ORGANISM: Homo sapiens

<400> SEQUENCE: 17

Thr Ser Gly Val Gly Val Gly
1               5

<210> SEQ ID NO 18
<211> LENGTH: 5
<212> TYPE: PRT
<213> ORGANISM: Homo sapiens

<400> SEQUENCE: 18

Asp Tyr Gly Met Ser
1               5

<210> SEQ ID NO 19
<211> LENGTH: 7
<212> TYPE: PRT
<213> ORGANISM: Homo sapiens

<400> SEQUENCE: 19

Thr Ser Gly Val Gly Val Gly
1               5

<210> SEQ ID NO 20
<211> LENGTH: 16
<212> TYPE: PRT
<213> ORGANISM: Homo sapiens

<400> SEQUENCE: 20

Leu Ile Tyr Trp Asp Asp Asp Lys Arg Tyr Ser Pro Ser Leu Lys Arg
1               5                   10                  15

<210> SEQ ID NO 21
<211> LENGTH: 16
<212> TYPE: PRT
<213> ORGANISM: Homo sapiens

<400> SEQUENCE: 21

Leu Ile Asp Trp Asp Asp Val Lys Tyr Tyr Ser Ser Ser Leu Lys Thr
1               5                   10                  15

<210> SEQ ID NO 22
<211> LENGTH: 16
<212> TYPE: PRT
<213> ORGANISM: Homo sapiens

<400> SEQUENCE: 22

Tyr Ile Tyr Tyr Ser Thr Ser Thr Lys Tyr Asn Pro Ser Leu Lys Ser
1               5                   10                  15

<210> SEQ ID NO 23
<211> LENGTH: 16
<212> TYPE: PRT
```

<213> ORGANISM: Homo sapiens

<400> SEQUENCE: 23

Leu Ile Tyr Trp Asp Asp Asp Lys Arg Tyr Ser Pro Ser Leu Lys Ser
1               5                   10                  15

<210> SEQ ID NO 24
<211> LENGTH: 17
<212> TYPE: PRT
<213> ORGANISM: Homo sapiens

<400> SEQUENCE: 24

Gly Ile Asn Trp Asn Gly Gly Ser Thr Gly Tyr Ala Ala Ser Val Lys
1               5                   10                  15

Gly

<210> SEQ ID NO 25
<211> LENGTH: 16
<212> TYPE: PRT
<213> ORGANISM: Homo sapiens

<400> SEQUENCE: 25

Leu Ile Tyr Trp Asp Asp Asp Lys Arg Tyr Ser Pro Ser Leu Lys Ser
1               5                   10                  15

<210> SEQ ID NO 26
<211> LENGTH: 18
<212> TYPE: PRT
<213> ORGANISM: Homo sapiens

<400> SEQUENCE: 26

Ser Gly Ile Thr Glu Val Arg Gly Val Ile His Tyr Tyr Gly Met
1               5                   10                  15

Asp Val

<210> SEQ ID NO 27
<211> LENGTH: 18
<212> TYPE: PRT
<213> ORGANISM: Homo sapiens

<400> SEQUENCE: 27

Ile Arg Phe Thr Met Phe Arg Gly Val Tyr Tyr Tyr Tyr Gly Leu
1               5                   10                  15

Asp Val

<210> SEQ ID NO 28
<211> LENGTH: 12
<212> TYPE: PRT
<213> ORGANISM: Homo sapiens

<400> SEQUENCE: 28

Val Lys Val Tyr Ser Thr Gly Trp Phe Phe Asp Tyr
1               5                   10

<210> SEQ ID NO 29
<211> LENGTH: 18
<212> TYPE: PRT
<213> ORGANISM: Homo sapiens

<400> SEQUENCE: 29

Ile Arg Ile Thr Glu Val Arg Gly Val Ile Ile Ser Tyr Tyr Gly Met
1               5                   10                  15

Asp Val

```
<210> SEQ ID NO 30
<211> LENGTH: 18
<212> TYPE: PRT
<213> ORGANISM: Homo sapiens

<400> SEQUENCE: 30

Asp Tyr Tyr Tyr Gly Pro Gly Ser Pro Asn Tyr Phe Tyr Tyr Ala Met
1               5                   10                  15

Asp Val

<210> SEQ ID NO 31
<211> LENGTH: 18
<212> TYPE: PRT
<213> ORGANISM: Homo sapiens

<400> SEQUENCE: 31

Thr Ser Ile Thr Glu Val Arg Gly Ala Ile Ile Tyr Tyr Tyr Gly Met
1               5                   10                  15

Asp Val

<210> SEQ ID NO 32
<211> LENGTH: 12
<212> TYPE: PRT
<213> ORGANISM: Homo sapiens

<400> SEQUENCE: 32

Arg Ala Ser Gln Ser Val Ser Ser Ser Tyr Leu Ala
1               5                   10

<210> SEQ ID NO 33
<211> LENGTH: 12
<212> TYPE: PRT
<213> ORGANISM: Homo sapiens

<400> SEQUENCE: 33

Arg Ala Ser Gln Ser Val Ser Ser Ser Tyr Leu Ala
1               5                   10

<210> SEQ ID NO 34
<211> LENGTH: 11
<212> TYPE: PRT
<213> ORGANISM: Homo sapiens

<400> SEQUENCE: 34

Arg Ala Ser Gln Gly Ile Ser Ser Ala Leu Ala
1               5                   10

<210> SEQ ID NO 35
<211> LENGTH: 12
<212> TYPE: PRT
<213> ORGANISM: Homo sapiens

<400> SEQUENCE: 35

Arg Ala Ser Gln Ser Val Ser Ser Ser Tyr Leu Ala
1               5                   10

<210> SEQ ID NO 36
<211> LENGTH: 12
<212> TYPE: PRT
<213> ORGANISM: Homo sapiens

<400> SEQUENCE: 36

Arg Ala Ser Gln Ser Val Ser Ser Thr Tyr Leu Ala
```

<210> SEQ ID NO 37
<211> LENGTH: 11
<212> TYPE: PRT
<213> ORGANISM: Homo sapiens

<400> SEQUENCE: 37

Arg Ala Ser Gln Gly Ile Ser Ser Trp Leu Ala
1               5                   10

<210> SEQ ID NO 38
<211> LENGTH: 12
<212> TYPE: PRT
<213> ORGANISM: Homo sapiens

<400> SEQUENCE: 38

Arg Ala Ser Gln Ser Val Ser Ser Ser Tyr Leu Ala
1               5                   10

<210> SEQ ID NO 39
<211> LENGTH: 7
<212> TYPE: PRT
<213> ORGANISM: Homo sapiens

<400> SEQUENCE: 39

Gly Ala Ser Ser Arg Ala Thr
1               5

<210> SEQ ID NO 40
<211> LENGTH: 7
<212> TYPE: PRT
<213> ORGANISM: Homo sapiens

<400> SEQUENCE: 40

Gly Ala Ser Ser Arg Ala Thr
1               5

<210> SEQ ID NO 41
<211> LENGTH: 7
<212> TYPE: PRT
<213> ORGANISM: Homo sapiens

<400> SEQUENCE: 41

Asp Ala Ser Ser Leu Glu Ser
1               5

<210> SEQ ID NO 42
<211> LENGTH: 7
<212> TYPE: PRT
<213> ORGANISM: Homo sapiens

<400> SEQUENCE: 42

Gly Ala Ser Ser Arg Ala Thr
1               5

<210> SEQ ID NO 43
<211> LENGTH: 7
<212> TYPE: PRT
<213> ORGANISM: Homo sapiens

<400> SEQUENCE: 43

Gly Ala Ser Ser Arg Ala Thr
1               5

```
<210> SEQ ID NO 44
<211> LENGTH: 7
<212> TYPE: PRT
<213> ORGANISM: Homo sapiens

<400> SEQUENCE: 44

Ala Ala Ser Ser Leu Gln Ser
1               5

<210> SEQ ID NO 45
<211> LENGTH: 7
<212> TYPE: PRT
<213> ORGANISM: Homo sapiens

<400> SEQUENCE: 45

Gly Ala Ser Ser Arg Ala Thr
1               5

<210> SEQ ID NO 46
<211> LENGTH: 8
<212> TYPE: PRT
<213> ORGANISM: Homo sapiens

<400> SEQUENCE: 46

Gln Gln Tyr Gly Ser Ser Ile Thr
1               5

<210> SEQ ID NO 47
<211> LENGTH: 10
<212> TYPE: PRT
<213> ORGANISM: Homo sapiens

<400> SEQUENCE: 47

Gln Gln Tyr Gly Ser Ser Pro Pro Ile Thr
1               5                   10

<210> SEQ ID NO 48
<211> LENGTH: 9
<212> TYPE: PRT
<213> ORGANISM: Homo sapiens

<400> SEQUENCE: 48

Gln Gln Phe Asn Ser Tyr Pro Leu Thr
1               5

<210> SEQ ID NO 49
<211> LENGTH: 9
<212> TYPE: PRT
<213> ORGANISM: Homo sapiens

<400> SEQUENCE: 49

Gln Gln Tyr Gly Ser Ser Pro Tyr Thr
1               5

<210> SEQ ID NO 50
<211> LENGTH: 10
<212> TYPE: PRT
<213> ORGANISM: Homo sapiens

<400> SEQUENCE: 50

Gln Gln Tyr Gly Ser Ser Pro Pro Ile Thr
1               5                   10

<210> SEQ ID NO 51
<211> LENGTH: 9
<212> TYPE: PRT
```

<213> ORGANISM: Homo sapiens

<400> SEQUENCE: 51

Gln Gln Tyr Asn Ser Tyr Pro Arg Thr
1               5

<210> SEQ ID NO 52
<211> LENGTH: 8
<212> TYPE: PRT
<213> ORGANISM: Homo sapiens

<400> SEQUENCE: 52

Gln Gln Tyr Gly His Ser Leu Thr
1               5

<210> SEQ ID NO 53
<211> LENGTH: 384
<212> TYPE: DNA
<213> ORGANISM: Homo sapiens

<400> SEQUENCE: 53

| | | | | | |
|---|---|---|---|---|---|
| cagatcacct | tgaaggagtc | tggtcctacg | ctggtgaaac | ccacacagac | cctcacgctg | 60 |
| acctgcacct | tctctgggtt | ctcactcaac | actattggag | tgggtgtaaa | ctggatccgt | 120 |
| cagcccccag | gaaaggccct | ggagtggctt | gcactcattt | attgggatga | tgataagcgc | 180 |
| tacagcccat | ctctgaagag | gaggctcacc | atctccaagg | acacctccaa | aaaccaggtg | 240 |
| gtccttcacaa | tgaccaacat | ggaccctgtg | gacacagcca | catattactg | tgcacacagc | 300 |
| gggattactg | aggttcgggg | agttattata | cattactacg | gtatggacgt | ctggggccaa | 360 |
| gggaccacgg | tcaccgtctc | ctca | | | | 384 |

<210> SEQ ID NO 54
<211> LENGTH: 384
<212> TYPE: DNA
<213> ORGANISM: Homo sapiens

<400> SEQUENCE: 54

| | | | | | |
|---|---|---|---|---|---|
| caggtcacct | tgagggagtc | tggtcctgcg | ctggtgaaac | ccacacagac | cctcacactg | 60 |
| acctgcacct | tctctgggtt | ctcactcagc | actagtggaa | tgtgtgtgag | ctggatccgt | 120 |
| cagcccccag | ggaaggccct | ggagtggctt | gcactcattg | attgggatga | tgttaaatac | 180 |
| tacagctcat | ctctgaagac | caggctcacc | atctccaagg | acacctccaa | aaaccaggtg | 240 |
| gtccttacaa | tgaccgacat | ggaccctgtg | gacactgcca | cgtattactg | tgcacggata | 300 |
| cggtttacta | tgtttcgggg | agtctactac | tattactacg | gtttggacgt | ctggggccaa | 360 |
| gggaccacgg | tcaccgtctc | ctca | | | | 384 |

<210> SEQ ID NO 55
<211> LENGTH: 360
<212> TYPE: DNA
<213> ORGANISM: Homo sapiens

<400> SEQUENCE: 55

| | | | | | |
|---|---|---|---|---|---|
| caggtgcagc | tgcaggagtc | gggcccagga | ctggtgaagc | cttcggagac | cctgtccctc | 60 |
| acctgcacta | tctctggtgg | ctccatcagt | aattactact | ggaactggat | ccggcagccc | 120 |
| ccagggaagg | gactggagtg | gattgggtat | atctattaca | gtacgagcac | caagtacaac | 180 |
| ccctccctca | agagtcgagt | caccatgtca | gtagagacgt | ccaagaacca | gttctccctg | 240 |
| aagctgagct | ctgtgaccgc | tgcggacacg | gccgtgtatt | actgtgcgag | agtgaaagtg | 300 |

```
tatagcactg gctggttctt tgactactgg ggccagggaa ccctggtcac cgtctcctca      360
```

<210> SEQ ID NO 56
<211> LENGTH: 384
<212> TYPE: DNA
<213> ORGANISM: Homo sapiens

<400> SEQUENCE: 56

```
cagatcacct tgaaggagtc tggtcctacg ctggtgaaac ccacacagac cctcacgctg      60
acctgcacct tttctgggtt ctcactcagc actagtggag tgggtgtggg ctggatccgt     120
cagcccccag gaaaggccct ggagtggctt gcactcattt attgggatga tgataagcgc     180
tacagtccat ctctgaagag caggctcacc atcaccaagg acacctccaa aaaccaggtg     240
gtccttacaa tggccaacat ggaccctgtg gacacagcca catattactg tgcacacatc     300
cgtattactg aggttcgggg agttattatc tcctactacg gtatggacgt ctggggccaa     360
gggaccacgg tcaccgtctc ctca                                            384
```

<210> SEQ ID NO 57
<211> LENGTH: 381
<212> TYPE: DNA
<213> ORGANISM: Homo sapiens

<400> SEQUENCE: 57

```
gaggtgcaac tggtggagtc tgggggaggt gtgatacggc ctggggggtc cctgagactc      60
tcctgtgcag cctctggatt cacctttgat gattatggca tgagctgggt ccgccaagct     120
ccagggaagg ggctggagtg ggtctctggt attaattgga atggtggtag cacaggttat     180
gcagcctctg tgaagggccg attcaccatc tccagagaca acgccaagaa ctccctgtat     240
ctacaaatga acagtctgag agccgaggac tcggccttgt attactgtgc gagagattat     300
tactatggtc cggggagtcc taactacttc tactacgcta tggacgtctg ggccaaggg      360
accacggtca ccgtctcctc a                                               381
```

<210> SEQ ID NO 58
<211> LENGTH: 384
<212> TYPE: DNA
<213> ORGANISM: Homo sapiens

<400> SEQUENCE: 58

```
cagatcacct tgaaggagtc tggtcctacg ctggtgaaac ccacacagac cctcacgctg      60
acctgcacct tctctgggtt ctcactcagc actagtggag tgggtgtggg ctggatccgt     120
cagcccccag gaaaggccct ggagtggctt gcactcattt attgggatga tgataagcgc     180
tacagcccat ctctgaagag caggctcacc atcaccaagg acacctccaa aaaccaggtg     240
gtccttacaa tgaccaacat ggaccctgtg gacacagcca catattactg tgcacacacc     300
agtattactg aggttcgggg agctattatc tactactacg gtatggacgt ctggggccaa     360
gggaccacgg tcaccgtctc ctca                                            384
```

<210> SEQ ID NO 59
<211> LENGTH: 321
<212> TYPE: DNA
<213> ORGANISM: Homo sapiens

<400> SEQUENCE: 59

```
gaaattgtgt tgacgcagtc tccaggcacc ctgtctttgt ctccagggga aagagccacc      60
ctctcctgca gggccagtca gagtgttagc agcagctact tagcctggta ccagcagaaa     120
```

```
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcaatcac cttcggccaa    300
gggacacgac tggagattaa a                                              321

<210> SEQ ID NO 60
<211> LENGTH: 327
<212> TYPE: DNA
<213> ORGANISM: Homo sapiens

<400> SEQUENCE: 60
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcacctcc gatcactttc    300
ggccctggga ccaaagtgga tatcaaa                                        327

<210> SEQ ID NO 61
<211> LENGTH: 321
<212> TYPE: DNA
<213> ORGANISM: Homo sapiens

<400> SEQUENCE: 61
gccatccagt tgacccagtc tccatcctcc ctgtctgcat ctgtaggaga cagagtcacc     60
atcacttgcc gggcaagtca gggcattagc agtgctttag cctggtatca gcagaaacca    120
gggaaagctc ctaagctcct gatctatgat gcctccagtt tggaaagtgg ggtcccatca    180
aggttcagcg gcagtggatc tgggacagat ttcactctca ccatcagcag cctgcagcct    240
gaagattttg caacttatta ctgtcaacag tttaatagtt accctctcac tttcggcgga    300
gggaccaagg tggagatcaa a                                              321

<210> SEQ ID NO 62
<211> LENGTH: 324
<212> TYPE: DNA
<213> ORGANISM: Homo sapiens

<400> SEQUENCE: 62
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcaccgta cacttttggc    300
caggggacca agctggagat caaa                                           324

<210> SEQ ID NO 63
<211> LENGTH: 327
<212> TYPE: DNA
<213> ORGANISM: Homo sapiens

<400> SEQUENCE: 63
gaaattgtgt tgacgcagtc tccaggcacc ctgtctttgt ctccagggga aagagccacc     60
ctctcctgca gggccagtca gagtgttagc agcacctact tagcctggta ccagcagaaa    120
```

```
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcacctcc gatcaccttc    300
ggccaaggga cacgactgga gattaaa                                        327
```

<210> SEQ ID NO 64
<211> LENGTH: 321
<212> TYPE: DNA
<213> ORGANISM: Homo sapiens

<400> SEQUENCE: 64

```
gacatccaga tgacccagtc tccatcctca ctgtctgcat ctgtaggaga cagagtcacc     60
atcacttgtc gggcgagtca gggtattagc agctggttag cctggtatca gcagaaacca    120
gagaaagccc ctaagtccct gatctatgct gcatccagtt tgcaaagtgg ggtcccatca    180
aggttcagcg gcagtggatc tgggacagat ttcactctca ccatcagcag cctgcagcct    240
gaagattttg caacttatta ctgccaacag tataatagtt accctcggac gttcggccaa    300
gggaccaagg tggaaatcaa a                                              321
```

<210> SEQ ID NO 65
<211> LENGTH: 321
<212> TYPE: DNA
<213> ORGANISM: Homo sapiens

<400> SEQUENCE: 65

```
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggtc actcgctcac tttcggcgga    300
gggaccaagg tggagatcaa a                                              321
```

<210> SEQ ID NO 66
<211> LENGTH: 100
<212> TYPE: PRT
<213> ORGANISM: Homo sapiens

<400> SEQUENCE: 66

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg
            100

<210> SEQ ID NO 67
<211> LENGTH: 100

```
<212> TYPE: PRT
<213> ORGANISM: Homo sapiens

<400> SEQUENCE: 67

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Cys Val Ser Trp Ile Arg Gln Pro Pro Gly Lys Ala Leu Glu
        35                  40                  45

Trp Leu Ala Leu Ile Asp Trp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile
            100

<210> SEQ ID NO 68
<211> LENGTH: 97
<212> TYPE: PRT
<213> ORGANISM: Homo sapiens

<400> SEQUENCE: 68

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 69
<211> LENGTH: 98
<212> TYPE: PRT
<213> ORGANISM: Homo sapiens

<400> SEQUENCE: 69

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95
```

Ala Arg

<210> SEQ ID NO 70
<211> LENGTH: 95
<212> TYPE: PRT
<213> ORGANISM: Homo sapiens

<400> SEQUENCE: 70

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser
                85                  90                  95
```

<210> SEQ ID NO 71
<211> LENGTH: 95
<212> TYPE: PRT
<213> ORGANISM: Homo sapiens

<400> SEQUENCE: 71

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro
                85                  90                  95
```

<210> SEQ ID NO 72
<211> LENGTH: 95
<212> TYPE: PRT
<213> ORGANISM: Homo sapiens

<400> SEQUENCE: 72

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                85                  90                  95
```

<210> SEQ ID NO 73
<211> LENGTH: 289
<212> TYPE: PRT
<213> ORGANISM: Homo sapiens

<400> SEQUENCE: 73

Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
            20                  25                  30

Ser Cys Asp Val Gln Leu Tyr Ile Lys Arg Gln Ser Glu His Ser Ile
        35                  40                  45

Leu Ala Gly Asp Pro Phe Glu Leu Glu Cys Pro Val Lys Tyr Cys Ala
    50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Lys Asn Ile Ser
                85                  90                  95

Phe Phe Ile Leu His Phe Glu Pro Val Leu Pro Asn Asp Asn Gly Ser
            100                 105                 110

Tyr Arg Cys Ser Ala Asn Phe Gln Ser Asn Leu Ile Glu Ser His Ser
        115                 120                 125

Thr Thr Leu Tyr Val Thr Asp Val Lys Ser Ala Ser Glu Arg Pro Ser
    130                 135                 140

Lys Asp Glu Met Ala Ser Arg Pro Trp Leu Leu Tyr Ser Leu Leu Pro
145                 150                 155                 160

Leu Gly Gly Leu Pro Leu Leu Ile Thr Thr Cys Phe Cys Leu Phe Cys
                165                 170                 175

Cys Leu Arg Arg His Gln Gly Lys Gln Asn Glu Leu Ser Asp Thr Ala
            180                 185                 190

Gly Arg Glu Ile Asn Leu Val Asp Ala His Leu Lys Ser Glu Gln Thr
        195                 200                 205

Glu Ala Ser Thr Arg Gln Asn Ser Gln Val Leu Leu Ser Glu Thr Gly
    210                 215                 220

Ile Tyr Asp Asn Asp Pro Asp Leu Cys Phe Arg Met Gln Glu Gly Ser
225                 230                 235                 240

Glu Val Tyr Ser Asn Pro Cys Leu Glu Glu Asn Lys Pro Gly Ile Val
                245                 250                 255

Tyr Ala Ser Leu Asn His Ser Val Ile Gly Pro Asn Ser Arg Leu Ala
            260                 265                 270

Arg Asn Val Lys Glu Ala Pro Thr Glu Tyr Ala Ser Ile Cys Val Arg
        275                 280                 285

Ser

<210> SEQ ID NO 74
<211> LENGTH: 127
<212> TYPE: PRT
<213> ORGANISM: Homo sapiens

<400> SEQUENCE: 74

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Ala Ile Trp Asn Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Arg Ile Thr Met Val Arg Gly Val Ile Thr Gln Tyr Tyr
                100                 105                 110

Gly Met Asp Val Trp Gly Gln Gly Thr Thr Val Thr Val Ser Ser
                115                 120                 125

<210> SEQ ID NO 75
<211> LENGTH: 107
<212> TYPE: PRT
<213> ORGANISM: Homo sapiens

<400> SEQUENCE: 75

Asp Ile Gln Leu Thr Gln Ser Pro Ser Ser Leu Ser Ala Ser Val Gly
 1               5                  10                  15

Asp Arg Val Thr Ile Thr Cys Arg Val Ser Gln Gly Ile Ser Ser Tyr
                20                  25                  30

Leu Asn Trp Tyr Arg Gln Lys Pro Gly Lys Val Pro Lys Leu Leu Ile
                35                  40                  45

Tyr Ser Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Gly Gln Arg Thr Tyr Asn Ala Pro Tyr
                85                  90                  95

Thr Phe Gly Gln Gly Thr Lys Leu Glu Ile Lys
                100                 105

<210> SEQ ID NO 76
<211> LENGTH: 109
<212> TYPE: PRT
<213> ORGANISM: Homo sapiens

<400> SEQUENCE: 76

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ile
                20                  25                  30

Tyr Leu Ala Trp Tyr Gln Gln Lys Pro Gly Gln Ala Pro Arg Leu Leu
                35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                85                  90                  95

Pro Ile Thr Phe Gly Gln Gly Thr Arg Leu Glu Ile Lys
                100                 105

<210> SEQ ID NO 77
<211> LENGTH: 5
<212> TYPE: PRT
<213> ORGANISM: Homo sapiens

```
<400> SEQUENCE: 77

Ser Tyr Asp Met His
1               5

<210> SEQ ID NO 78
<211> LENGTH: 17
<212> TYPE: PRT
<213> ORGANISM: Homo sapiens

<400> SEQUENCE: 78

Ala Ile Trp Asn Asp Gly Ser Asn Lys Tyr Tyr Ala Asp Ser Val Lys
1               5                   10                  15

Gly

<210> SEQ ID NO 79
<211> LENGTH: 18
<212> TYPE: PRT
<213> ORGANISM: Homo sapiens

<400> SEQUENCE: 79

Asp Arg Ile Thr Met Val Arg Gly Val Ile Thr Gln Tyr Tyr Gly Met
1               5                   10                  15

Asp Val

<210> SEQ ID NO 80
<211> LENGTH: 11
<212> TYPE: PRT
<213> ORGANISM: Homo sapiens

<400> SEQUENCE: 80

Arg Val Ser Gln Gly Ile Ser Ser Tyr Leu Asn
1               5                   10

<210> SEQ ID NO 81
<211> LENGTH: 7
<212> TYPE: PRT
<213> ORGANISM: Homo sapiens

<400> SEQUENCE: 81

Ser Ala Ser Asn Leu Gln Ser
1               5

<210> SEQ ID NO 82
<211> LENGTH: 9
<212> TYPE: PRT
<213> ORGANISM: Homo sapiens

<400> SEQUENCE: 82

Gln Arg Thr Tyr Asn Ala Pro Tyr Thr
1               5

<210> SEQ ID NO 83
<211> LENGTH: 381
<212> TYPE: DNA
<213> ORGANISM: Homo sapiens

<400> SEQUENCE: 83
caggtgcagc tggtggagtc tgggggaggc gtggtccagc ctgggaggtc cctgagactc      60
tcctgtgcag cgtctggatt caccttcagt agctatgaca tgcactgggt ccgccaggct     120
ccaggcaagg ggctggagtg ggtggcagct atatggaatg atggaagtaa taaatactat     180
gcagactccg tgaagggccg attcaccatc tccagagaca attccaagaa cacgctgtat     240
```

```
ctgcaaatga acagcctgag agccgaggac acggctgtgt attactgtgc gagagaccgt    300
attactatgg ttcggggagt tattacccaa tactacggta tggacgtctg gggccaaggg    360
accacggtca ccgtctcctc a                                              381
```

<210> SEQ ID NO 84
<211> LENGTH: 321
<212> TYPE: DNA
<213> ORGANISM: Homo sapiens

<400> SEQUENCE: 84

```
gacatccagt tgacccagtc tccatcctcc ctgtctgcat ctgtaggaga cagagtcacc     60
atcacttgcc gggtgagtca gggcattagc agttatttaa attggtatcg cagaaaacca    120
gggaaagttc ctaagctcct gatctatagt gcatccaatt tgcaatctgg agtcccatct    180
cggttcagtg gcagtggatc tgggacagat ttcactctca ctatcagcag cctgcagcct    240
gaagatgttg caacttatta cggtcaacgg acttacaatg ccccgtacac ttttggccag    300
gggaccaagc tggagatcaa a                                              321
```

<210> SEQ ID NO 85
<211> LENGTH: 128
<212> TYPE: PRT
<213> ORGANISM: Homo sapiens

<400> SEQUENCE: 85

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Ala Trp Ile Arg Gln Pro Pro Gly Lys Ala Leu Glu
        35                  40                  45

Trp Leu Ala Leu Ile Tyr Trp Asp Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Ser Asn Met Asp Pro Val Asp Thr Ala Thr Tyr Tyr
                85                  90                  95

Cys Ala His Thr Arg Ile Ala Glu Val Arg Gly Val Ile Tyr Tyr Tyr
            100                 105                 110

Tyr Gly Ile Asp Val Trp Gly Gln Gly Thr Thr Val Thr Val Ser Ser
        115                 120                 125
```

<210> SEQ ID NO 86
<211> LENGTH: 107
<212> TYPE: PRT
<213> ORGANISM: Homo sapiens

<400> SEQUENCE: 86

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Val Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80
```

Pro Glu Asp Phe Ala Val Tyr Tyr Cys Gln Gln Tyr Gly Ser Ser Trp
            85                  90                  95

Thr Phe Gly Gln Gly Thr Lys Val Glu Ile Lys
            100                 105

<210> SEQ ID NO 87
<211> LENGTH: 7
<212> TYPE: PRT
<213> ORGANISM: Homo sapiens

<400> SEQUENCE: 87

Thr Ser Gly Val Gly Val Ala
1               5

<210> SEQ ID NO 88
<211> LENGTH: 16
<212> TYPE: PRT
<213> ORGANISM: Homo sapiens

<400> SEQUENCE: 88

Leu Ile Tyr Trp Asp Asp Lys Arg Tyr Ser Pro Ser Leu Lys Ser
1               5                   10                  15

<210> SEQ ID NO 89
<211> LENGTH: 18
<212> TYPE: PRT
<213> ORGANISM: Homo sapiens

<400> SEQUENCE: 89

Thr Arg Ile Ala Glu Val Arg Gly Val Ile Tyr Tyr Tyr Gly Ile
1               5                   10                  15

Asp Val

<210> SEQ ID NO 90
<211> LENGTH: 12
<212> TYPE: PRT
<213> ORGANISM: Homo sapiens

<400> SEQUENCE: 90

Arg Ala Ser Gln Ser Val Ser Ser Thr Tyr Leu Val
1               5                   10

<210> SEQ ID NO 91
<211> LENGTH: 7
<212> TYPE: PRT
<213> ORGANISM: Homo sapiens

<400> SEQUENCE: 91

Gly Ala Ser Ser Arg Ala Thr
1               5

<210> SEQ ID NO 92
<211> LENGTH: 8
<212> TYPE: PRT
<213> ORGANISM: Homo sapiens

<400> SEQUENCE: 92

Gln Gln Tyr Gly Ser Ser Trp Thr
1               5

<210> SEQ ID NO 93
<211> LENGTH: 384
<212> TYPE: DNA
<213> ORGANISM: Homo sapiens -continued

<400> SEQUENCE: 93

```
cagatcacct tgaaggagtc tggtcctacg ctggtgaagc ccacacagac cctcacgctg    60
acctgcacct tctctgggtt ctcactcagc actagtggag tgggtgtggc ctggatccgt   120
cagcccccag gaaaggccct ggagtggctt gcactcattt attgggatga tgataagcgc   180
tacagcccat ctctgaagag caggctcacc atcaccaagg acacctccaa aaaccaggtg   240
gtccttacaa tgagcaacat ggaccctgtg acacagcca catattactg tgcgcacacc    300
cgcattgctg aggttcgggg agttatatac tactactacg gtatagacgt ctggggccaa   360
gggaccacgg tcaccgtctc ctca                                           384
```

<210> SEQ ID NO 94
<211> LENGTH: 321
<212> TYPE: DNA
<213> ORGANISM: Homo sapiens

<400> SEQUENCE: 94

```
gaaattgtgt tgacgcagtc tccaggcacc ctgtctttgt ctccagggga aagagccacc    60
ctctcctgca gggccagtca gagtgttagc agcacctact tagtctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcgtggac gttcggccaa   300
gggaccaagg tggaaatcaa a                                              321
```

<210> SEQ ID NO 95
<211> LENGTH: 12
<212> TYPE: PRT
<213> ORGANISM: Homo sapiens

<400> SEQUENCE: 95

Arg Ala Ser Gln Ser Val Ser Ser Ile Tyr Leu Ala
1               5                   10

<210> SEQ ID NO 96
<211> LENGTH: 7
<212> TYPE: PRT
<213> ORGANISM: Homo sapiens

<400> SEQUENCE: 96

Gly Ala Ser Ser Arg Ala Thr
1               5

<210> SEQ ID NO 97
<211> LENGTH: 10
<212> TYPE: PRT
<213> ORGANISM: Homo sapiens

<400> SEQUENCE: 97

Gln Gln Tyr Gly Ser Ser Pro Pro Ile Thr
1               5                   10

<210> SEQ ID NO 98
<211> LENGTH: 327
<212> TYPE: DNA
<213> ORGANISM: Homo sapiens

<400> SEQUENCE: 98

```
gaaattgtgt tgacgcagtc tccaggcacc ctgtctttgt ctccagggga aagagccacc    60
```

-continued

```
ctctcctgca gggccagtca gagtgttagc agcatctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcacctcc gatcaccttc    300
ggccaaggga cacgactgga gattaaa                                        327
```

<210> SEQ ID NO 99
<211> LENGTH: 98
<212> TYPE: PRT
<213> ORGANISM: Homo sapiens

<400> SEQUENCE: 99

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg
```

<210> SEQ ID NO 100
<211> LENGTH: 95
<212> TYPE: PRT
<213> ORGANISM: Homo sapiens

<400> SEQUENCE: 100

```
Asp Ile Gln Leu Thr Gln Ser Pro Ser Ser Leu Ser Ala Ser Val Gly
1               5                   10                  15

Asp Arg Val Thr Ile Thr Cys Arg Val Ser Gln Gly Ile Ser Ser Tyr
            20                  25                  30

Leu Asn Trp Tyr Arg Gln Lys Pro Gly Lys Val Pro Lys Leu Leu Ile
        35                  40                  45

Tyr Ser Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Gly Gln Arg Thr Tyr Asn Ala Pro
                85                  90                  95
```